US010105201B2

(12) United States Patent
Woodard et al.

(10) Patent No.: US 10,105,201 B2
(45) Date of Patent: Oct. 23, 2018

(54) INTERDENTAL CLEANER USING WATER SUPPLY

(71) Applicant: WATER PIK, INC., Fort Collins, CO (US)

(72) Inventors: Brian J. Woodard, Boulder, CO (US); Jeffrey M. Garrigues, Firestone, CO (US)

(73) Assignee: Water Pik, Inc., Fort Collins, CO (US)

( * ) Notice: Subject to any disclaimer, the term of this patent is extended or adjusted under 35 U.S.C. 154(b) by 591 days.

(21) Appl. No.: 14/052,601

(22) Filed: Oct. 11, 2013

(65) Prior Publication Data
US 2014/0106296 A1 Apr. 17, 2014

Related U.S. Application Data

(60) Provisional application No. 61/712,771, filed on Oct. 11, 2012.

(51) Int. Cl.
A61C 1/00 (2006.01)
A61C 17/02 (2006.01)
A61C 15/04 (2006.01)
A61C 15/00 (2006.01)

(52) U.S. Cl.
CPC .......... *A61C 15/046* (2013.01); *A61C 1/0061* (2013.01); *A61C 15/00* (2013.01); *A61C 17/0202* (2013.01); *A61C 17/0214* (2013.01)

(58) Field of Classification Search
CPC ..... A61C 15/046; A61C 15/00; A61C 1/0061; A61C 17/0202; A61C 17/0214
See application file for complete search history.

(56) References Cited

U.S. PATENT DOCUMENTS

| 555,588 A | 3/1896 | Spencer |
| 1,278,225 A | 9/1918 | Schamberg |
| 1,452,258 A | 4/1923 | Smith |
| 1,464,419 A | 8/1923 | Gill |
| 1,480,310 A | 1/1924 | Smith |

(Continued)

FOREIGN PATENT DOCUMENTS

| CA | 851479 | 9/1970 |
| CH | 502817 A | 2/1971 |

(Continued)

OTHER PUBLICATIONS

US RE27,274, 01/1972, Mattingly (withdrawn)

(Continued)

Primary Examiner — Quang D Thanh
(74) Attorney, Agent, or Firm — Dorsey & Whitney LLP

(57) ABSTRACT

The present disclosure is related to an interdental cleaner for operably connecting to an external water supply. The interdental cleaner includes a mounting bracket having a bracket inlet fluidly connected to the external water supply and a pressure regulation assembly operably connected to the mounting bracket. The pressure regulation assembly includes a regulation outlet fluidly connected to the bracket inlet. The interdental cleaner further includes a water flosser operably connected to the mounting bracket and fluidly connected to the regulation outlet. During use, water pressure of water at the regulation outlet is lower than a water pressure of water at the bracket inlet.

7 Claims, 63 Drawing Sheets

(56) References Cited

U.S. PATENT DOCUMENTS

| | | |
|---|---|---|
| 1,498,267 A | 6/1924 | Hachman |
| 1,650,686 A | 11/1927 | Binks |
| 1,669,889 A | 5/1928 | Andrews et al. |
| 1,681,320 A | 8/1928 | Bergl et al. |
| 1,933,454 A | 10/1933 | Sidney |
| 1,940,111 A | 12/1933 | Austin |
| D93,019 S | 8/1934 | Hose |
| 1,977,782 A | 10/1934 | Roy |
| 2,107,686 A | 2/1938 | Bramsen et al. |
| 2,230,238 A | 2/1941 | Duberstein et al. |
| 2,417,759 A | 3/1947 | Johnson |
| D159,872 S | 8/1950 | Skold |
| 2,531,730 A | 11/1950 | Henderson |
| 2,595,666 A | 5/1952 | Hutson |
| 2,669,233 A | 2/1954 | Friend |
| 2,794,437 A | 6/1954 | Tash |
| 2,709,227 A | 5/1955 | Foley et al. |
| 2,783,919 A | 3/1957 | Ansell |
| 2,870,932 A | 1/1959 | Davis |
| 2,984,452 A | 5/1961 | Hooper |
| 3,089,490 A | 5/1963 | Goldberg |
| 3,096,913 A | 7/1963 | Jousson |
| 3,144,867 A | 8/1964 | Trupp et al. |
| D202,041 S | 8/1965 | Burzlaff |
| 3,209,956 A | 10/1965 | McKenzie |
| 3,216,619 A | 11/1965 | Richards et al. |
| 3,225,759 A | 12/1965 | Drapen et al. |
| 3,227,158 A | 1/1966 | Mattingly |
| 3,266,623 A | 8/1966 | Poferl |
| 3,297,558 A | 1/1967 | Hillquist |
| D208,778 S | 10/1967 | Koch |
| D209,204 S | 11/1967 | St. Clair et al. |
| D209,395 S | 11/1967 | Gilbert |
| D210,018 S | 1/1968 | Mattingly et al. |
| D210,019 S | 1/1968 | Johnson et al. |
| 3,370,214 A | 2/1968 | Aymar |
| 3,391,696 A | 7/1968 | Woodward |
| 3,393,673 A | 7/1968 | Mattingly et al. |
| 3,400,999 A | 9/1968 | Goldstein |
| 3,418,552 A | 12/1968 | Holmes |
| 3,420,228 A | 1/1969 | Kalbfeld |
| 3,425,410 A | 2/1969 | Cammack |
| 3,453,969 A | 7/1969 | Mattingly |
| 3,465,751 A | 9/1969 | Powers |
| D215,920 S | 11/1969 | McCarty et al. |
| 3,487,828 A | 1/1970 | Troy |
| 3,489,268 A | 1/1970 | Meierhoefer |
| 3,495,587 A | 2/1970 | Freedman |
| 3,496,933 A | 2/1970 | Lloyd |
| 3,499,440 A | 3/1970 | Gibbs |
| 3,500,824 A | 3/1970 | Gilbert |
| 3,501,203 A | 3/1970 | Falk |
| 3,502,072 A | 3/1970 | Stillman |
| 3,517,669 A | 6/1970 | Buono et al. |
| D218,270 S | 8/1970 | Soper |
| 3,522,801 A | 8/1970 | Robinson |
| 3,532,221 A | 10/1970 | Kaluhiokalani et al. |
| 3,536,065 A | 10/1970 | Moret |
| 3,537,444 A | 11/1970 | Garn |
| 3,538,950 A | 11/1970 | Porteners |
| 3,547,110 A | 12/1970 | Balamuth |
| 3,561,433 A | 2/1971 | Kovach |
| D220,334 S | 3/1971 | Mackay et al. |
| 3,570,525 A | 3/1971 | Borsum |
| 3,572,375 A | 3/1971 | Rosenberg |
| 3,578,884 A | 5/1971 | Jacobson |
| D220,996 S | 6/1971 | Irons |
| 3,583,609 A | 6/1971 | Oppenheimer |
| 3,590,813 A | 7/1971 | Roszyk |
| 3,608,548 A | 9/1971 | Lewis |
| D222,862 S | 1/1972 | Cook |
| 3,636,947 A | 1/1972 | Balamuth |
| 3,651,576 A | 3/1972 | Massa |
| 3,669,101 A | 6/1972 | Kleiner |
| 3,703,170 A | 11/1972 | Ryckman, Jr. |
| 3,747,595 A | 7/1973 | Grossan |
| 3,768,472 A | 10/1973 | Hodosh et al. |
| 3,783,364 A | 1/1974 | Gallanis et al. |
| 3,809,506 A | 5/1974 | Malcosky |
| 3,809,977 A | 5/1974 | Balamuth et al. |
| 3,811,432 A | 5/1974 | Moret |
| 3,820,532 A | 6/1974 | Eberhardt et al. |
| 3,827,147 A | 8/1974 | Condon |
| 3,837,166 A | 9/1974 | Hiraoka |
| 3,840,795 A | 10/1974 | Roszyk et al. |
| 3,847,145 A | 11/1974 | Grossan |
| 3,854,209 A | 12/1974 | Franklin et al. |
| 3,863,628 A | 2/1975 | Vit |
| 3,871,560 A | 3/1975 | Crippa |
| 3,874,506 A | 4/1975 | Hill et al. |
| 3,881,868 A | 5/1975 | Duke |
| 3,898,739 A | 8/1975 | Gayso |
| 3,912,125 A | 10/1975 | Acklin |
| 3,943,628 A | 3/1976 | Kronman et al. |
| 3,959,883 A | 6/1976 | Walls et al. |
| 3,973,558 A | 8/1976 | Stouffer et al. |
| 3,977,084 A | 8/1976 | Sloan |
| 4,001,526 A | 1/1977 | Olson |
| 4,004,302 A | 1/1977 | Hori |
| 4,007,739 A | 2/1977 | Bron et al. |
| 4,013,227 A | 3/1977 | Herrera |
| 4,052,002 A | 10/1977 | Stouffer et al. |
| D246,667 S | 12/1977 | Mackay et al. |
| D246,668 S | 12/1977 | Mackay et al. |
| 4,060,870 A | 12/1977 | Cannarella |
| 4,075,761 A | 2/1978 | Behne et al. |
| 4,078,558 A | 3/1978 | Woog et al. |
| 4,094,311 A | 6/1978 | Hudson |
| 4,108,167 A | 8/1978 | Hickman et al. |
| 4,108,178 A | 8/1978 | Betush |
| 4,109,650 A | 8/1978 | Peclard |
| 4,122,845 A | 10/1978 | Stouffer et al. |
| 4,135,501 A | 1/1979 | Leunissan |
| 4,141,352 A | 2/1979 | Ebner et al. |
| 4,144,646 A | 3/1979 | Takemoto et al. |
| 4,149,315 A | 4/1979 | Page, Jr. et al. |
| 4,154,375 A | 5/1979 | Bippus |
| 4,160,383 A | 7/1979 | Rauschenberger |
| 4,171,572 A | 10/1979 | Nash |
| 4,182,038 A | 1/1980 | Fleer |
| 4,200,235 A | 4/1980 | Monschke |
| 4,201,200 A | 5/1980 | Hubner |
| 4,215,476 A | 8/1980 | Armstrong |
| 4,219,618 A | 8/1980 | Leonard |
| 4,227,878 A | 10/1980 | Lohn |
| 4,229,634 A | 10/1980 | Hickman et al. |
| 4,236,889 A | 12/1980 | Wright |
| D258,097 S | 2/1981 | Wistrand |
| 4,248,589 A | 2/1981 | Lewis |
| 4,249,899 A | 2/1981 | Davis |
| 4,257,458 A | 3/1981 | Kondo et al. |
| 4,262,799 A | 4/1981 | Perrett |
| 4,266,934 A | 5/1981 | Pernot |
| 4,276,023 A | 6/1981 | Phillips et al. |
| 4,276,880 A | 7/1981 | Malmin |
| 4,302,186 A | 11/1981 | Cammack et al. |
| 4,303,064 A | 12/1981 | Buffa |
| 4,303,070 A | 12/1981 | Ichikawa et al. |
| 4,306,862 A | 12/1981 | Knox |
| 4,315,741 A | 2/1982 | Reichl |
| 4,319,568 A | 4/1982 | Tregoning |
| 4,331,422 A | 5/1982 | Heyman |
| 4,337,040 A | 6/1982 | Cammack et al. |
| 4,340,365 A | 7/1982 | Pisanu |
| 4,340,368 A | 7/1982 | Lococo |
| D266,117 S | 9/1982 | Oberheim |
| 4,353,694 A | 10/1982 | Pelerin |
| 4,363,626 A | 12/1982 | Schmidt et al. |
| 4,365,376 A | 12/1982 | Oda et al. |
| 4,370,131 A | 1/1983 | Banko |
| 4,374,354 A | 2/1983 | Petrovic et al. |
| 4,382,167 A | 5/1983 | Maruyama et al. |
| 4,382,786 A | 5/1983 | Lohn |
| D270,000 S | 8/1983 | Ketler |

(56) References Cited

U.S. PATENT DOCUMENTS

| | | |
|---|---|---|
| 4,412,823 A | 11/1983 | Sakai et al. |
| 4,416,628 A | 11/1983 | Cammack |
| 4,442,830 A | 4/1984 | Markau |
| 4,442,831 A | 4/1984 | Trenary |
| 4,452,238 A | 6/1984 | Kerr |
| 4,454,866 A | 6/1984 | Fayen |
| 4,512,769 A | 4/1985 | Kozam et al. |
| 4,517,962 A | 5/1985 | Heckele |
| 4,531,912 A | 7/1985 | Schuss et al. |
| 4,531,913 A | 7/1985 | Taguchi |
| 4,534,340 A | 8/1985 | Kerr et al. |
| 4,552,130 A | 11/1985 | Kinoshita |
| 4,561,214 A | 12/1985 | Inoue |
| D283,374 S | 4/1986 | Cheuk-Yiu |
| 4,585,415 A | 4/1986 | Hommann |
| 4,591,777 A | 5/1986 | McCarty et al. |
| 4,592,728 A | 6/1986 | Davis |
| 4,602,906 A | 7/1986 | Grunenfelder |
| 4,607,627 A | 8/1986 | Leber et al. |
| 4,613,074 A | 9/1986 | Schulze |
| 4,619,009 A | 10/1986 | Rosenstatter |
| 4,619,612 A | 10/1986 | Weber et al. |
| 4,629,425 A | 12/1986 | Detsch |
| 4,636,198 A | 1/1987 | Stade |
| 4,642,037 A | 2/1987 | Fritchman |
| 4,644,937 A | 2/1987 | Hommann |
| 4,645,488 A | 2/1987 | Matukas |
| 4,647,831 A | 3/1987 | O'Malley et al. |
| 4,648,838 A | 3/1987 | Schlachter |
| 4,650,475 A | 3/1987 | Smith et al. |
| 4,655,198 A | 4/1987 | Hommann |
| 4,669,453 A | 6/1987 | Atkinson et al. |
| 4,672,953 A | 6/1987 | DiVito |
| 4,673,396 A | 6/1987 | Urbaniak |
| D291,354 S | 8/1987 | Camens |
| 4,716,352 A | 12/1987 | Hurn et al. |
| 4,749,340 A | 6/1988 | Ikeda et al. |
| 4,770,632 A | 9/1988 | Ryder et al. |
| D298,565 S | 11/1988 | Kohler, Jr. et al. |
| 4,783,321 A | 11/1988 | Spence |
| 4,787,845 A | 11/1988 | Valentine |
| 4,787,847 A | 11/1988 | Martin et al. |
| 4,798,292 A | 1/1989 | Hauze |
| 4,803,974 A | 2/1989 | Powell |
| 4,804,364 A | 2/1989 | Dieras et al. |
| 4,818,229 A | 4/1989 | Vasile |
| 4,820,152 A | 4/1989 | Warrin et al. |
| 4,821,923 A | 4/1989 | Skorka |
| 4,824,368 A | 4/1989 | Hickman |
| 4,826,431 A | 5/1989 | Fujimura et al. |
| 4,827,551 A | 5/1989 | Maser et al. |
| 4,832,683 A | 5/1989 | Idemoto et al. |
| 4,854,869 A | 8/1989 | Lawhorn |
| 4,861,340 A | 8/1989 | Smith et al. |
| 4,862,876 A | 9/1989 | Lih-Sheng |
| 4,869,720 A | 9/1989 | Chernack |
| 4,880,382 A | 11/1989 | Moret et al. |
| 4,886,452 A | 12/1989 | Lohn |
| 4,900,252 A | 2/1990 | Liefke et al. |
| 4,902,225 A | 2/1990 | Lohn |
| 4,903,687 A | 2/1990 | Lih-Sheng |
| 4,906,187 A | 3/1990 | Amadera |
| 4,907,744 A | 3/1990 | Jousson |
| 4,915,304 A | 4/1990 | Campani |
| 4,925,450 A | 5/1990 | Imonti et al. |
| 4,928,675 A | 5/1990 | Thornton |
| 4,930,660 A | 6/1990 | Porteous |
| 4,941,459 A | 7/1990 | Mathur |
| 4,950,159 A | 8/1990 | Hansen |
| 4,958,629 A | 9/1990 | Peace et al. |
| 4,958,751 A | 9/1990 | Curtis et al. |
| 4,959,199 A | 9/1990 | Brewer |
| 4,961,698 A | 10/1990 | Vlock |
| 4,966,551 A | 10/1990 | Betush |
| 4,969,874 A | 11/1990 | Michel et al. |
| 4,973,246 A | 11/1990 | Black |
| 4,973,247 A | 11/1990 | Varnes et al. |
| 4,973,250 A | 11/1990 | Milman |
| 4,975,054 A | 12/1990 | Esrock |
| 4,979,503 A | 12/1990 | Chernack |
| 4,979,504 A | 12/1990 | Mills |
| 4,989,590 A | 2/1991 | Baum et al. |
| 4,998,880 A | 3/1991 | Nerli |
| 5,013,241 A | 5/1991 | Von Gutfeld et al. |
| 5,014,884 A | 5/1991 | Wunsch |
| 5,019,054 A | 5/1991 | Clement et al. |
| 5,027,798 A | 7/1991 | Primiano |
| 5,029,576 A | 7/1991 | Evans, Sr. |
| 5,033,617 A | 7/1991 | Hartwein et al. |
| 5,033,961 A | 7/1991 | Kankler et al. |
| D318,918 S | 8/1991 | Hartwein |
| 5,046,486 A | 9/1991 | Grulke et al. |
| 5,049,071 A | 9/1991 | Davis et al. |
| 5,060,825 A | 10/1991 | Palmer et al. |
| 5,061,180 A | 10/1991 | Wiele |
| 5,062,795 A | 11/1991 | Woog |
| 5,064,168 A | 11/1991 | Raines et al. |
| D322,314 S | 12/1991 | Ohbayashi |
| 5,071,346 A | 12/1991 | Domaas |
| 5,082,115 A | 1/1992 | Hutcheson |
| 5,082,443 A | 1/1992 | Lohn |
| 5,085,317 A | 2/1992 | Jensen et al. |
| 5,086,756 A | 2/1992 | Powell |
| 5,095,893 A | 3/1992 | Rawden, Jr. |
| 5,098,291 A | 3/1992 | Curtis et al. |
| 5,098,676 A | 3/1992 | Brooks, Jr. |
| 5,100,319 A | 3/1992 | Baum |
| 5,117,871 A | 6/1992 | Gardner et al. |
| 5,125,835 A | 6/1992 | Young |
| 5,127,831 A | 7/1992 | Bab |
| 5,142,723 A | 9/1992 | Lustig et al. |
| 5,150,841 A | 9/1992 | Silvenis et al. |
| 5,172,810 A | 12/1992 | Brewer |
| 5,173,273 A | 12/1992 | Brewer |
| 5,183,035 A | 2/1993 | Weir |
| 5,197,458 A | 3/1993 | Ito et al. |
| 5,197,460 A | 3/1993 | Ito et al. |
| 5,199,871 A | 4/1993 | Young |
| 5,203,697 A | 4/1993 | Malmin |
| 5,203,769 A | 4/1993 | Clement et al. |
| 5,204,004 A | 4/1993 | Johnston et al. |
| 5,208,933 A | 5/1993 | Lustig et al. |
| 5,215,193 A | 6/1993 | Dennis |
| 5,218,956 A * | 6/1993 | Handler ............ A61C 17/0214 433/80 |
| 5,220,914 A | 6/1993 | Thompson |
| 5,228,646 A | 7/1993 | Raines |
| 5,230,624 A | 7/1993 | Wolf et al. |
| 5,232,687 A | 8/1993 | Geimer |
| 5,235,968 A | 8/1993 | Woog |
| 5,241,714 A | 9/1993 | Barry |
| 5,246,367 A | 9/1993 | Ito et al. |
| 5,252,064 A | 10/1993 | Baum et al. |
| D341,200 S | 11/1993 | Yoshimoto |
| 5,257,933 A | 11/1993 | Jousson |
| 5,261,448 A | 11/1993 | Furuya et al. |
| D341,943 S | 12/1993 | Si-Hoe |
| 5,267,586 A | 12/1993 | Jankavaara |
| 5,269,684 A | 12/1993 | Fischer |
| 5,281,137 A | 1/1994 | Jousson |
| 5,281,139 A | 1/1994 | Frank et al. |
| 5,282,745 A | 2/1994 | Wiltrout et al. |
| 5,286,192 A | 2/1994 | Dixon |
| 5,286,201 A | 2/1994 | Yu |
| 5,295,832 A | 3/1994 | Evans |
| 5,297,962 A | 3/1994 | O'Connor et al. |
| D346,212 S | 4/1994 | Hosl |
| 5,301,381 A | 4/1994 | Klupt |
| 5,302,123 A | 4/1994 | Bechard |
| 5,317,691 A | 5/1994 | Traeger |
| 5,321,865 A | 6/1994 | Kaeser |
| 5,331,704 A | 7/1994 | Rosen et al. |
| 5,344,317 A | 9/1994 | Pacher et al. |
| 5,346,677 A | 9/1994 | Risk |

(56) References Cited

U.S. PATENT DOCUMENTS

| | | | |
|---|---|---|---|
| D351,892 S | 10/1994 | Wolf et al. | |
| 5,360,338 A | 11/1994 | Waggoner | |
| 5,368,548 A | 11/1994 | Jousson | |
| 5,370,534 A | 12/1994 | Wolf et al. | |
| D354,168 S | 1/1995 | Hartwein | |
| D354,559 S | 1/1995 | Knute | |
| 5,378,149 A | 1/1995 | Stropko | |
| 5,380,201 A | 1/1995 | Kawata | |
| D356,864 S | 3/1995 | Woog | |
| 5,399,089 A | 3/1995 | Eichman et al. | |
| D358,883 S | 5/1995 | Vos | |
| 5,456,672 A | 10/1995 | Diederich et al. | |
| 5,465,445 A | 11/1995 | Yeh | |
| 5,467,495 A | 11/1995 | Boland et al. | |
| 5,468,148 A | 11/1995 | Ricks | |
| 5,470,305 A | 11/1995 | Arnett et al. | |
| 5,474,450 A | 12/1995 | Chronister | |
| 5,474,451 A | 12/1995 | Dalrymple et al. | |
| 5,476,379 A | 12/1995 | Disel | |
| 5,484,281 A * | 1/1996 | Renow | A61C 17/0214 433/80 |
| 5,487,877 A | 1/1996 | Choi | |
| 5,490,779 A | 2/1996 | Malmin | |
| 5,505,916 A | 4/1996 | Berry, Jr. | |
| D369,656 S | 5/1996 | Vos | |
| D370,125 S | 5/1996 | Craft et al. | |
| 5,525,058 A | 6/1996 | Gallant et al. | |
| 5,526,841 A | 6/1996 | Detsch et al. | |
| 5,540,587 A | 7/1996 | Malmin | |
| 5,547,374 A | 8/1996 | Coleman | |
| D373,631 S | 9/1996 | Maeda et al. | |
| 5,554,014 A | 9/1996 | Becker | |
| 5,554,025 A | 9/1996 | Kinsel | |
| 5,556,001 A | 9/1996 | Weissman et al. | |
| 5,564,629 A | 10/1996 | Weissman et al. | |
| D376,893 S | 12/1996 | Gornet | |
| D377,091 S | 12/1996 | Scott, Sr. | |
| 5,613,259 A | 3/1997 | Craft et al. | |
| 5,616,028 A | 4/1997 | Hafele et al. | |
| 5,626,472 A * | 5/1997 | Pennetta | A61C 17/0214 433/80 |
| 5,634,791 A | 6/1997 | Matsuura et al. | |
| 5,636,987 A | 6/1997 | Serfaty | |
| 5,640,735 A | 6/1997 | Manning | |
| D382,407 S | 8/1997 | Craft et al. | |
| 5,653,591 A | 8/1997 | Loge | |
| 5,659,995 A | 8/1997 | Hoffman | |
| 5,667,483 A | 9/1997 | Santos | |
| D386,576 S | 11/1997 | Wang et al. | |
| 5,683,192 A | 11/1997 | Kilfoil | |
| 5,685,829 A | 11/1997 | Allen | |
| 5,685,851 A | 11/1997 | Murphy et al. | |
| 5,697,784 A | 12/1997 | Hafele et al. | |
| D388,612 S | 1/1998 | Stutzer et al. | |
| D388,613 S | 1/1998 | Stutzer et al. | |
| D389,091 S | 1/1998 | Dickinson | |
| 5,709,545 A | 1/1998 | Johnston et al. | |
| D390,934 S | 2/1998 | McKeone | |
| 5,716,007 A | 2/1998 | Nottingham et al. | |
| 5,718,668 A | 2/1998 | Arnett et al. | |
| 5,746,595 A | 5/1998 | Ford | |
| 5,749,726 A | 5/1998 | Kinsel | |
| 5,759,502 A | 6/1998 | Spencer et al. | |
| 5,779,471 A | 7/1998 | Tseng | |
| 5,779,654 A | 7/1998 | Foley et al. | |
| 5,795,153 A | 8/1998 | Rechmann | |
| 5,796,325 A | 8/1998 | Lundell et al. | |
| 5,833,065 A | 11/1998 | Burgess | |
| 5,836,030 A | 11/1998 | Hazeu et al. | |
| D402,744 S | 12/1998 | Zuege | |
| 5,851,079 A | 12/1998 | Horstman et al. | |
| D403,511 S | 1/1999 | Serbinski | |
| D406,334 S | 3/1999 | Rosenthal et al. | |
| 5,876,201 A | 3/1999 | Wilson et al. | |
| D408,511 S | 4/1999 | Allen et al. | |
| 5,901,397 A | 5/1999 | Häfele et al. | |
| 5,934,902 A | 8/1999 | Abahusayn | |
| D413,975 S | 9/1999 | Maeda | |
| D416,999 S | 11/1999 | Miyamoto | |
| D417,082 S | 11/1999 | Classen et al. | |
| 5,993,402 A | 11/1999 | Sauer et al. | |
| 6,030,215 A | 2/2000 | Ellion et al. | |
| 6,038,960 A | 3/2000 | Fukushima et al. | |
| 6,039,180 A | 3/2000 | Grant | |
| 6,047,429 A | 4/2000 | Wu | |
| D424,181 S | 5/2000 | Caplow | |
| D425,615 S | 5/2000 | Bachman et al. | |
| D425,981 S | 5/2000 | Bachman et al. | |
| 6,056,548 A | 5/2000 | Neuberger et al. | |
| 6,056,710 A | 5/2000 | Bachman et al. | |
| D426,633 S | 6/2000 | Bachman et al. | |
| 6,089,865 A | 7/2000 | Edgar | |
| 6,116,866 A | 9/2000 | Tomita et al. | |
| 6,120,755 A | 9/2000 | Jacobs | |
| 6,124,699 A | 9/2000 | Suzuki et al. | |
| D434,500 S | 11/2000 | Pollock et al. | |
| 6,159,006 A | 12/2000 | Cook et al. | |
| 6,164,967 A | 12/2000 | Sale et al. | |
| D435,905 S | 1/2001 | Bachman et al. | |
| D437,049 S | 1/2001 | Hartwein | |
| 6,193,512 B1 | 2/2001 | Wallace | |
| 6,193,932 B1 | 2/2001 | Wu et al. | |
| 6,199,239 B1 | 3/2001 | Dickerson | |
| D439,781 S | 4/2001 | Spore | |
| 6,217,835 B1 | 4/2001 | Riley et al. | |
| D441,861 S | 5/2001 | Hafliger | |
| 6,233,773 B1 | 5/2001 | Karge et al. | |
| 6,234,205 B1 | 5/2001 | D'Amelio et al. | |
| 6,237,178 B1 | 5/2001 | Krammer et al. | |
| 6,247,929 B1 | 6/2001 | Bachman et al. | |
| 6,280,190 B1 | 8/2001 | Hoffman | |
| D448,236 S | 9/2001 | Murray | |
| 6,293,792 B1 | 9/2001 | Hanson | |
| D449,884 S | 10/2001 | Tobin et al. | |
| D453,453 S | 2/2002 | Lun | |
| D455,201 S | 4/2002 | Jones | |
| D455,203 S | 4/2002 | Jones | |
| 6,363,565 B1 | 4/2002 | Paffrath | |
| D457,949 S | 5/2002 | Krug | |
| D464,799 S | 10/2002 | Crossman et al. | |
| 6,468,482 B1 | 10/2002 | Frieze et al. | |
| 6,475,173 B1 | 11/2002 | Bachman et al. | |
| 6,485,451 B1 | 11/2002 | Roberts et al. | |
| 6,497,375 B1 | 12/2002 | Srinath et al. | |
| 6,497,572 B2 | 12/2002 | Hood et al. | |
| 6,502,584 B1 | 1/2003 | Fordham | |
| D470,660 S | 2/2003 | Schaber | |
| 6,558,344 B2 | 5/2003 | McKinnon et al. | |
| 6,561,808 B2 | 5/2003 | Neuberger et al. | |
| D475,346 S | 6/2003 | McCurrach et al. | |
| D476,743 S | 7/2003 | D'Silva | |
| 6,589,477 B1 | 7/2003 | Frieze et al. | |
| 6,602,071 B1 | 8/2003 | Ellion et al. | |
| 6,632,091 B1 | 10/2003 | Cise et al. | |
| D482,451 S | 11/2003 | Page et al. | |
| 6,640,999 B2 | 11/2003 | Peterson | |
| 6,647,577 B2 | 11/2003 | Tam | |
| 6,659,674 B2 | 12/2003 | Carlucci et al. | |
| 6,663,386 B1 | 12/2003 | Moelsgaard | |
| 6,669,059 B2 | 12/2003 | Mehta | |
| D484,971 S | 1/2004 | Hartwein | |
| 6,681,418 B1 * | 1/2004 | Bierend | E03D 1/32 137/494 |
| D486,573 S | 2/2004 | Callaghan et al. | |
| 6,689,078 B1 | 2/2004 | Rehkemper et al. | |
| 6,699,208 B2 | 3/2004 | Bachman et al. | |
| 6,719,561 B2 | 4/2004 | Gugel et al. | |
| D489,183 S | 5/2004 | Akahori et al. | |
| 6,739,782 B1 | 5/2004 | Rehkemper et al. | |
| 6,740,053 B2 | 5/2004 | Kaplowitz | |
| D490,899 S | 6/2004 | Gagnon | |
| D491,728 S | 6/2004 | Jimenez | |
| D492,996 S | 7/2004 | Rehkemper et al. | |
| 6,761,324 B2 | 7/2004 | Chang | |

(56) References Cited

U.S. PATENT DOCUMENTS

| | | |
|---|---|---|
| 6,766,549 B2 | 7/2004 | Klupt |
| D495,142 S | 8/2004 | Berde |
| D495,143 S | 8/2004 | Berde |
| 6,779,216 B2 | 8/2004 | Davies et al. |
| 6,783,004 B1 | 8/2004 | Rinner |
| 6,783,505 B1 | 8/2004 | Lai |
| 6,796,796 B2 | 9/2004 | Segal |
| 6,808,331 B2 | 10/2004 | Hall et al. |
| D498,643 S | 11/2004 | Pryor |
| 6,814,259 B1 | 11/2004 | Foster et al. |
| D499,885 S | 12/2004 | Xi |
| 6,835,181 B2 | 12/2004 | Hippensteel |
| D500,599 S | 1/2005 | Callaghan |
| 6,837,708 B2 | 1/2005 | Chen et al. |
| 6,884,069 B2 | 4/2005 | Goldman |
| 6,902,337 B1 | 6/2005 | Kuo |
| 6,907,879 B2 | 6/2005 | Drinan et al. |
| D509,585 S | 9/2005 | Kling et al. |
| D513,638 S | 1/2006 | Pan |
| D515,215 S | 2/2006 | Wang |
| D522,652 S | 6/2006 | Massey |
| 7,080,980 B2 | 7/2006 | Klupt |
| D529,661 S | 10/2006 | Schmidt |
| D530,010 S | 10/2006 | Luettgen et al. |
| 7,117,555 B2 | 10/2006 | Fattori et al. |
| D532,570 S | 11/2006 | Vizcarra |
| 7,131,838 B2 | 11/2006 | Suzuki et al. |
| D533,720 S | 12/2006 | Vu |
| 7,147,468 B2 | 12/2006 | Snyder et al. |
| D538,474 S | 3/2007 | Sheppard et al. |
| D548,334 S | 8/2007 | Izumi |
| D550,097 S | 9/2007 | Lepoitevin |
| D553,980 S | 10/2007 | VerWeyst |
| 7,276,035 B2 | 10/2007 | Lu |
| 7,314,456 B2 | 1/2008 | Shaw |
| D565,175 S | 3/2008 | Boyd et al. |
| 7,344,510 B1 | 3/2008 | Yande |
| D565,713 S | 4/2008 | Gao |
| 7,367,803 B2 | 5/2008 | Egeresi |
| D574,952 S | 8/2008 | Boyd et al. |
| D577,198 S | 9/2008 | Jimenez |
| D577,814 S | 9/2008 | Seki et al. |
| D581,279 S | 11/2008 | Oates |
| 7,455,521 B2 | 11/2008 | Fishburne, Jr. |
| 7,469,440 B2 | 12/2008 | Boland et al. |
| D585,132 S | 1/2009 | Pukall |
| D588,262 S | 3/2009 | Pukall |
| 7,500,584 B2 | 3/2009 | Schutz |
| D590,492 S | 4/2009 | Powell |
| D592,748 S | 5/2009 | Boulton |
| D595,136 S | 6/2009 | Canamasas Puigbo |
| D601,694 S | 10/2009 | Rocklin |
| D601,697 S | 10/2009 | Sobeich et al. |
| D603,708 S | 11/2009 | Handy |
| D608,430 S | 1/2010 | Slothower |
| 7,670,141 B2 | 3/2010 | Thomas et al. |
| 7,677,888 B1 | 3/2010 | Halm |
| D613,550 S | 4/2010 | Picozza et al. |
| D621,949 S | 8/2010 | Seki et al. |
| D622,928 S | 9/2010 | Griebel |
| D623,376 S | 9/2010 | Griebel |
| D625,406 S | 10/2010 | Seki et al. |
| 7,814,585 B1 | 10/2010 | Reich |
| D629,884 S | 12/2010 | Stephens |
| 7,857,623 B2 | 12/2010 | Grez |
| 7,862,536 B2 | 1/2011 | Chen et al. |
| 7,878,403 B2 | 2/2011 | Hennick et al. |
| 7,959,597 B2 | 6/2011 | Baker et al. |
| D640,872 S | 7/2011 | Nanda |
| D648,539 S | 11/2011 | Wai |
| D651,409 S | 1/2012 | Papenfu |
| D651,805 S | 1/2012 | Hay |
| D653,340 S | 1/2012 | Goerge et al. |
| 8,113,832 B2 | 2/2012 | Snyder et al. |
| D655,380 S | 3/2012 | Taylor |
| D658,381 S | 5/2012 | Gebski |
| D658,538 S | 5/2012 | Korzeniowski |
| 8,220,726 B2 | 7/2012 | Qiu et al. |
| D666,912 S | 9/2012 | Kawai |
| 8,256,979 B2 | 9/2012 | Hilscher et al. |
| D668,339 S | 10/2012 | Luoto |
| D669,169 S | 10/2012 | Washington et al. |
| 8,297,534 B2 | 10/2012 | Li et al. |
| D670,373 S | 11/2012 | Taylor et al. |
| D670,958 S | 11/2012 | Picozza et al. |
| D671,637 S | 11/2012 | Gebski et al. |
| D672,018 S | 12/2012 | Bucher |
| 8,366,024 B2 | 2/2013 | Leber |
| 8,403,577 B2 | 3/2013 | Khoshnevis |
| 8,403,665 B2 | 3/2013 | Thomas et al. |
| 8,408,483 B2 | 4/2013 | Boyd et al. |
| 8,418,300 B2 | 4/2013 | Miller et al. |
| D686,311 S | 7/2013 | Mori |
| D694,378 S | 11/2013 | Bates |
| D694,398 S | 11/2013 | Taylor |
| D700,343 S | 2/2014 | Liu |
| D702,819 S | 4/2014 | Garland |
| D702,821 S | 4/2014 | Garland |
| D707,350 S | 6/2014 | Woodard |
| D709,183 S | 7/2014 | Kemlein |
| D714,929 S | 10/2014 | Kim et al. |
| D714,930 S | 10/2014 | Kim et al. |
| D717,427 S | 11/2014 | Kim |
| D718,855 S | 12/2014 | Kim et al. |
| D723,387 S | 3/2015 | Fath |
| D725,770 S | 3/2015 | Kim et al. |
| D731,640 S | 6/2015 | Kim et al. |
| D740,936 S | 10/2015 | Kim et al. |
| D745,329 S | 12/2015 | Ong |
| D746,975 S | 1/2016 | Schenck |
| D747,464 S | 1/2016 | Taylor |
| D754,330 S | 4/2016 | Kim et al. |
| D756,122 S | 5/2016 | Taylor |
| D782,326 S | 3/2017 | Fath |
| 2002/0090252 A1 | 7/2002 | Hall et al. |
| 2002/0108193 A1 | 8/2002 | Gruber |
| 2002/0119415 A1 | 8/2002 | Bailey |
| 2002/0152565 A1 | 10/2002 | Klupt |
| 2003/0060743 A1 | 3/2003 | Chang |
| 2003/0098249 A1 | 5/2003 | Rollock |
| 2003/0204155 A1 | 10/2003 | Egeresi |
| 2003/0213075 A1 | 11/2003 | Hui et al. |
| 2004/0045107 A1 | 3/2004 | Egeresi |
| 2004/0076921 A1 | 4/2004 | Gofman et al. |
| 2004/0122377 A1 | 6/2004 | Fischer et al. |
| 2004/0126730 A1 | 7/2004 | Panagotacos |
| 2004/0209222 A1 | 10/2004 | Snyder |
| 2005/0049620 A1 | 3/2005 | Chang |
| 2005/0064371 A1 | 3/2005 | Soukos et al. |
| 2005/0101894 A1 | 5/2005 | Hippensteel |
| 2005/0102773 A1 | 5/2005 | Obermann et al. |
| 2005/0144745 A1 | 7/2005 | Russell |
| 2005/0177079 A1 | 8/2005 | Pan |
| 2005/0271531 A1 | 12/2005 | Brown et al. |
| 2006/0008373 A1 | 1/2006 | Schutz |
| 2006/0010624 A1 | 1/2006 | Cleland |
| 2006/0021165 A1 | 2/2006 | Boland et al. |
| 2006/0026784 A1 | 2/2006 | Moskovich et al. |
| 2006/0057539 A1 | 3/2006 | Sodo |
| 2006/0078844 A1 | 4/2006 | Goldman et al. |
| 2006/0079818 A1 | 4/2006 | Yande |
| 2007/0082316 A1 | 4/2007 | Zhadanov et al. |
| 2007/0082317 A1 | 4/2007 | Chuang |
| 2007/0113360 A1 | 5/2007 | Tsai |
| 2007/0202459 A1 | 8/2007 | Boyd et al. |
| 2007/0203439 A1 | 8/2007 | Boyd et al. |
| 2007/0254260 A1 | 11/2007 | Alden |
| 2008/0008979 A1 | 1/2008 | Thomas et al. |
| 2008/0189951 A1 | 8/2008 | Molema et al. |
| 2008/0213719 A1 | 9/2008 | Giniger et al. |
| 2008/0253906 A1 | 10/2008 | Strong |
| 2009/0070949 A1 | 3/2009 | Sagel et al. |
| 2009/0082706 A1 | 3/2009 | Shaw |
| 2009/0124945 A1 | 5/2009 | Reich et al. |

(56) References Cited

U.S. PATENT DOCUMENTS

| | | |
|---|---|---|
| 2009/0163839 A1 | 6/2009 | Alexander |
| 2009/0188780 A1 | 7/2009 | Watanabe |
| 2009/0281454 A1 | 11/2009 | Baker et al. |
| 2010/0010524 A1 | 1/2010 | Barrington |
| 2010/0015566 A1 | 1/2010 | Shaw |
| 2010/0190132 A1 | 7/2010 | Taylor et al. |
| 2010/0239998 A1 | 9/2010 | Snyder et al. |
| 2010/0261134 A1 | 10/2010 | Boyd et al. |
| 2010/0261137 A1 | 10/2010 | Boyd et al. |
| 2010/0326536 A1 | 12/2010 | Nan |
| 2010/0330527 A1 | 12/2010 | Boyd et al. |
| 2011/0027749 A1 | 2/2011 | Syed |
| 2011/0076090 A1 | 3/2011 | Wu et al. |
| 2011/0097683 A1 | 4/2011 | Boyd et al. |
| 2011/0139826 A1 | 6/2011 | Hair et al. |
| 2011/0144588 A1 | 6/2011 | Taylor et al. |
| 2011/0184341 A1 | 7/2011 | Baker et al. |
| 2011/0307039 A1 | 12/2011 | Cornell |
| 2012/0021374 A1 | 1/2012 | Cacka et al. |
| 2012/0045730 A1 | 2/2012 | Sayder et al. |
| 2012/0064480 A1 | 3/2012 | Hegemann |
| 2012/0077145 A1 | 3/2012 | Tsurukawa |
| 2012/0141952 A1 | 6/2012 | Snyder et al. |
| 2012/0179118 A1 | 7/2012 | Hair |
| 2012/0189976 A1 | 7/2012 | McDonough et al. |
| 2012/0266396 A1 | 10/2012 | Leung |
| 2012/0277663 A1 | 11/2012 | Millman et al. |
| 2012/0277677 A1 | 11/2012 | Taylor et al. |
| 2012/0277678 A1 | 11/2012 | Taylor et al. |
| 2012/0279002 A1 | 11/2012 | Sokol et al. |
| 2012/0295220 A1 | 11/2012 | Thomas et al. |
| 2013/0295520 A1 | 11/2013 | Hsieh |
| 2014/0106296 A1 | 4/2014 | Woodard et al. |
| 2014/0193774 A1 | 7/2014 | Snyder et al. |
| 2014/0259474 A1 | 9/2014 | Sokol et al. |
| 2014/0272769 A1 | 9/2014 | Luettgen et al. |
| 2014/0272782 A1 | 9/2014 | Luettgen et al. |
| 2014/0352088 A1 | 12/2014 | Wu |
| 2015/0004559 A1 | 1/2015 | Luettgen et al. |

FOREIGN PATENT DOCUMENTS

| | | |
|---|---|---|
| CH | 655237 | 4/1987 |
| CN | 204049908 | 12/2014 |
| DE | 1466963 | 5/1969 |
| DE | 2019003 | 11/1971 |
| DE | 2409752 | 9/1975 |
| DE | 2545936 | 4/1977 |
| DE | 2714876 | 10/1978 |
| DE | 2910982 | 2/1980 |
| DE | 3346651 | 7/1985 |
| EP | 0023672 | 7/1980 |
| EP | 0515983 A1 | 12/1992 |
| EP | 1825827 | 8/2007 |
| FR | 2556954 | 6/1985 |
| FR | 2654627 | 5/1991 |
| GB | 838564 | 6/1960 |
| GB | 1182031 | 2/1970 |
| GB | 2018605 | 10/1979 |
| JP | 2-134150 | 4/1990 |
| JP | 2009-39455 | 2/2009 |
| KR | 20120126265 | 11/2012 |
| WO | WO95/016404 | 6/1995 |
| WO | 01/10327 A1 | 2/2001 |
| WO | WO04/021958 | 3/2004 |
| WO | WO04/039205 | 5/2004 |
| WO | 2004060259 A2 | 7/2004 |
| WO | WO2004/062518 | 7/2004 |
| WO | WO2008/070730 | 6/2008 |
| WO | 2008157585 A1 | 12/2008 |
| WO | 2013124691 A1 | 8/2013 |

OTHER PUBLICATIONS

The Right Tool, Electron Fusion Devices, Inc., 2 pages, at least as early as Feb. 1991.

Japanese Packaging, 2 pages, at least as early as Dec. 2002.

Japanese Instruction Brochure, 20 pages, at least as early as Dec. 2002.

Brochure: Woog International, "You have a 98% chance of getting gum disease. Unless you read this.", Lancaster, Pennsylvania, 5 pages, Feb. 1987.

Brochure: Woog International, "We put the control of home dental care back into the hands of the professional", Lancaster, Pennsylvania, 2 pages, Feb. 1987.

Brochure: WOOG International, "Products at a Glance: Home Dental Care System" WOOG Orajet, 3 pages, at least as early as Dec. 18, 1998.

Website: http://www.just4teeth.com/product/Panasonic/Panasonic_Portable_Irrigator.htm, 2 pages, at least as early as Jun. 20, 2003.

Website: http://www.videodirectstore.com/store/merchant.mv?Screen=PROD&Product_Code=EW1' . . . , 2 pages, at least as early as Jun. 20, 2003.

Website: http://products.consumerguide.com/cp/family/review/index.cfm/id/18742, 2 pages, at least as early as Jun. 20, 2003.

Website: http://www.racekarteng.com/images/walbroparts.gif and http://www.muller.net/mullermachine/docs/walbro1.html, 4 pages, at least as early as Jun. 20, 2003.

European Search Report, EPO Application No. 07250799.9, dated Jul. 5, 2007.

European Search Report, EPO Application No. 07252693.2, 14 pages, dated Apr. 28, 2008.

European Examination Report, EPO Application No. 07250799.9, dated Feb. 5, 2009.

International Search Report, Application No. PCT/US2010/028180, 2 pages, dated May 18, 2010.

International Search Report, PCT/US2010/060800, 2 pages, dated Feb. 11, 2011.

International Search Report, PCT/US2011/052795, 10 pages, dated Jan. 17, 2012.

Waterpik SinuSense Website: http://www.insightsbyapril.com/2012/03/waterpik-natural-remedy-for-sinus.html, 8 pages, retrieved on May 31, 2012.

Waterpik WP 350W Oral Irrigator. Dentist.net. Copyright date 2013. Date accessed: Mar. 30, 2017, 2 pages <http://www.dentalhoo.com/waterpik-wp350.asp>.

iPik Portable Oral Irrigator. AliExpress. Date reviewed: Oct. 5, 2016. <https://www.allexpress.com/ . . . e-Oral-Care-Product-Nasal-Irrigator-Tooth-Flosser-Water/1525541997.html?aff_platform=aaf&cpt=1490913714609&sk=yfAeyJa&aff_trace_key=c5a300c4f02e46d08c042f5292e1762f-1490913714609-07517-ytAeyJa>, 18 pages.

Brite Leafs Professional Portable 2-in-1 Nasal Sinus & Oral Irrigator. Brite Leafs. Copyright date 2012, <http://www.briteleafs.com/product6.html>, 1 page.

AliExpress. Date reviewed: Jan. 12, 2017. <https://www.aliexpress.com/item/Cordless-Water-Floss-Portable-Oral-Irrigator-Dental-Water-Flosser-Waterpic-Whatpick-Dental-Water-Pic-Whater-Pick/32769416341.html?spm=2114.40010308.4.75.Owuzfj>.

* cited by examiner

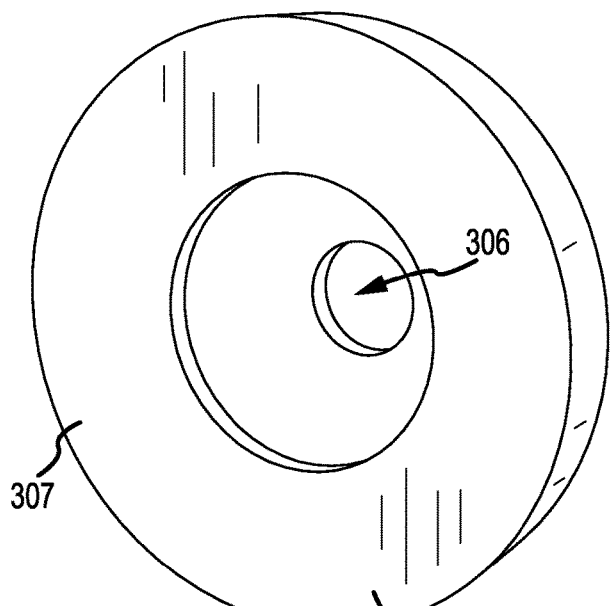
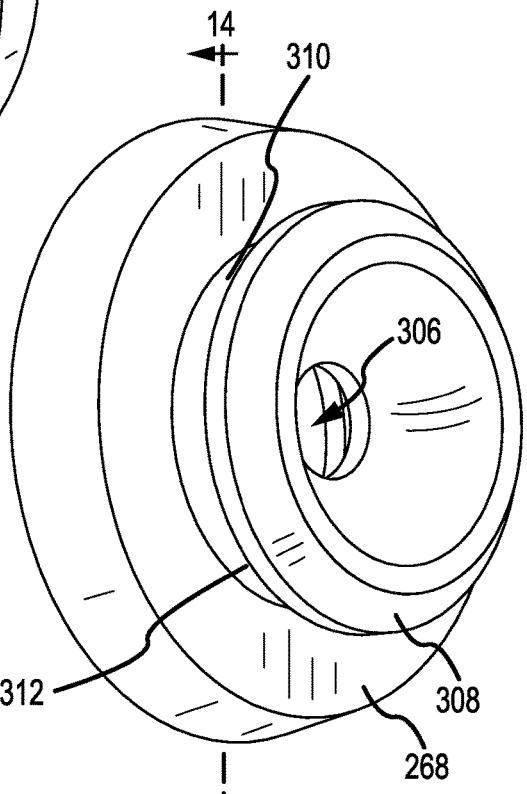
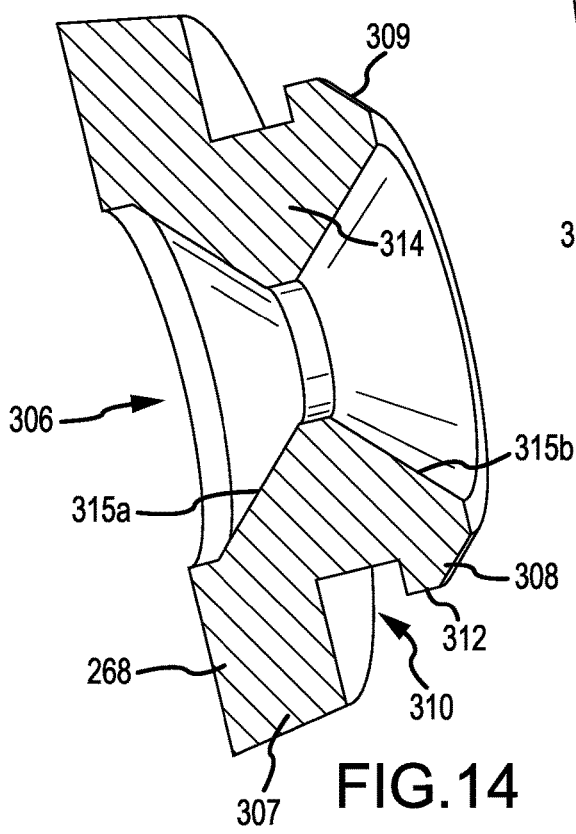
FIG.13A
FIG.13B
FIG.14

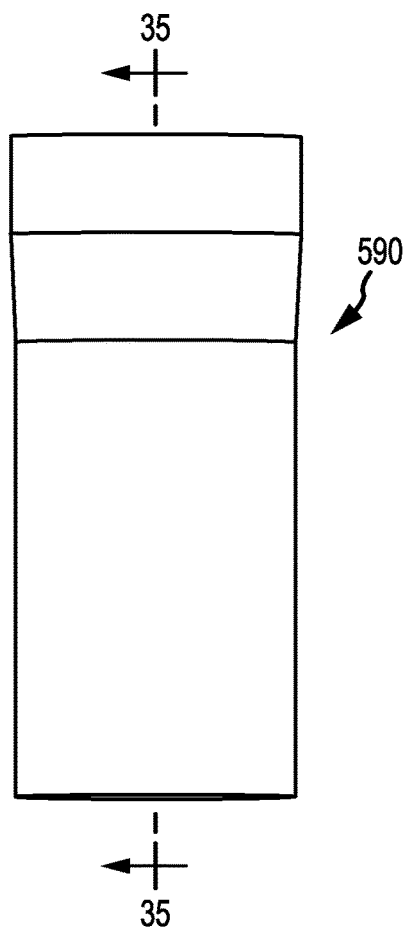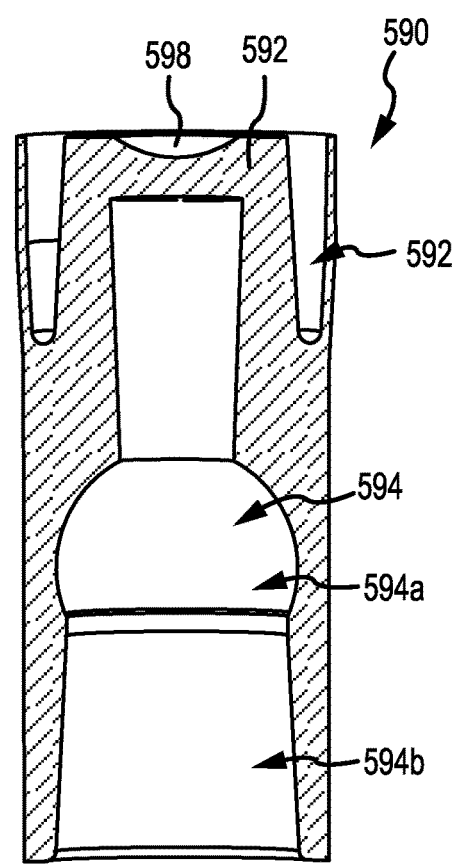
FIG.34
FIG.35

INTERDENTAL CLEANER USING WATER SUPPLY

CROSS REFERENCE TO RELATED APPLICATIONS

This application claims the benefit of priority pursuant to 35 U.S.C. § 119(e) of U.S. provisional application No. 61/712,771 entitled "Interdental Cleaner Using Water Supply," filed 11 Oct. 2012, the disclosure of which is hereby incorporated herein by reference in its entirety.

TECHNICAL FIELD

The technology described herein relates generally to interdental cleaners, such as water flossers or oral irrigators, and more particularly to interdental cleaners fluidly connected to an external fluid source, such as a showerhead water supply.

BACKGROUND

Interdental cleaners, such as water flossers, are generally used be people to clean their teeth and gums. Typically, water flossers provide a stream of water that may be aimed towards the user's mouth, and the user may direct the water stream through a tip. Generally, water flossers include a water supply, such as a reservoir or tank attached to a base or a reservoir within the water flosser body itself (e.g., a handheld water flosser). In either of these configurations, a user generally must refill the reservoir by either removing the reservoir from the base or the irrigator body and filling it with a water supply. Depending on how frequently the water flosser is used, a person may have to refill the reservoir often. Additionally, many water flossers may occupy space on a user's countertop, which may be undesirable for some users.

The information included in this Background section of the specification, including any references cited herein and any description or discussion thereof, is included for technical reference purposes only and is not to be regarded subject matter by which the scope of the invention is defined in the claims is to be bound.

SUMMARY

Some embodiments may include an interdental cleaner for operably connecting to an external water supply. The interdental cleaner may include a mounting bracket fluidly connected to the external water supply and a pressure regulation assembly operably and fluidly connected to the mounting bracket. The interdental cleaner may further include a water flosser operably connected to the mounting bracket and fluidly connected to a fluid outlet of the pressure regulation assembly. The pressure regulation assembly reduces a water pressure from the external water supply.

Other embodiments may include a showerhead mount in fluid communication with a fluid source. The showerhead mount includes a bracket housing having an inlet, at least one outlet, and a showerhead support configured to operably connect to a showerhead. The showerhead mount further includes a pressure regulation assembly that reduces a water pressure of water traveling between the inlet and one outlet of the at least one outlet.

Some other embodiments include a water flosser. The water flosser includes a switch movable between an office position and at least one on position, a power source in electrical communication with the switch, a drive assembly in communication with the switch, and a valve assembly operably connected to the switch, the valve assembly including a pressure control valve. During use, movement of the switch from the off position to the at least one on position mechanically moves the pressure control valve from a valve off position to a first valve on position and provides electrical communication between the power source and the drive assembly and movement of the switch from the at least one on position to the off position mechanically moves the pressure control valve to the valve off position and disables electrical communication between the drive assembly and the power source.

Yet other embodiments of the disclosure include an irrigating unit. The irrigating unit includes a mounting bracket configured to operably connect to a water supply, a pressure regulator fluidly connected to the mounting bracket, and an oral irrigator fluidly connected to the pressure regulator and operably connected to the mounting bracket. The pressure regulator controls a water pressure of a water flow from the water supply to the oral irrigator.

Other embodiments include an interdental cleaning unit. The unit includes a showerhead having a showerhead inlet in fluid communication with a water supply and a water flosser operably connected to the showerhead. The water flosser includes a flosser inlet fluidly connected to the water supply. In the unit, the water pressure at the showerhead inlet is different from the water pressure at the flosser inlet.

Still other embodiments include a battery pack for a handheld device. The battery back includes a battery case defining a battery cavity configured to receive at least one batter. The battery pack further includes at least one electrical contact in communication with the battery housing and a stabilizing detent operably connected to the battery housing.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments of the invention and illustrated in the accompanying drawings.

BRIEF DESCRIPTION OF THE DRAWINGS

FIG. 13A is a rear isometric view of a poppet seat of the pressure regulator assembly.

FIG. 13B is a front isometric view of the poppet seat.

FIG. 14 is a cross-section view of the poppet seat taken along line 14-14 in FIG. 13B.

FIG. 34 is a front elevation view of a shuttle for the water flosser.

FIG. 35 is a cross-section view of the shuttle taken along line 35-35 in FIG. 34.

DETAILED DESCRIPTION

Various examples of an oral irrigator, water flosser, or interdental cleaner fluidly connected to a water supply for a showerhead are described herein. In one example, a water flosser assembly may include a mounting bracket, water flosser, and a showerhead or showerhead attachment member. The mounting bracket may be operably connected to a water supply pipe (such as a J pipe) extending from a support wall and may provide water from the supply pipe to the water flosser as well as to a showerhead (e.g., either a wall mount or handheld showerhead). Additionally, the bracket may provide a mounting structure, such as a cradle, for either or both the showerhead and the water flosser. This may allow the water flosser and the showerhead to share the same water source, and may allow a user to use the water flosser while taking a shower, which may provide for increased efficiency and convenience.

In some implementations, the mounting bracket, showerhead, and/or water flosser may include a pressure regulator. For example, the mounting bracket may also function as a pressure regulator to reduce the water pressure of water from the supply source prior to providing the water to the water flosser. In this example, the water flosser may use a pump to provide a controlled fluid flow to a tip and, because of the pressure regulation in the bracket, the pump mechanism may be better able to control the pressure and velocity of the water as it exits the water flosser. In alternate embodiments, such a pressure regulator could reside in the showerhead or in the water flosser itself.

In addition to the pressure control within the bracket, the water flosser itself may include one or more flow regulating mechanisms. In one example, the water flosser may include a pressure selection mechanism to provide two outlet water pressures. In this exemplary embodiment, the water flosser may vary the fluid path or paths of water from the bracket to the tip of the water flosser, which may vary the fluid pressure at the fluid outlet. The different fluid paths within the water flosser may allow for a less complicated, single-speed motor to be used to drive a pump to provide varying outlet water pressures.

Figure 1A:
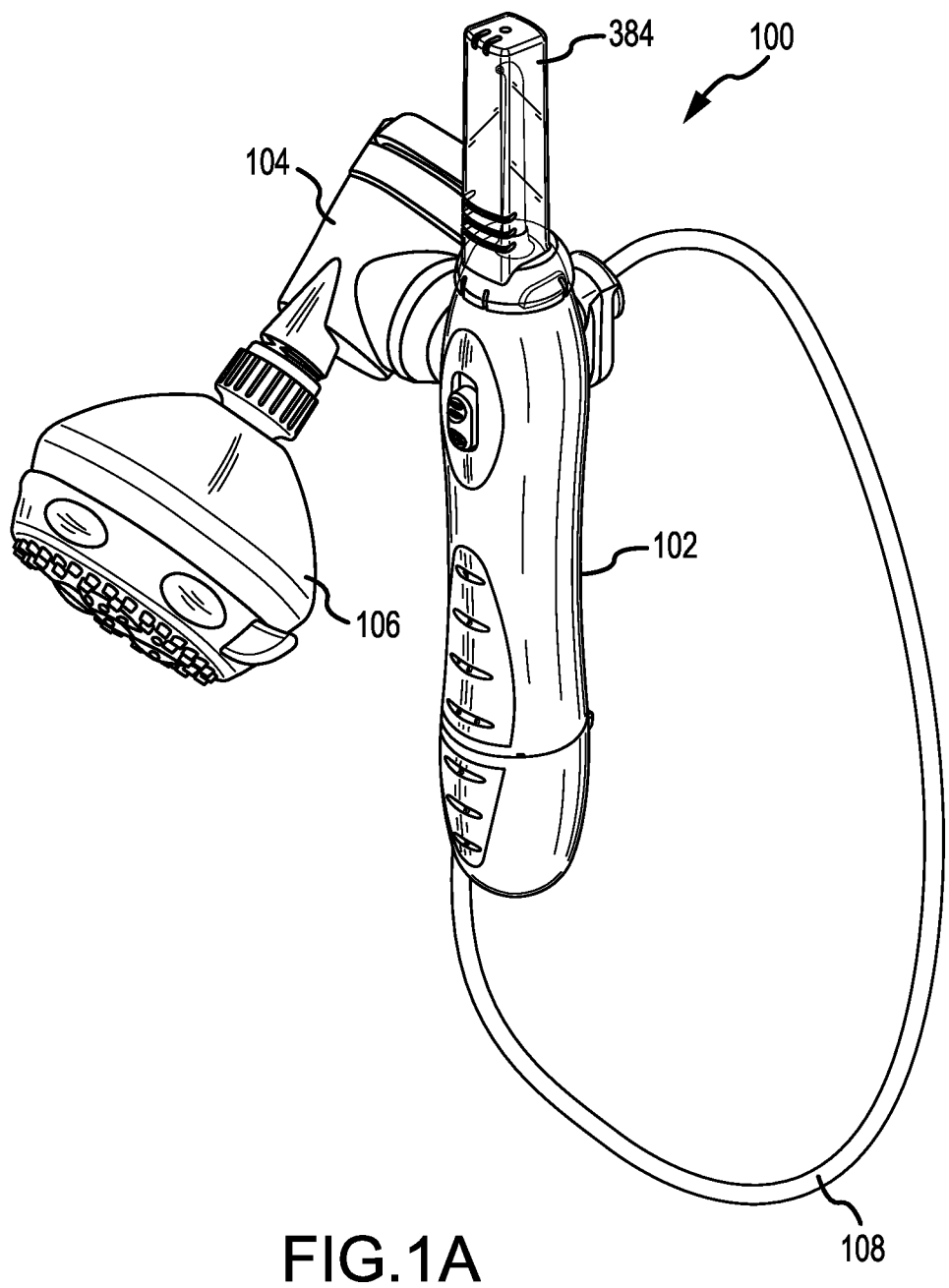
FIG. 1A is a front isometric view of an irrigating unit including a mounting bracket, a water flosser, and a showerhead.
Figure 1B:
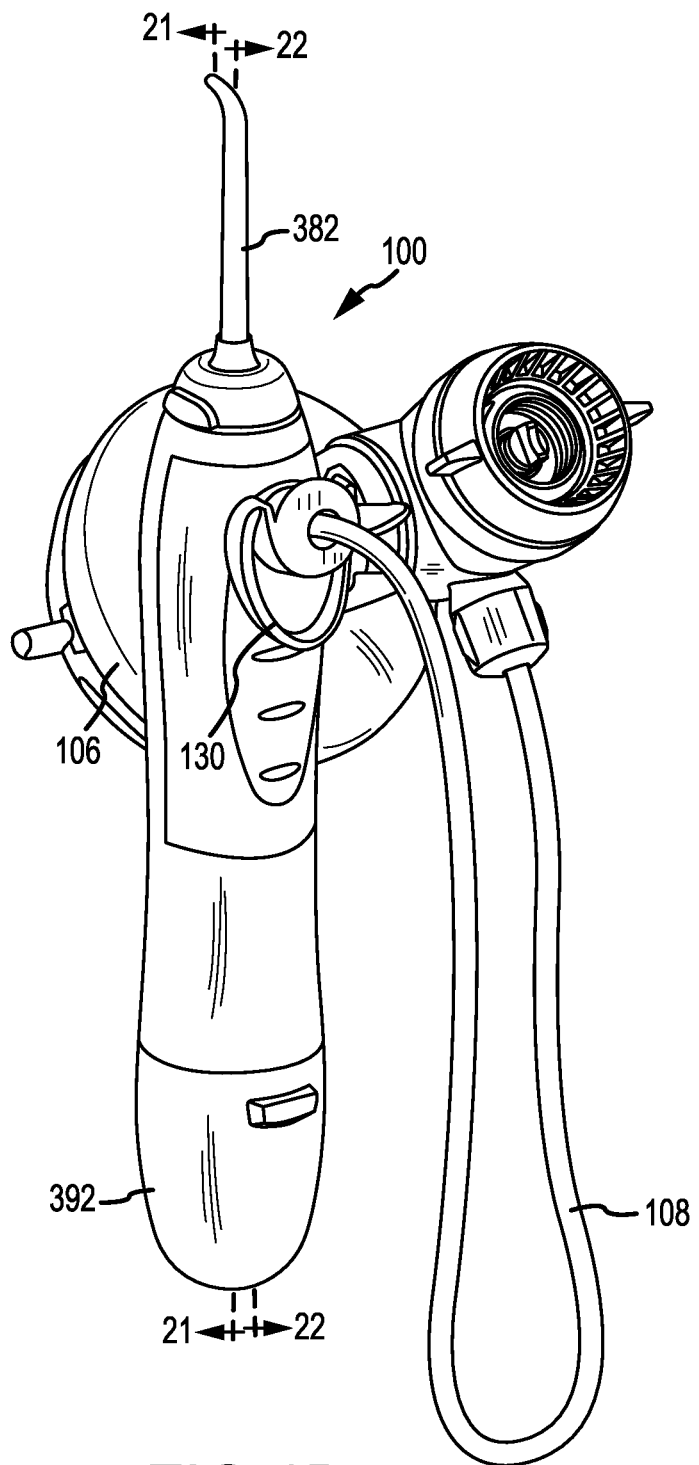
FIG. 1B is a rear isometric view of the irrigating unit of FIG. 1A.

The water flosser, bracket, and showerhead will now be discussed in more detail. FIG. 1A is a side isometric view of the irrigating unit 100. FIG. 1B is a rear isometric view of the irrigating unit 100. With reference to FIGS. 1A and 1B, the irrigating unit 100 may include a mounting bracket 104 that may be fluidly connected to a water supply pipe (not shown), such as a J-pipe. The mounting bracket 104 may be operably and fluidly connected to a water flosser 102 and a showerhead 106.

The showerhead 106 may be operably connected to the mounting bracket 104 and may be in direct fluid communication with the mounting bracket 104 (e.g., a wall mount showerhead) or may be in fluid communication with the mounting bracket through a hose (e.g., a handheld showerhead). In some instances, the mounting bracket may provide an attachment portion to provide a connection for a showerhead, such as a wall mount showerhead. Additionally, the mounting bracket may provide a mount support for the water flosser, such as by including a cradle for the water flosser to be positioned within. In these embodiments, the mounting bracket 104 may provide a support structure for either or both the showerhead and the water flosser 102, as well as be positioned between a water source and the showerhead 106 and water flosser 102. As will be discussed in more detail below, the mounting bracket 104 may also include a flow regulation component to regulate the water pressure from the water source.

The Mounting Bracket Assembly

The mounting bracket assembly for fluidly connecting the water flosser 102 and the showerhead 106 to a water supply source will now be discussed in more detail. With brief reference to FIG. 1A, it should be noted that in some embodiments, the mounting bracket 104 may be mounted on the water supply so that it may be angled downwards. In this manner, in instances when the showerhead 106 is a mounted showerhead, the water flow from the nozzles of the showerhead 106 may be directed downwards at an angle towards a user. However, depending on the desired showerhead, such as a "rain-fall" or handheld showerhead, the mounting bracket 104 may be configured to extend in other orientations.

Figure 3A:
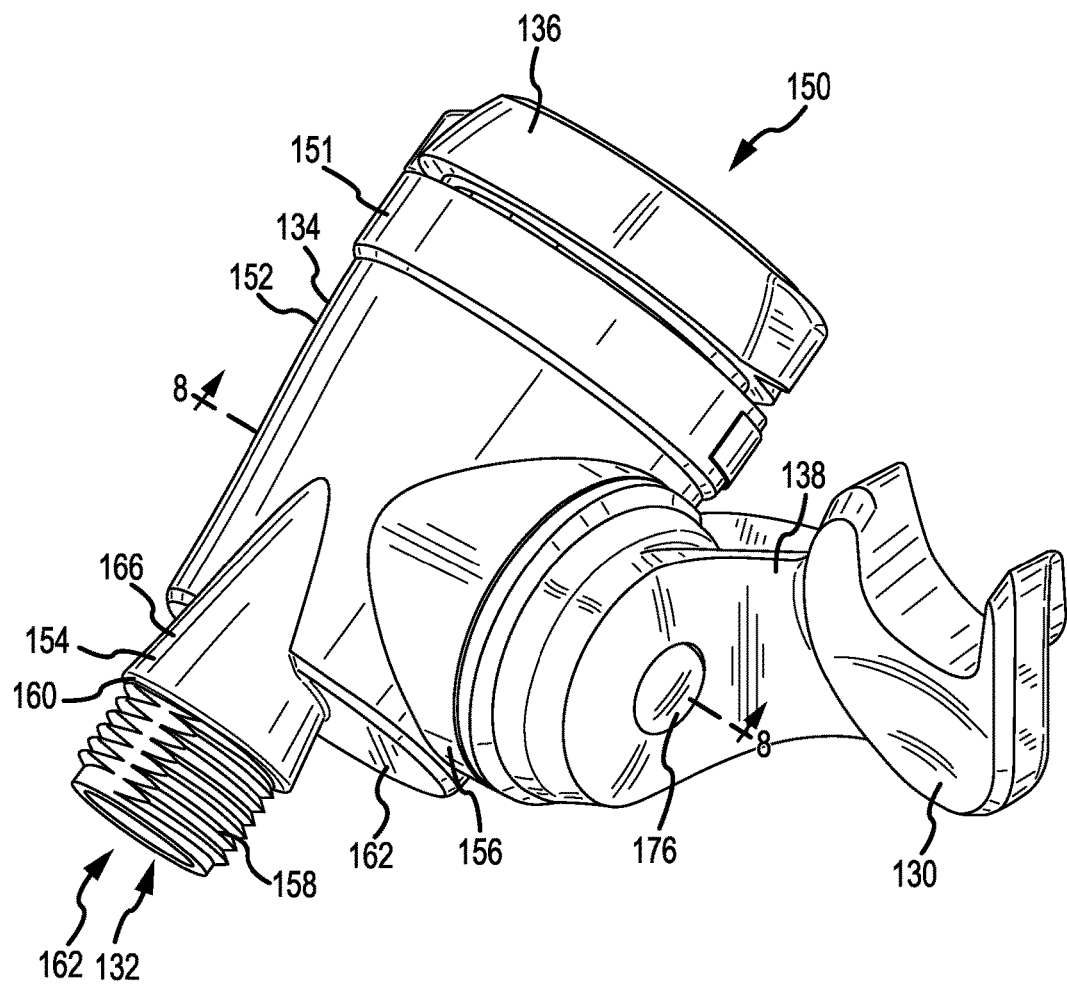
FIG. 3A is a right side isometric view of the mounting bracket for the irrigating unit.
Figure 3B:
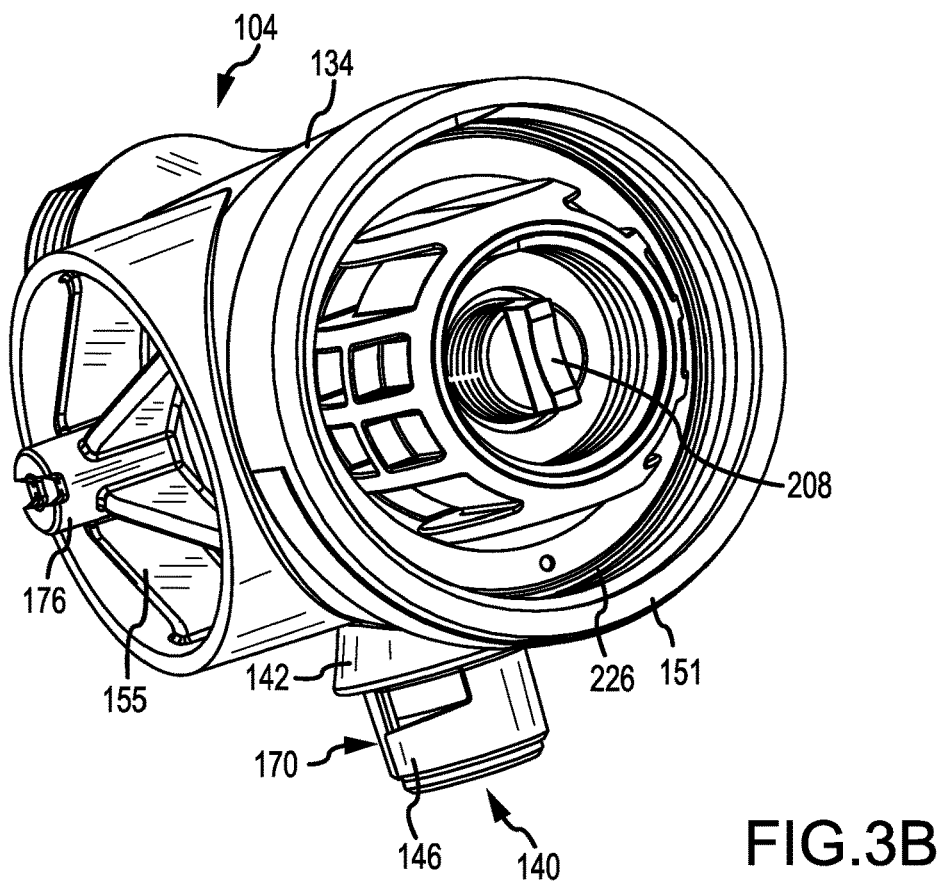
FIG. 3B is a rear-right side isometric view of the mounting bracket for the irrigating unit.
Figure 3C:
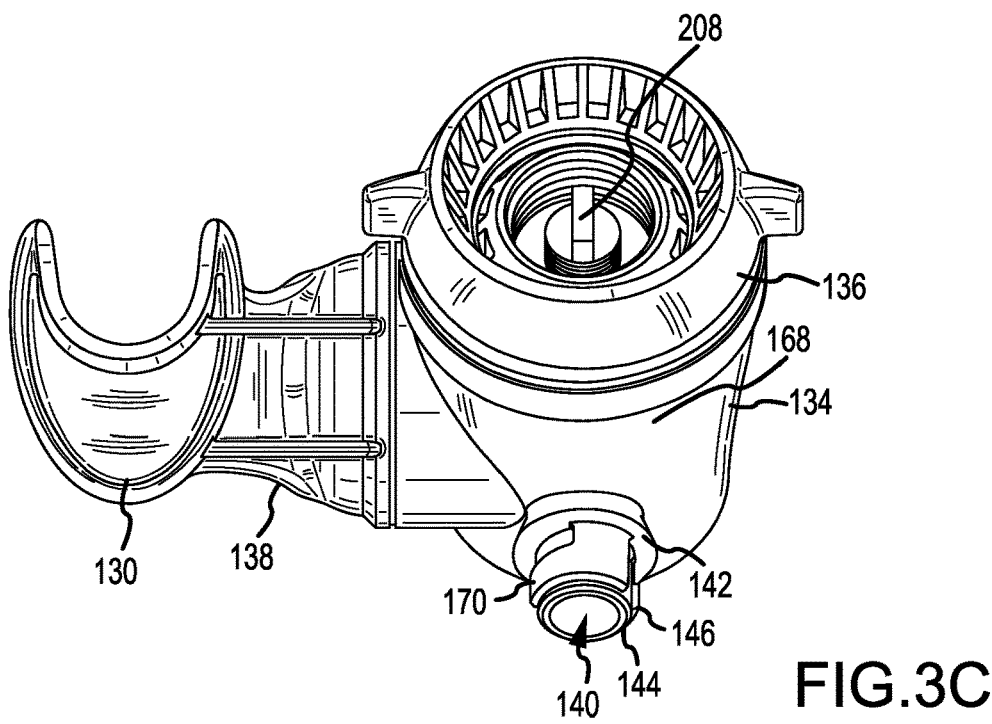
FIG. 3C is a bottom isometric view of the mounting bracket.
Figure 3D:
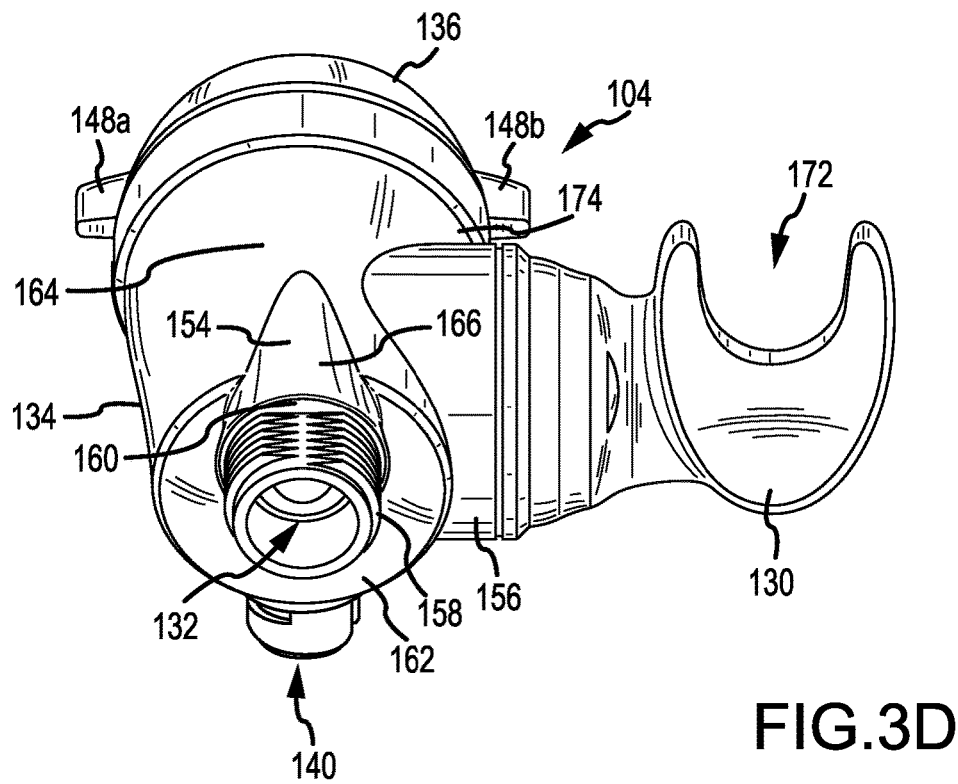
FIG. 3D is a front isometric view of the mounting bracket.

FIGS. 3A-3E are various isometric views of the mounting bracket 104. FIG. 4 is an exploded view of the mounting bracket. With reference to FIGS. 3A-4, the mounting bracket 104 may include a bracket housing 134, which may house a pressure regulator assembly 204 and a water supply assembly 206. The mounting bracket 104 may further be operably connected to the cradle 130. The water supply assembly 206 may operably connect the mounting bracket 104 to the water supply pipe (not shown), as well as filter water as it flows from the water supply pipe through the mounting bracket 104. In an exemplary implementation, the water supply assembly 206 may include a pivot ball 220 that may be operably connected to a water supply pipe, a coupling collar 136 that may secure the pivot ball 220 within the bracket housing 134, and a pivot seat 210 for supporting the pivot ball 220. Additionally, the water supply assembly 206 may include one or more O-rings 212, 214, a rubber washer 216, 218 for providing sealing and securing features for the elements of the water supply assembly 206. The water supply assembly 206 may also include a basket filter 208 for filtering large particulate from the water as it enters into the mounting bracket 104 and travels therethrough.

It should be noted that the elements of the water supply assembly 206, specifically, the connection and filtering components may be adjusted as desired. For example, in implementations where a handheld showerhead 106 may be connected to the mounting bracket 104, the pivot ball 220 may be omitted as the mounting bracket 104 may not need to be pivoted relative to the water supply pipe. As another example, various other types of filters may be used in replace of the filter 208 or, in instances where water filtering may not be desired, the water filter 208 may be omitted.

Bracket Housing

Figure 5A:
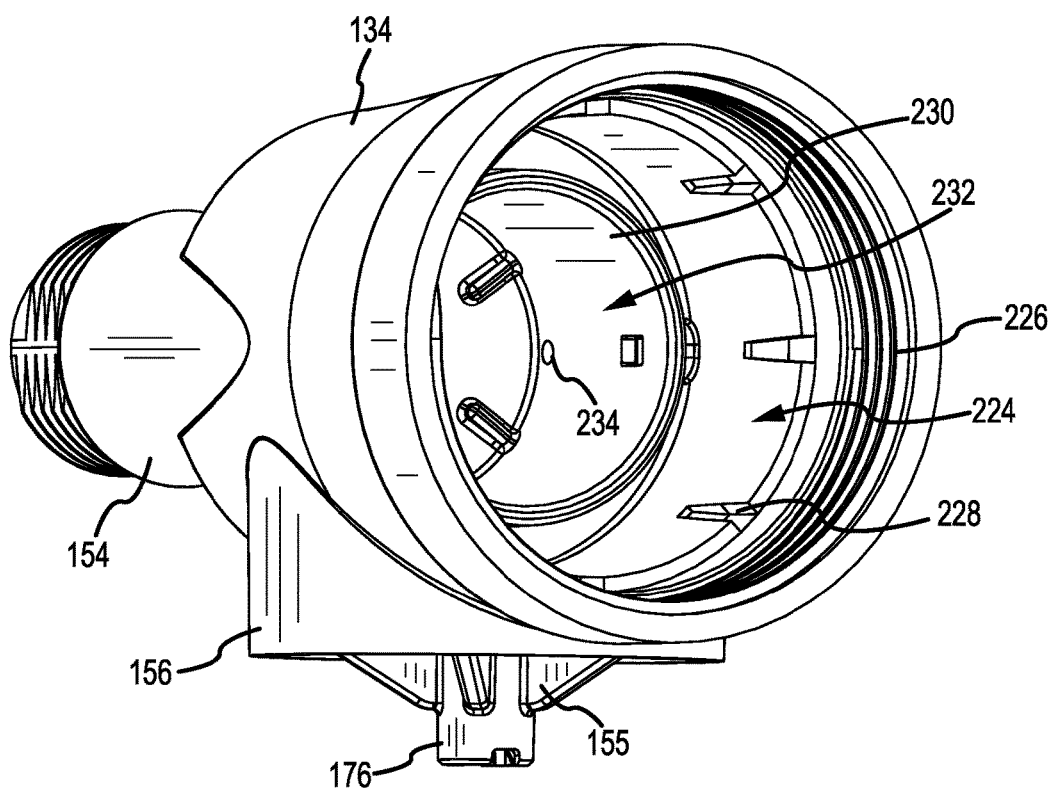
FIG. 5A is a rear-right isometric view of a bracket housing of the mounting bracket.
Figure 5B:
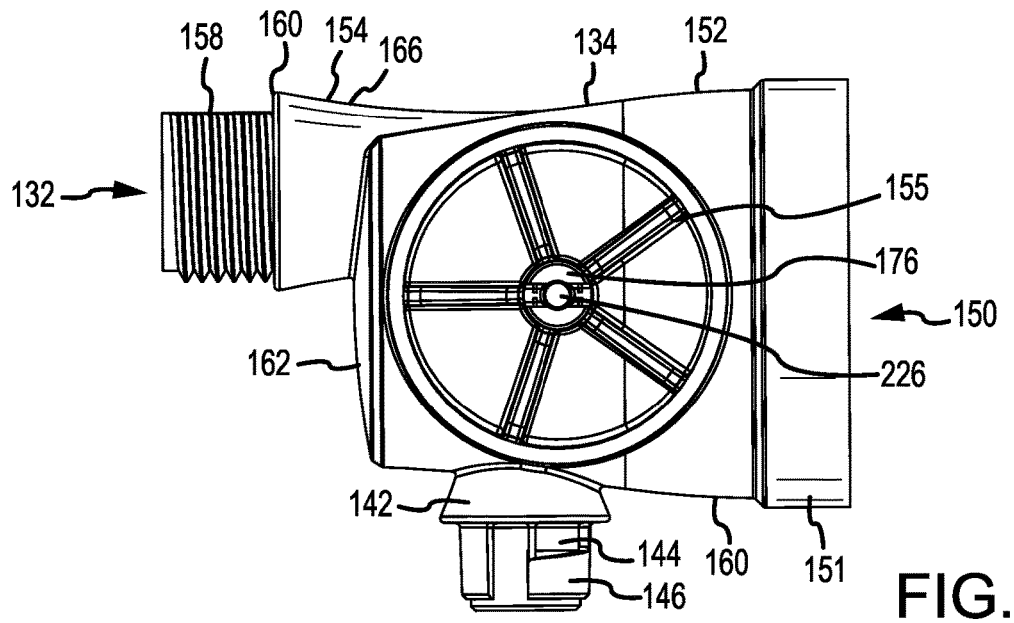
FIG. 5B is a right elevation view of the bracket housing.
Figure 5C:
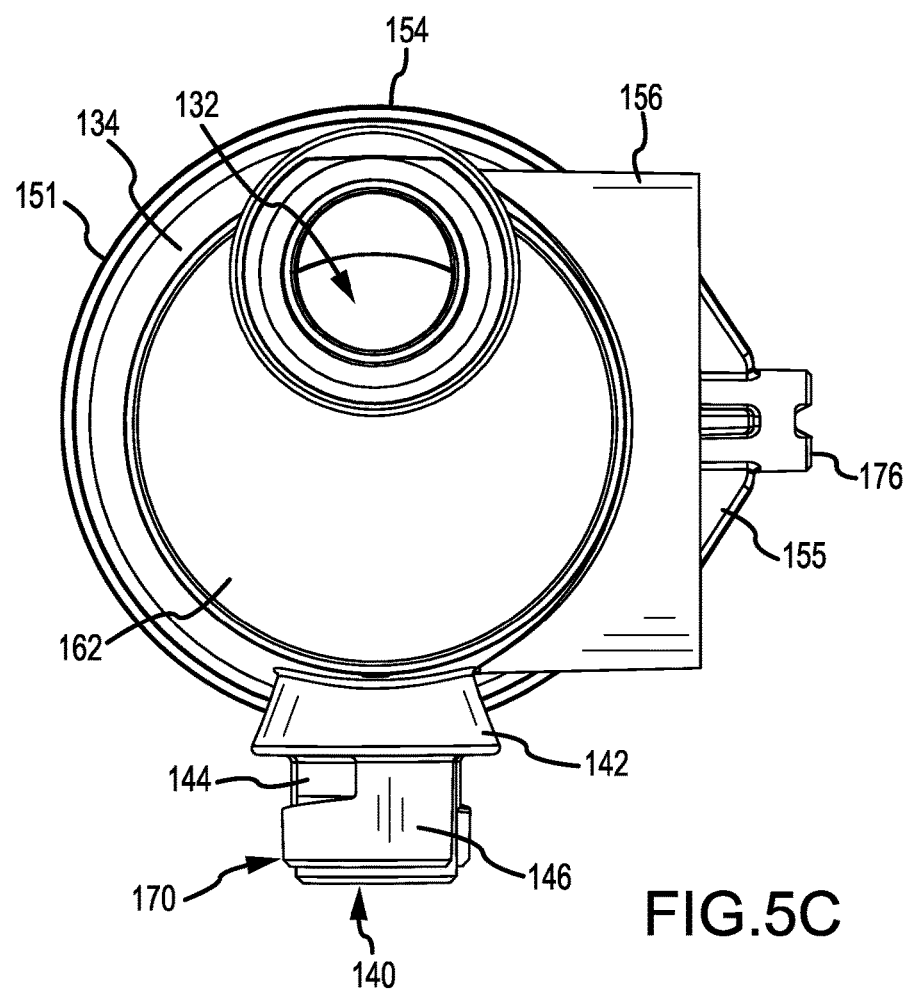
FIG. 5C is a front elevation view of the bracket housing.

The bracket housing 134 will now be discussed in more detail. FIG. 5A is a rear isometric view of the bracket housing 134. FIG. 5B is a side elevation view of the bracket housing 134. FIG. 5C is a front elevation view of the bracket housing 134. The bracket housing 134 may define a bracket cavity 224 that may receive the pressure regulator assembly 204 and the water flow assembly 206. The bracket housing 134 may include a main body 152, a water flosser support 156 extending from one side of the main body 152, and a showerhead extension 154 extending from a front side of the main body 152.

The bracket housing 134 may include a generally rounded, frustum-shaped main body 152 that may gradually decrease in diameter from the inlet port 150 towards the showerhead outlet port 132. The rear side of the main body 152 may be open to the bracket cavity 224 to allow for the water flow assembly 206 and the pressure regulator assembly 204 to be positioned within the bracket cavity 224.

A receiving collar 151 may form the terminal end of the main body 152 and may interface with the coupling collar 136 of the water flow assembly 206. Additionally, the interior surface of the receiving collar 151 at the proximal end 224 may include receiving threads 226 into which the coupling collar 136 is screwed. The internal walls of the bracket housing 134 defining the cavity 24 may define one or more attachment slots 228, which may be keyed features that interface with a number of angularly dispersed fins 211 on the distal side of the pivot seat 210, which interface prevents the pivot seat from rotating within the water flow assembly 206.

The bracket housing 134 may include an inlet port 150 (i.e., the water flow assembly 206), a showerhead outlet port 132, and a water flosser outlet port 140. The inlet port 150 may be fluidly connected to the two outlet ports 132, 140, with the showerhead outlet port 132 providing water flow to the showerhead 106 and the water flosser outlet port 140 providing water flow to the water flosser 102. The inlet port 150 and the outlet ports 136, 140 may be defined within the bracket housing 134. Each of the outlet ports 132, 140 may be in fluid communication with the bracket cavity 224.

Figure 3E:
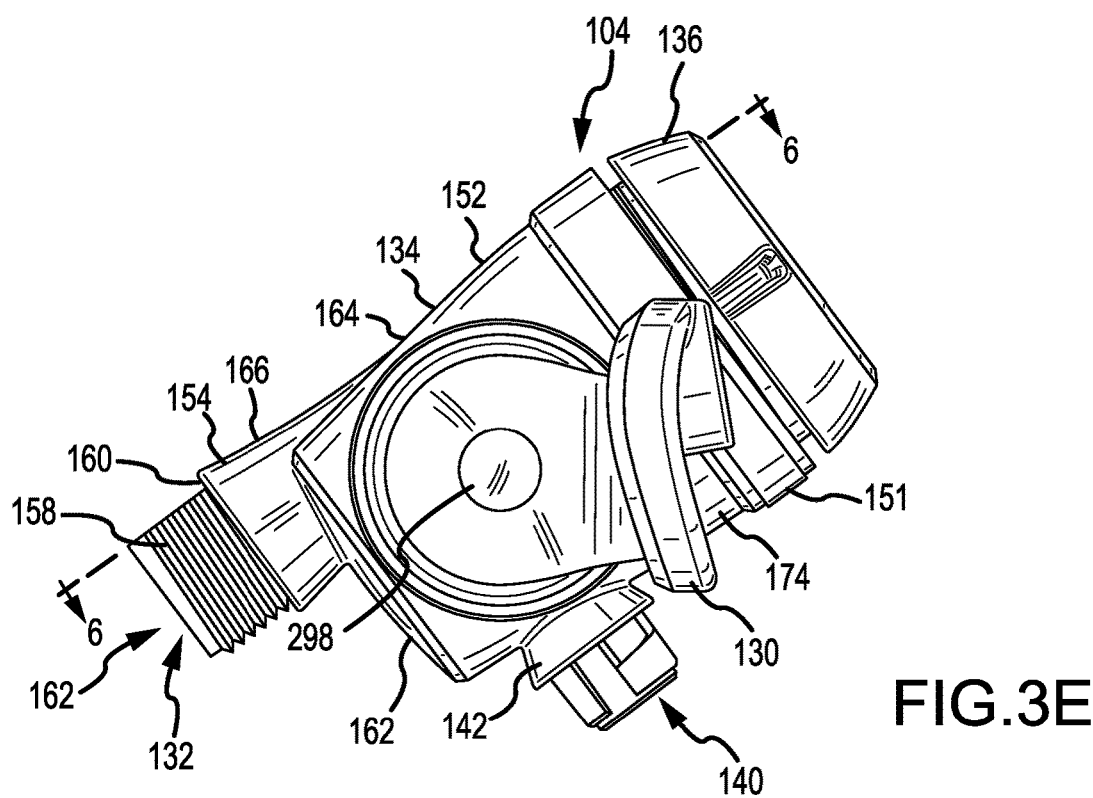
FIG. 3E is a right elevation view of the mounting bracket.
Figure 4:
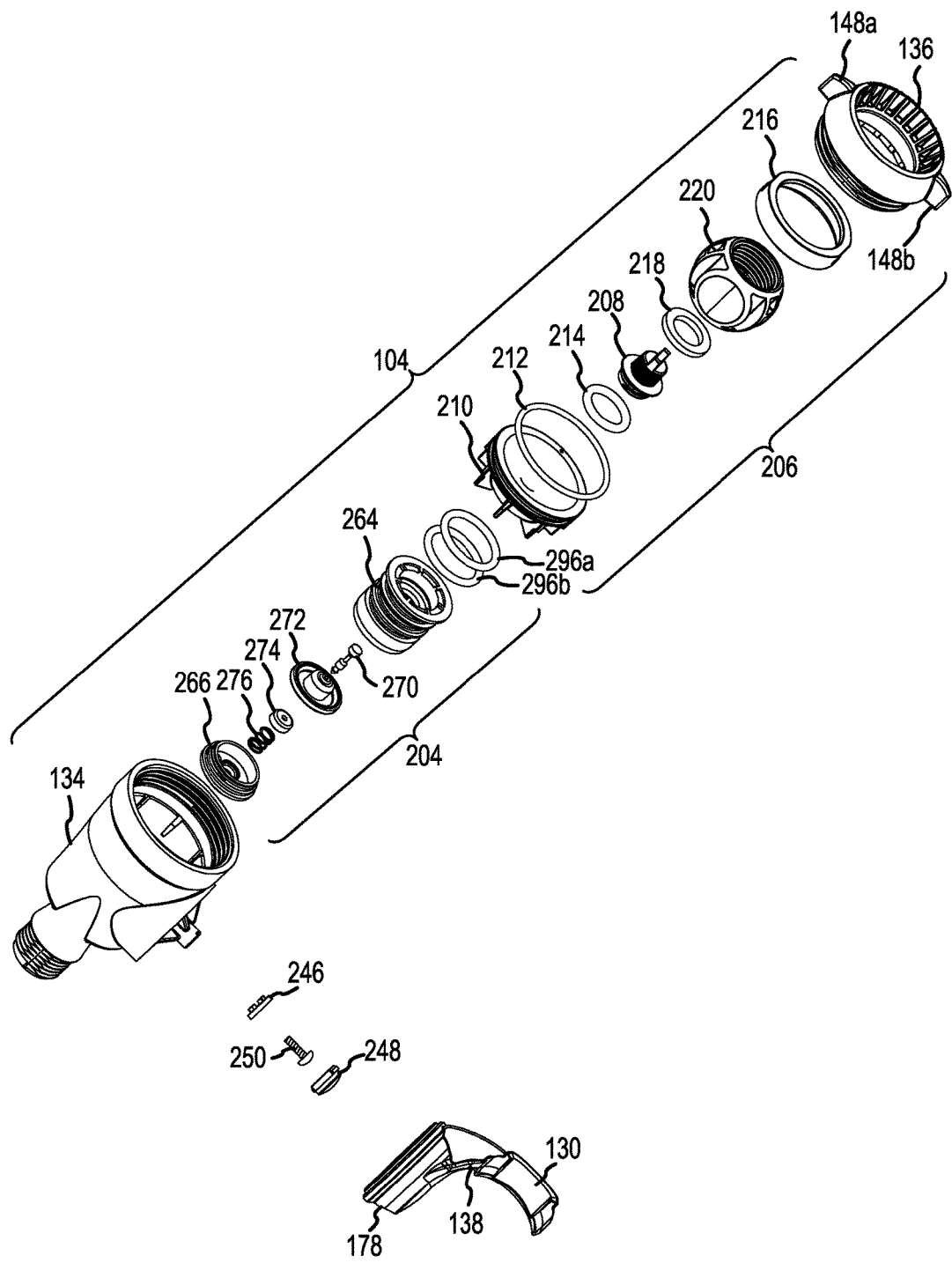
FIG. 4 is an exploded view of the mounting bracket.
Figure 6:
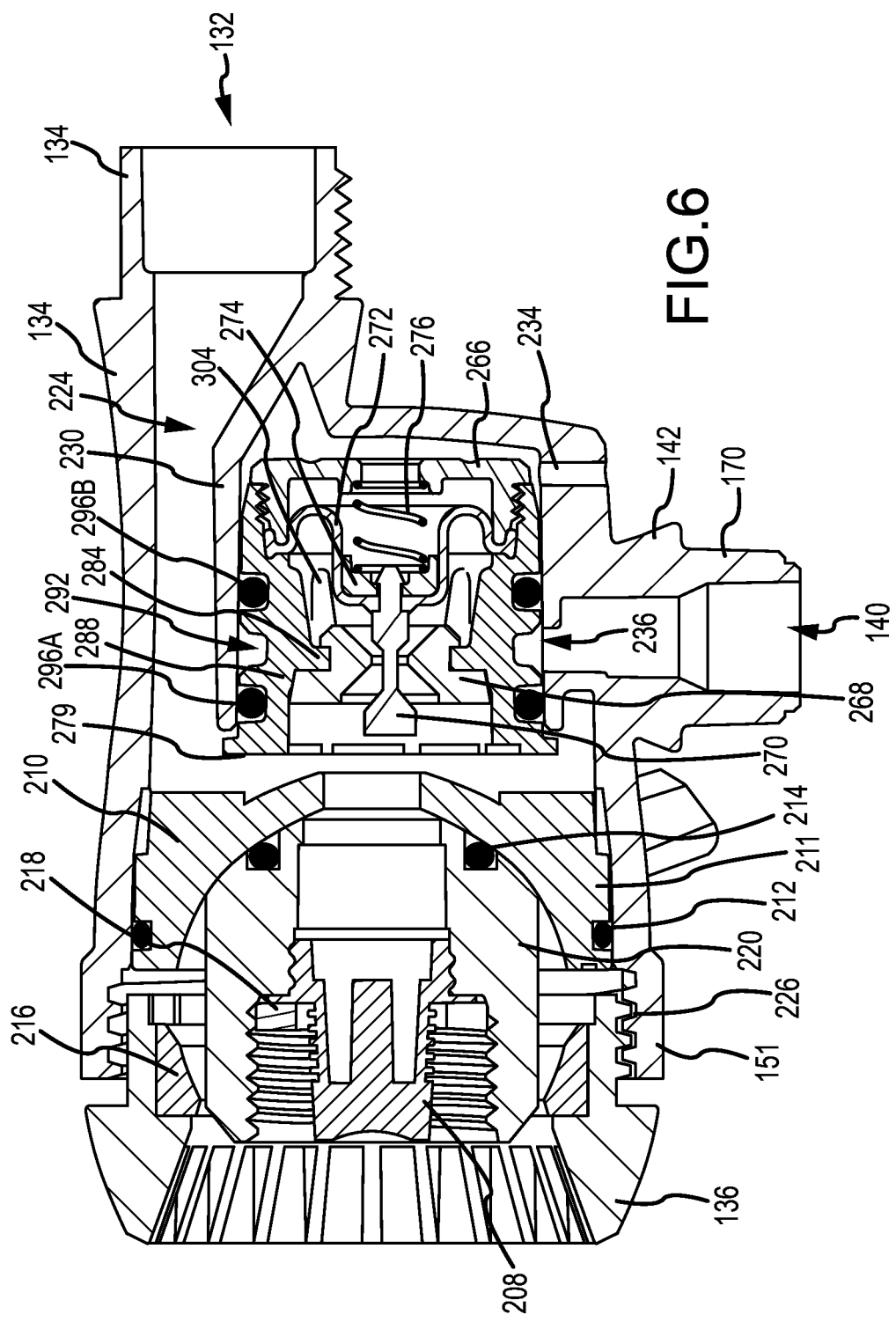
FIG. 6 is a cross-section view of the mounting bracket taken along line 6-6 in FIG. 3E.

FIG. 6 is a cross-section view of the mounting bracket 104 taken along line 6-6 in FIG. 3E. With reference to FIGS. 5A and 6, the bracket housing 134 may include a pressure regulator housing portion 230 that defines a pressure regulation cavity 232. The pressure regulator housing portion 230 receives the pressure regulator assembly 204 and also acts to separate fluid flowing between the pressure regulator assembly 204 and the showerhead outlet port 132 (as discussed in more detail below).

The pressure regulator housing portion 230 may extend distally from the water supply assembly 206 to form the distal end 162 of the bracket housing 134. An interior surface of the pressure regulator housing portion 230 may be positioned above an interior bottom surface of the main body 152 or may form a portion of the bottom surface. The pressure regulator housing portion 230 may be generally shaped as a cylindrical wall to define a portion of the bracket cavity 224; however, the shape of the pressure regulator housing portion 230 may be varied based on the configuration of the pressure regulator assembly 204.

The pressure regulator housing portion 230 may define a weep hole 234 and an irrigator flow aperture 236. The weep hole 234 may be defined in the pressure regulator housing portion 230 through the outer surface of the main body 152 and thus may be in communication with the outer environment. The irrigator flow aperture 236 may be defined in the pressure regulator housing portion 230 and be in fluid communication with a water flosser outlet port 140 extending from an outer surface of the bracket housing 134. Thus, the irrigator flow aperture 236 may allow fluid to flow from the bracket housing 134 to the water flosser 102 via the water flosser outlet port 140.

The showerhead extension 154 may extend from a top portion of a distal end 162 of the main body 152. In some embodiments, the showerhead extension 154 may extend upward as well as outward from the main body 152, in these instances at least a top surface 166 of the showerhead extension 154 may be elevated over a top surface 164 of the main body 152. However, in other embodiments, the showerhead extension 154 may extend from any other surface of the bracket housing 134 as desired for effectively positioning the showerhead 106.

The showerhead extension 154 may have a generally cylindrical shape and may include a plurality of threads 158 defined on an outer surface. The threads 158 may be recessed from the outer surface of the showerhead extension 154 to define a lip 160 at the transition point of the threads 158. The lip 160 may provide a continuous transition from the showerhead 106 to the mounting bracket 104 when the showerhead 106 is operably connected to the bracket. The showerhead outlet port 132 may be defined through the showerhead extension 154 and may be fluidly connected to the bracket cavity 224 defined within the main body 152 of the bracket housing 134.

The main body 152 of the bracket housing 134 may further include a water flosser coupling 170 extending from a bottom surface 168. The water flosser coupling 170 may be operably connected to the hose 108 to provide water to the water flosser 102. The water flosser port 140 may be defined through the water flosser coupling 170 and may be fluidly connected to the bracket cavity 224 defined within the bracket housing 134. The water flosser coupling 170 may be a generally cylindrical connection member, and may include one or more connection or securing features. For example, a connection feature 146 and a connection groove 144 may be defined in an outer surface of the irrigator coupling 170. The connection feature 146 and the connection groove 144 may help to align and secure the hose 108. In one exemplary embodiment, the hose 108 may include one or more corresponding alignment features which may be aligned with the connection feature 146 and connection groove 144.

In one exemplary embodiment, the connection feature 146 may be defined as a raised, backward "L"-shaped surface that wraps around the outer surface of the connection feature 146. For example, a first portion may extend vertically along one side of the irrigator coupling 170 and a second portion may wrap around the circumference (or portion thereof) of the outer surface. The connection groove 144 may be defined as the channel or groove providing relief to form the raised portions of the connection feature 146 in the outer surface of the irrigator coupling 170.

A top portion of the irrigator coupling 170 may expand outward to form a collar 142 that extends from the bottom surface 168 of the main body 152. The collar 142 may be generally frustum shaped and may expand outward as it transitions away from the bottom surface 168. The irrigator coupling 170 may be narrower in diameter than a bottom edge of the collar 142, so that irrigator coupling 170 may be somewhat mushroom shaped, with the collar 142 forming the cap of the "mushroom."

With continued reference to FIGS. 3A-3E, the mounting bracket 104 may further include a water flosser support 156 extending from one side of the main body 152 of the bracket housing 134. The water flosser support 156 may be a generally cylindrically shaped member that extends outwardly away from a first side 174 of the main body 152. The water flosser support 156 operably connects with and supports the cradle arm 138, which, in turn, supports the water flosser 102. The water flosser support 156 may be a generally hollow cylindrical body formed by an outer wall 157 that may define an internal cavity that receives a portion of the cradle arm 138, as discussed in more detail below.

Figure 8:
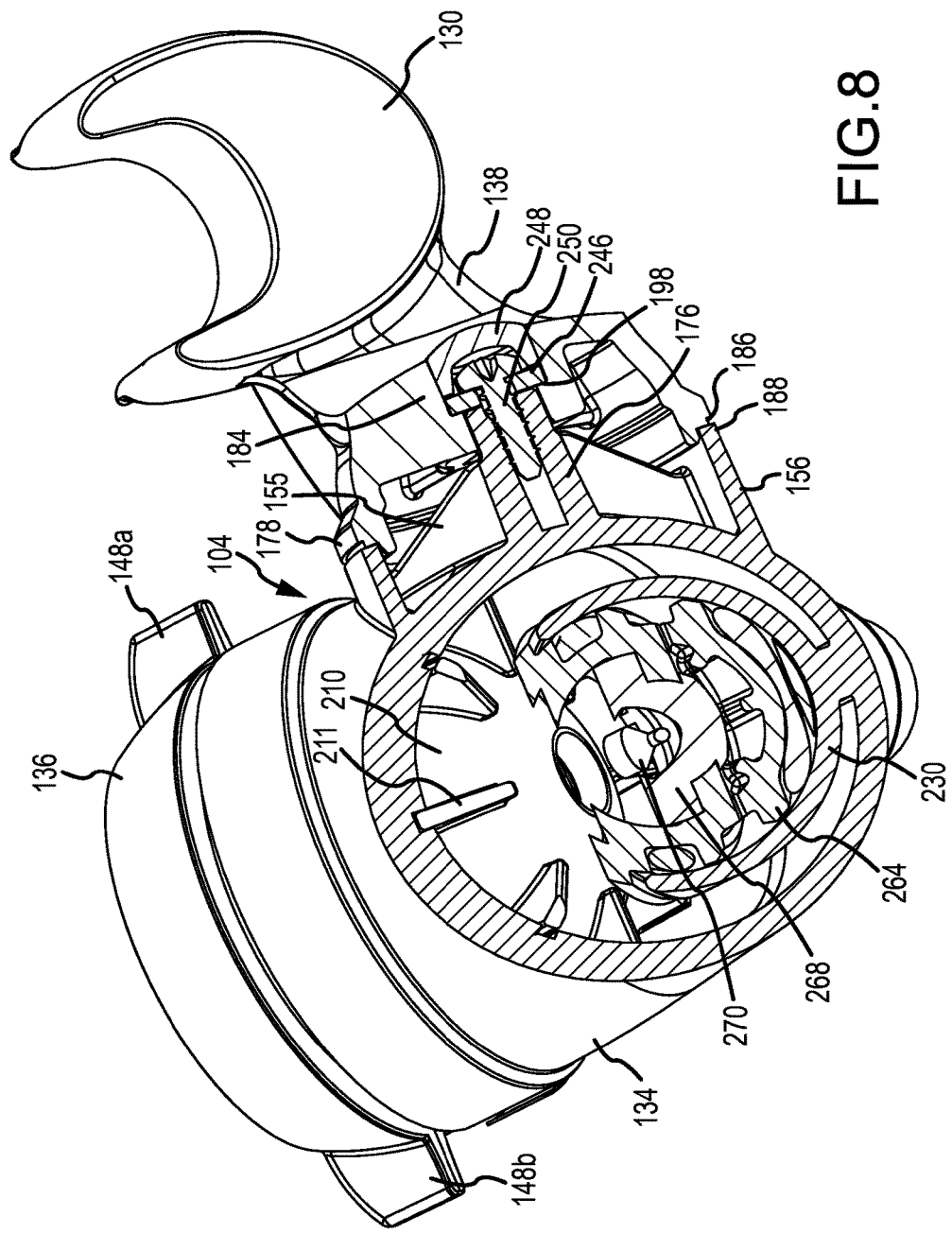
FIG. 8 is a cross-section view of the bracket assembly taken along line 8-8 in FIG. 3A.

In some embodiments, with reference to FIGS. 5A, 5B, and 8, the water flosser support 156 may also include a connection post 176 positioned within the outer wall 157 of to the water flosser support 156. The connection post 176 may be supported by one or more bracing walls 155 that may extend radially from the connection post 176 to the first side 174 of the main body 152.

The connection post 176, which may be a hollow, cylindrically shaped extension, configured to receive or otherwise interact with one or more fasteners within a bore 159 which may secure the cradle arm 138 to the bracket housing 134. For example, the inner wall of the connection post 176 forming the bore 159 may be threaded in order to receive a screw or other similar fastener. In some instances, the connection post 176 may extend farther outward from the main body 152 than outer wall 157 of the water flosser support 156. However, it should be noted that the configuration of the water flosser support 156 and connection post 176 may be varied based on the desired connection, as well as configuration, of the cradle arm 138. A top end of the connection post 176 may include a channel or indentations 226 on opposite sides of the aperture. The indentations 226 may be horizontally oriented and may receive a nut, discussed in more detail below with respect to the cradle 130.

Cradle for Water Flosser

Figure 7A:
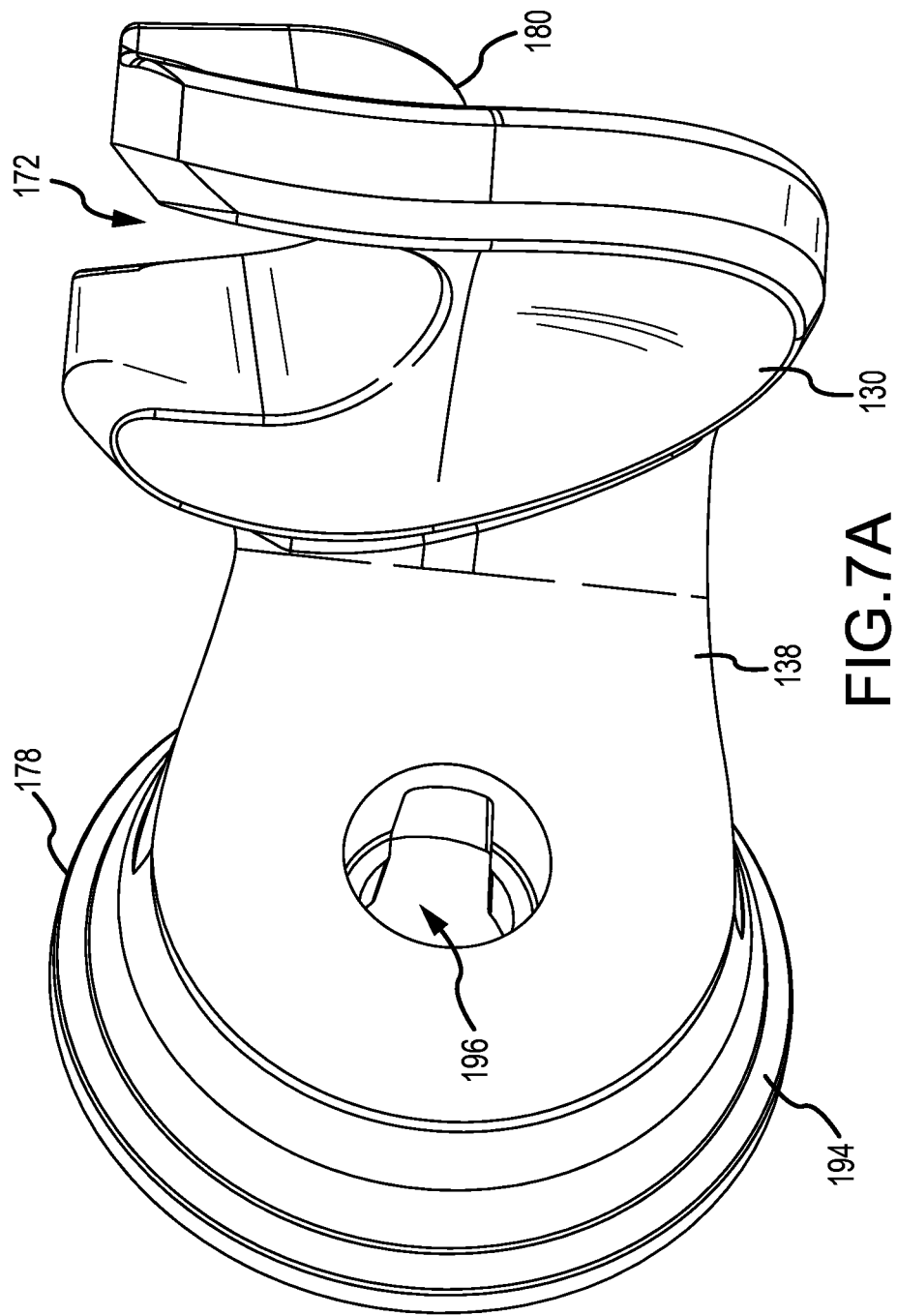
FIG. 7A is a front isometric view of a cradle assembly for operably connecting the oral irrigator to the mounting bracket.
Figure 7B:
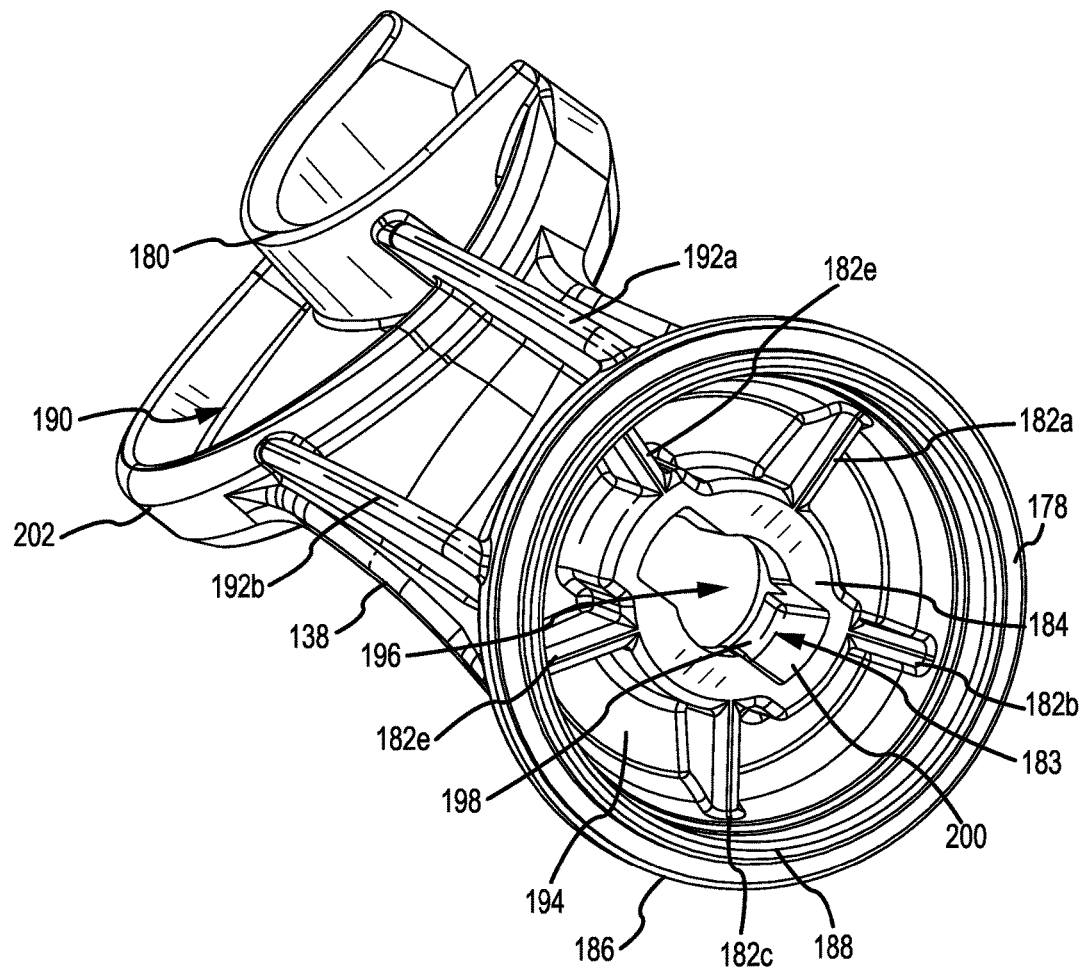
FIG. 7B is a rear isometric view of the cradle assembly.

The cradle assembly for the water flosser will now be discussed in more detail. FIG. 7A is a front isometric view of the cradle assembly. FIG. 7B is a side-rear isometric view of the cradle assembly. With reference to FIGS. 3C, 7A, and 7B, the cradle 130 extends from the cradle arm 138, which is operably connected to the bracket housing 134. A first end of the cradle arm 138 includes an arm base 178 configured to be operably connected to the water flosser support 156. The arm base 178 may be generally cylindrically shaped and may extend outward away from the cradle arm 138 to define an engagement flange 186. The engagement flange 186 may be configured to interface with an outer end surface of the water flosser support 156.

The arm base 178 may also define a base cap 194 formed on an opposite side of the arm base 178 from the engagement flange 186. The base cap 194 may form an end cap for the arm base 178. With reference to FIG. 7B, a connection boss 184 may extend from or an inner surface a center point of the base cap 194. A plurality of support ribs 182a, 182b, 182c, 182d, 182e may extend outward from the connection boss 184 on the inner surface of the base cap 194 towards the engagement flange 186. The support ribs 182a, 182b, 182c, 182d, 182e may be radially oriented outward from the center of the base cap 194. A receiving aperture 183 may be defined through the connection boss 184 and base cap 194, which may reduce the strength of the connection boss 184. The support ribs 182a, 182b, 182c, 182d, 182e may thereby provide support to the connection boss 184 and the base cap 194.

The dimensions of the receiving aperture 183 may vary from the first end defined through the outer surface of the base cap 194 to the outer surface of the connection boss 184 within the arm base 178. In some embodiments, the receiving aperture 183 in the connection boss 184 may include a recessed key or geometric shape. For example, with reference to FIG. 7B, the receiving aperture 183 be formed with a pair of recessed tabs or wings 200 that extend outward from a circular center. A portion of the wings 200 may decline part of the receiving aperture 183 through the base cap 194 on lateral sides of the circular center 196. The lateral ends of the wings 200 may be defined by a seat 198 that is a portion of the inner surface of the base cap 194 facing the engagement flange 186. The receiving aperture 183 thus transitions from a smaller winged opening from the first side of the base cap 194 to a laterally winged opening defined within the connection boss 184.

With continued reference to FIG. 7B, the arm base 178 may further include an annular engagement lip 188. The engagement lip 188 may extend normally from a surface of the engagement flange 186 and may have a smaller diameter than an outer diameter of the engagement flange 186. The engagement lip 188 may be sized and configured to fit within and adjacent to the outer wall 157 of the water flosser support 156 and the bracket housing 134. The engagement flange 186 may be cooperatively sized and configured to interface with the top surface of the outer wall 157 of the water flosser support 156 on the bracket housing 134.

With reference to FIGS. 7A and 7B, the cradle arm 138 may extend away from the arm base 178 in the form of a convex curve toward the cradle 130 such that the cradle 130 is oriented substantially perpendicular to the base cap 194. In one embodiment, as shown in FIGS. 3A and 7A, the cradle arm 138 may be curved to partially surround the body of the water flosser 102 when the water flosser 102 is operably connected to the cradle 130.

As shown in FIG. 7B, the cradle arm 138 may be reinforced by one or more braces 192a, 192b that may provide structural support for the arm 138. The braces 192a, 192b may extend along the length of the cradle arm 138 between the arm base 178 and the cradle 130. The braces 192a, 192b may also allow the cradle arm 138 to be formed using less material, as the braces 192a, 192b may provide sufficient support for the arm to help support the water flosser 102.

A second end of the cradle arm 138 may terminate at the cradle 130. The cradle 130 may be a generally "U"-shaped body that may define a cradle rest 172 and a hose support 180. When not in use, the water flosser 102 may generally be stored within the cradle rest 172. The hose support 180 may extend outward from a back surface of the cradle 130 to form a horseshoe shape. An outer rim 202 may be formed on a backside of the cradle 130 that traces along the perimeter of the cradle 130. Additionally, with reference to FIG. 7B, a recessed portion 190 that extends from a bottom end of the cradle 130 towards the hose support 180 may be defined by the outer rim 202.

The arm base 178 of the cradle arm 138 may be operably connected to the bracket housing 134 by an adjustment assembly. FIG. 8 is a cross-section view of the bracket assembly taken along line 8-8 in FIG. 3A. With reference to FIGS. 4 and 8, the adjustment assembly may include a bearing washer 246, a fastener 250, and/or a plug 248. The fastener 250 may be substantially any type of fastening device, such as, but not limited to, a screw, bolt, rivet, pin, or the like. The fastener 250 may be received into the bore 159 defined by the connection post 176 on the water flosser support 156 of the bracket housing 134. The plug 248 may be a cup-shaped member that may be seated over the head or end of the fastener 250. The plug 248 may conceal the fastener 250 to help reduce fastener's exposure to water which, in instances where the fastener 250 is metal or the like, may help to prevent the fastener from rusting. Additionally, the plug 248 may conceal the fastener to provide an improved aesthetic appearance for the mounting bracket 104.

Figure 9A:
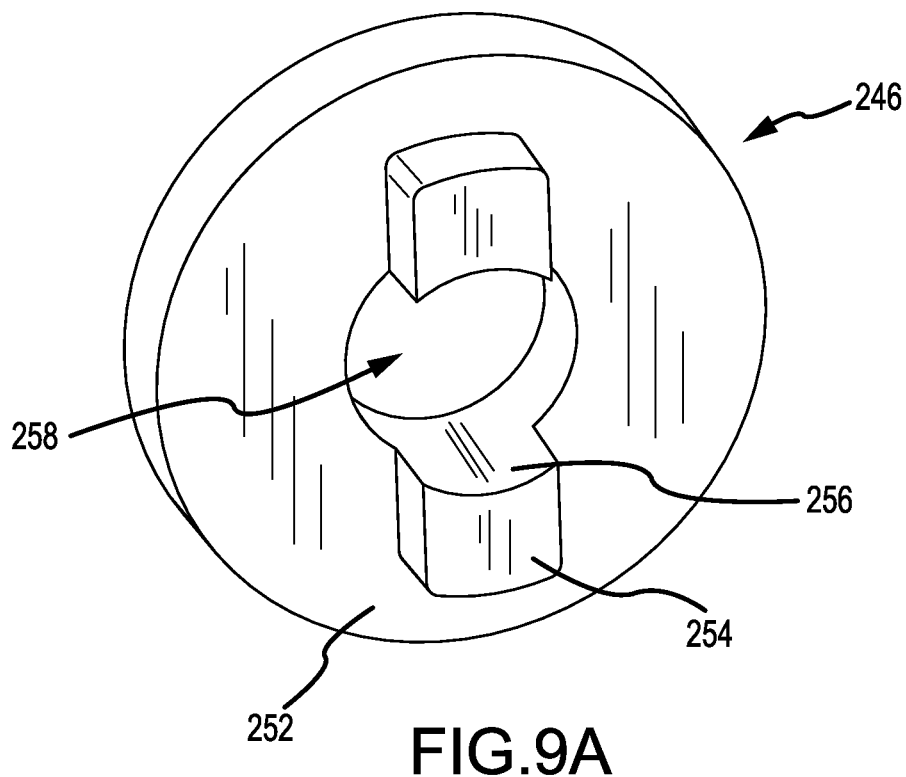
FIG. 9A is a rear isometric view of a bearing washer.
Figure 9B:
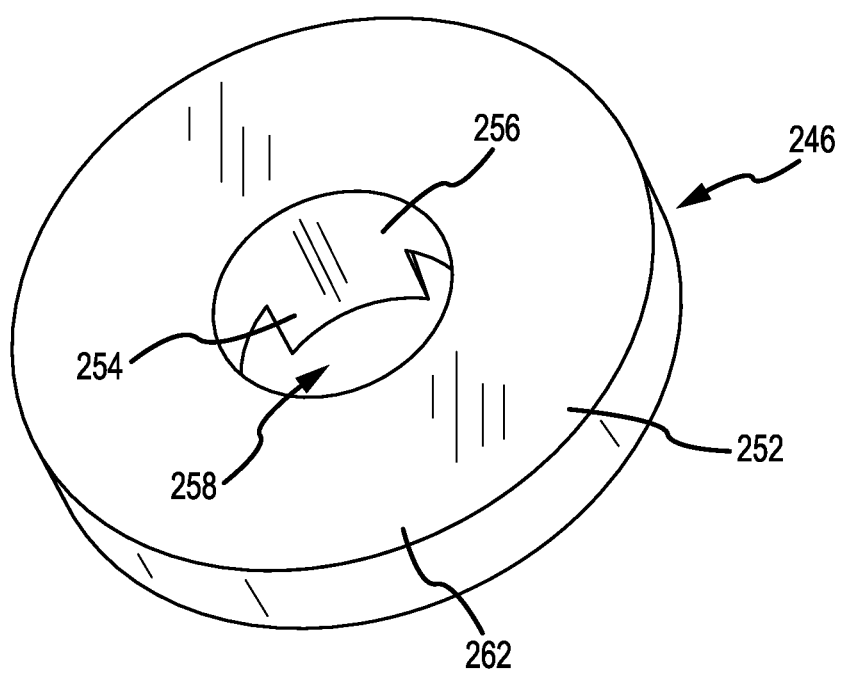
FIG. 9B is a front isometric view of the bearing washer.

The bearing washer 246 may allow the cradle 130 and cradle arm 138 to be rotated relative to the bracket housing 134, while still providing sufficient stiffness in the connection between the arm and housing to allow the arm 138 to remain in position. FIG. 9A is a rear isometric view of the bearing washer 246. FIG. 9B is a front isometric view of the bearing washer 246. With reference to FIGS. 8, 9A, and 9B, the bearing washer 246 may have a washer body 252 that may be an annular disk defining a circularly shaped washer aperture 258 defined through a center thereof. A first side 262 of the washer body 252 may be substantially planar, whereas a second side 260 of the washer body 252 may include two raised tabs 254 that extend upward from a planar surface thereof.

The tabs 254 may be positioned on opposing sides of the washer aperture 258 and may have a generally rectangular configuration. However, each tab 254 may have a curved or rounded inner wall 256 facing and abutting the washer aperture 258. The rounded inner walls 256 of each tab 254 may have generally the same radius of curvature as the washer aperture 258. In this manner, when the fastener 250 is received in the washer aperture 258, the fastener may be flanked on two sides by the tabs 254, with the rounded walls 256 curving around the fastener 250. The lateral ends of each of the tabs 254 opposite the washer aperture 258 extend only partially across the width of the annular disk forming the washer body 252 and do not extend as far as an outer circumference of the washer body 252.

With reference to FIGS. 8, 9A, and 9B, the bearing washer 246 seats on a recessed surface of the connection post 176 and is received between a bottom surface of the head of the fastener 248 and the connection post 176. The tabs 254 fit into recesses in the connection post 176 so that the bearing washer 246 sits relatively flat on top of the connection post 176.

Flow Regulator Assembly

Figure 10:
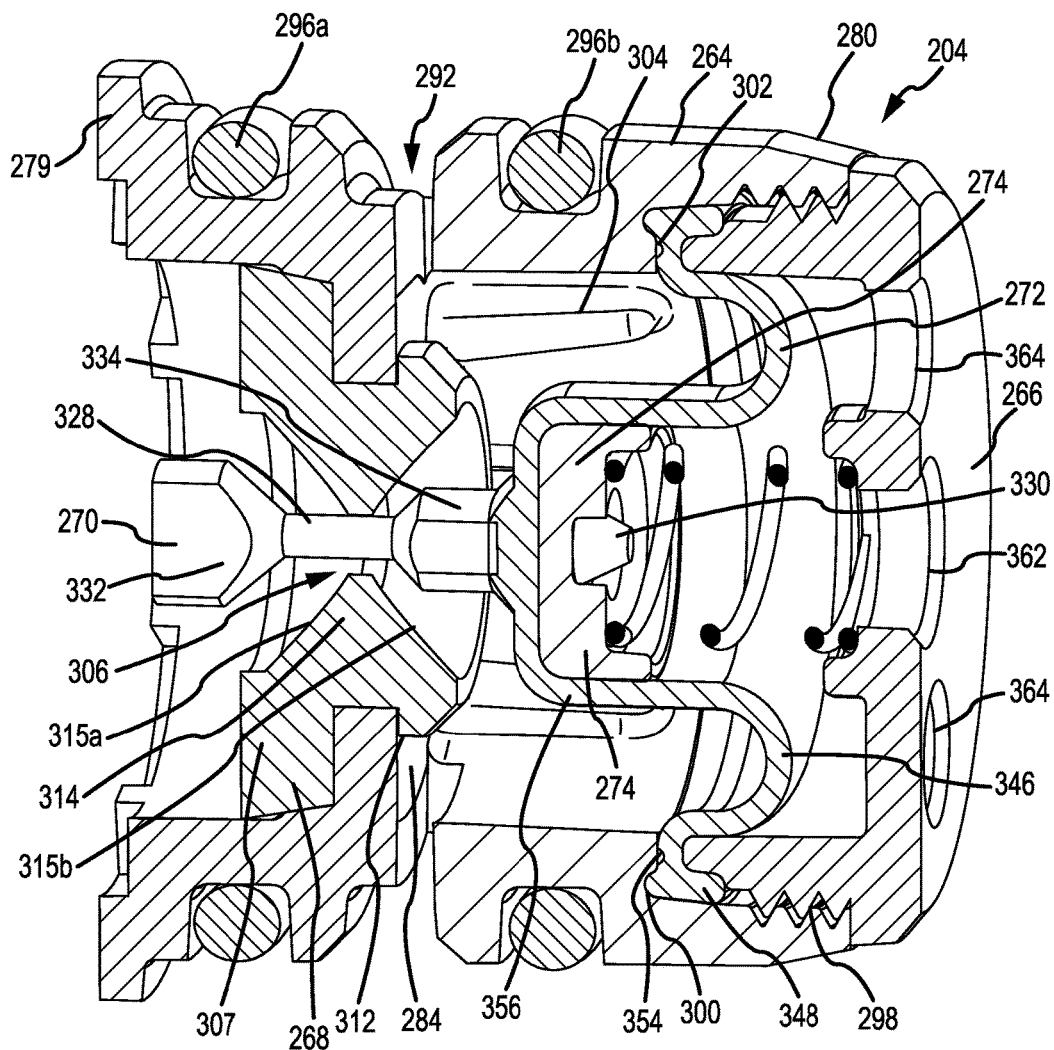
FIG. 10 is an enlarged cross-section view of a pressure regulator assembly of the mounting bracket.
Figure 11:
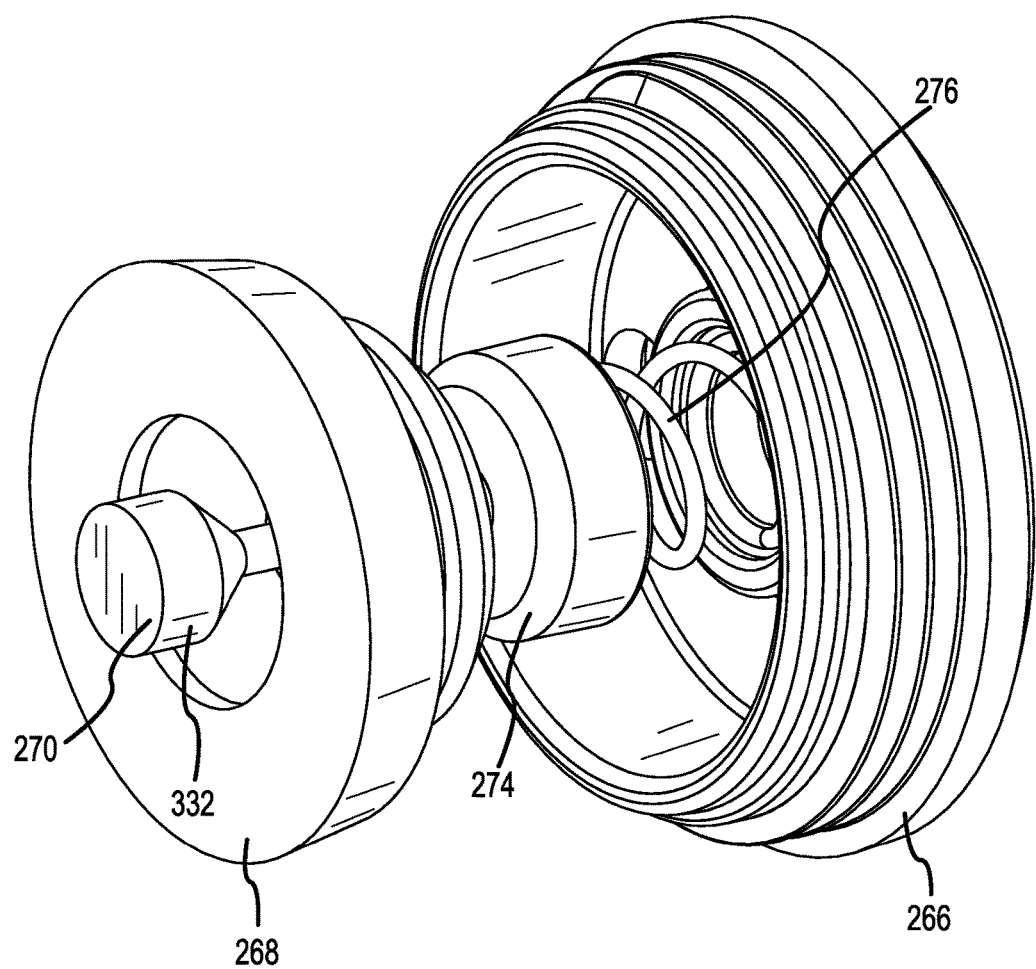
FIG. 11 is an isometric view of the pressure regulator assembly with select elements removed for clarity.

The pressure regulator assembly 204 will now be discussed in more detail. FIG. 10 is an enlarged cross-section view of the pressure regulator assembly 204. FIG. 11 is an isometric view of several of the pressure regulator assembly 204 with select elements removed for clarity. With reference to FIGS. 6, 10, and 11, the pressure regulator assembly 204 may be received within the pressure regulator housing portion 230 of the bracket housing 134. The pressure regulator assembly 204 regulates the pressure of the water flow through the bracket housing 134 to the water flosser 102. The pressure regulator assembly 204 may also reduce the rate of flow of water through the bracket housing 134 before the water reaches the water flosser 102.

An exemplary implementation of the pressure regulator assembly 204 may include a regulator body 264, a regulator cap 266 operably connected to one end of the regulator body 264, a poppet 270, a poppet seal 268, a diaphragm 272, a piston 274, and a biasing member 276. The regulator body 264 may house the poppet seal 268, diaphragm 272, piston 274, poppet 270, and/or the biasing member 276. FIGS. 12A-12E illustrate various isometric views of the regulator body 264. The regulator body 264 defines a proximal cavity 281 that extends within a first end 278 and a distal cavity 283 that extend within a second end 280 of the regulator body 264. A sealing wall 285 defines a flow aperture 282 and provides a separation between the proximal cavity 281 and the distal cavity 283. The flow aperture 282 may be of smaller diameter than the diameters of the proximal and distal cavities 281, 283, which may be substantially similar. The seating wall 284 may extend from the interior walls of the regulator body 264 to form the reduced diameter of the flow aperture 282. In some embodiments, the seating wall 284 may be an annular wall that provides a seating surface for the poppet seal 268, discussed in more detail below.

Figure 12A:
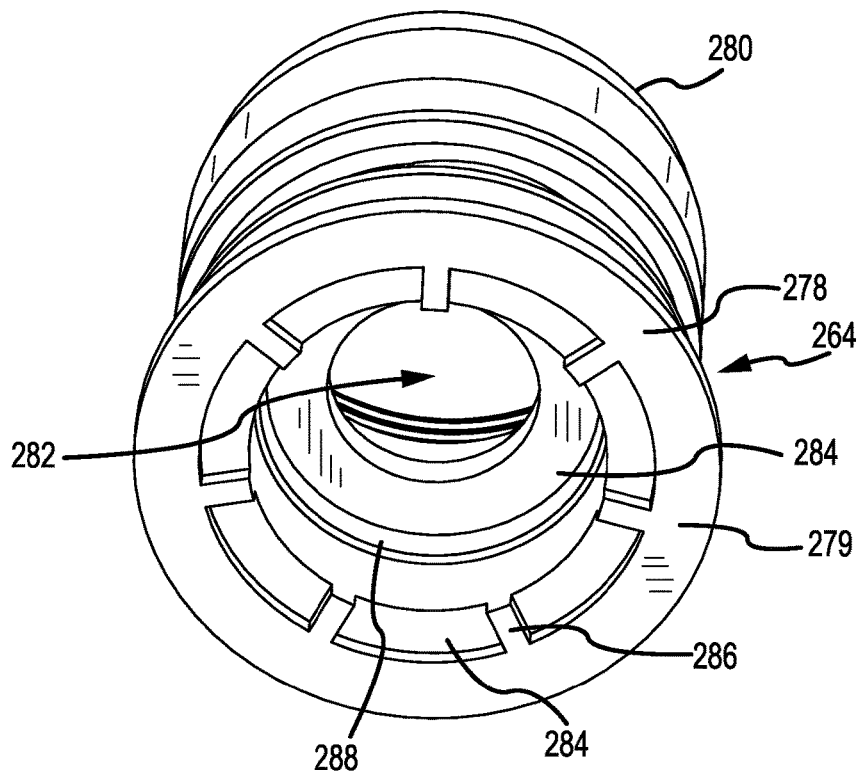
FIG. 12A is a front isometric view of a regulator body of the pressure regulator assembly.

With reference to FIG. 12A, an interior surface of the regulator body 274 within the distal cavity 281 may form an annular shelf 288 adjacent the sealing wall 284. The annular shelf 288 may have a reduced diameter as compared to the remainder of the distal cavity 281 at the first end 278 of the regulator body 264, but may have a larger diameter than the flow aperture 282 in the seating wall 284. That is, in transitioning from the first end 278 towards the seating wall 284, the transition protrusion may provide a graduated decrease in diameter. In some embodiments, the annular shelf 288 may provide a friction interface with the poppet seal 268 to help retain the poppet seal 268 in place within the regulator body 264.

A generally flat distal face 279 of the first end 278 may also define one or more recessed portions 284, each separated from adjacent recessed portions 284 by a separating wall 286. The separating walls 286 may be generally planar with the remaining non-recessed portions of the distal face 279. In the embodiment shown in FIG. 12A, there are seven recessed portions 284 separated by seven separating walls 286. However, in other embodiments, the recessed portions 284 and/or separating walls 286 may be omitted or may have other configurations.

With reference to FIGS. 6, 10, 12A, and 12B, the regulator body 264 may include one or more sealing channels 290a, 290b defined on an outer surface thereof. The sealing channels 290a, 290b may be annular grooves that extend circumferentially around the outer surface of the regulator body 264. The sealing channels 290a, 290b may receive a sealing member, such as O-ring 296a, 296b. As shown in FIG. 6, the O-rings 296a, 296b may be positioned within the sealing channels 290a, 290b and may seal against the pressure regulator housing portion 230.

Figure 12B:
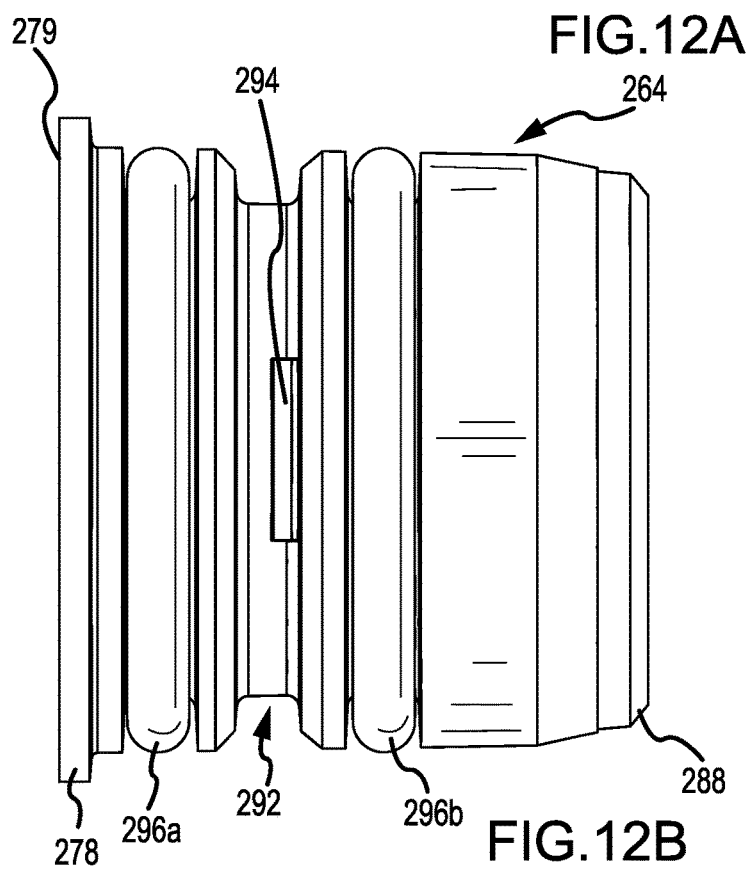
FIG. 12B is a side elevation view of the regulator body with O-rings operably connected thereto.
Figure 12C:
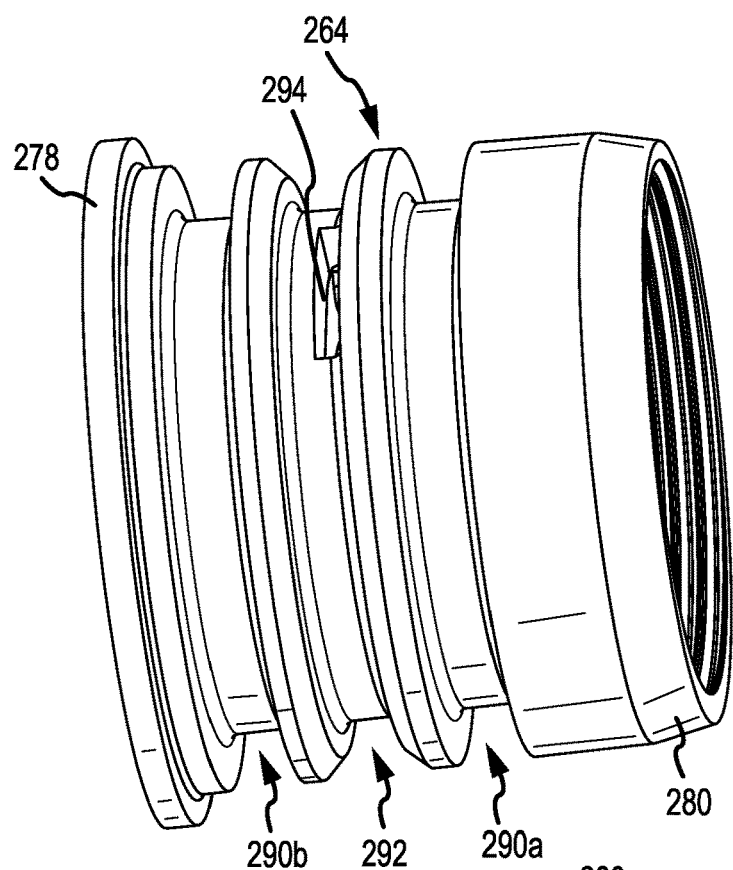
FIG. 12C is a side elevation view of the regulator body.
Figure 12D:
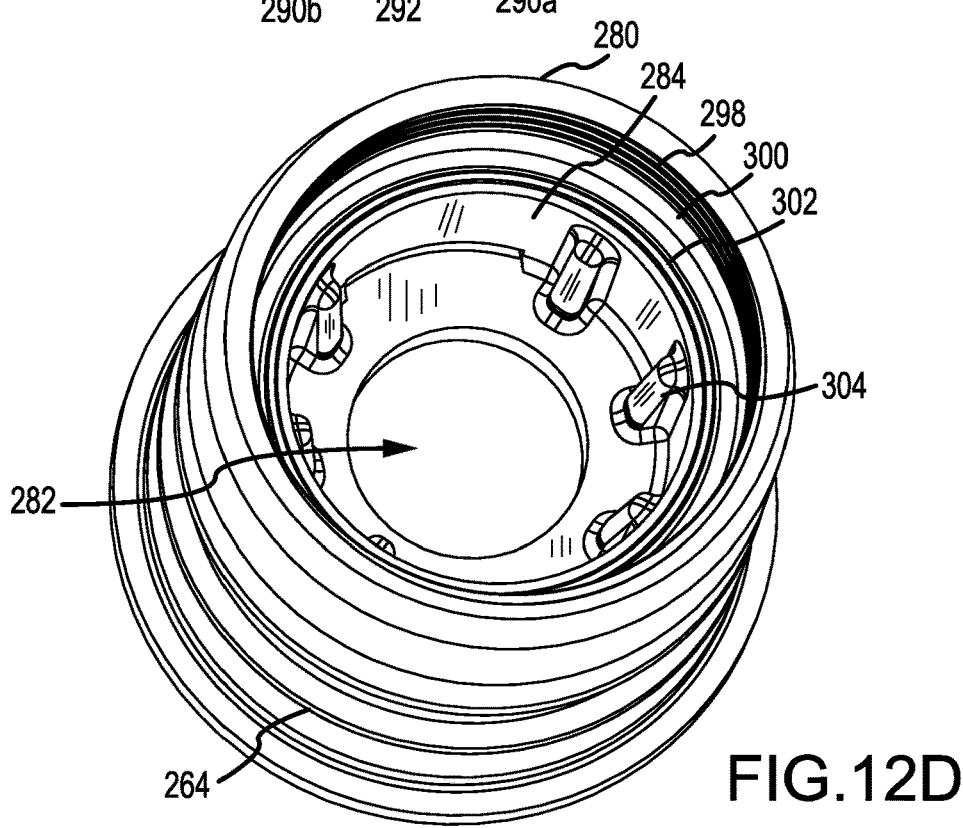
FIG. 12D is a front isometric view of the regulator body.

With reference to FIGS. 10 and 12B, the regulator body 264 may also define a flow channel 292 that extends circumferentially around the outer surface. In one embodiment, the flow channel 292 may be positioned between the sealing channels 290a, 290b and may be formed as an annular groove similar to the sealing channels 290a, 290b. However, unlike the sealing grooves 290a, 290b, the flow channel 292 may not receive a sealing member, but rather may define a fluid flow path around the outer surface of the regulator body 264.

One or more exit apertures 294 may be positioned within the flow channel 292 and defined within the sidewalls of the regulator body 264. In some embodiments, there may be two exit apertures 294 defined on opposing sides of the regulator body 264. Each of the exit apertures 294 provides an outlet for water to exit the regulator body 264. The exit apertures 294 may be formed as generally rectangular slots within the flow channel 292 that are oriented transverse to the length of regulator body 264.

With reference to FIG. 12E, the second end 280 of the regulator body 264 may include a plurality of threads 298 defined on an interior surface. The threads 298 allow the regulator body 264 to mate with the regulator cap 266, as discussed in more detail below.

The regulator body 264 may also include a plurality of spacer studs 304 extending within the distal cavity 283 from the seating wall 284 longitudinally along an inner surface of the regulator body 264. In some embodiments, the spacer studs 304 may decrease in thickness as they extend from the seating wall 284 towards the second end 280.

With reference to FIGS. 10 and 12E, the regulator body 264 may further include a diaphragm retaining groove 300 positioned between the spacer studs 304 and the threads 298. The diaphragm retaining groove 300 is formed in an end of an annular bulwark 301 that extends around the interior walls of the regulator body 264 in the distal cavity 283. A pinch protrusion 302 may also be formed in the annular face of the bulwark 301 at a slightly smaller diameter than the diaphragm retaining groove 300. The diaphragm retaining groove 300 may receive a portion of the diaphragm 272 and, along with the pinch protrusion 302, may help to secure the diaphragm 272 to the regulator body 264. The pinch protrusion 302 may be an annular ridge that extends generally coextensively with the diaphragm retaining groove 300.

The pressure regulator assembly 204 also includes the poppet seal 268. FIG. 13A is a front isometric view of the poppet seal 268. FIG. 13B is a rear isometric view of the poppet seal 268. FIG. 14 is a cross-section view of the poppet seal taken along line 14-14 in FIG. 13B. The poppet seal 268 is operably connected to the regulator body 264 by fitting around the seating wall 285. The poppet seal 268 receives the poppet 270 which extends through a poppet aperture 306 defined through the poppet seal 268.

The poppet seal 268 may include a sealing wall 314 with revamped or chamfered surfaces 315a, 315b on opposite sides of the sealing wall 314. The chamfered surfaces 315a, 315b taper as the sealing wall 314 extends radially inward to define a poppet aperture 306. Thus, the sealing wall 314 varies in diameter from a first side of the poppet seal 268 to a second side of the poppet seal 268. With reference to FIG. 14, the sealing wall 314 may have a generally triangular-shaped cross section, gradually reduce the diameter of the poppet aperture 306 up to an inflection point (e.g., a tip of the triangle), and may then gradually increase the diameter of the poppet aperture 306 such that the poppet aperture 306 assumes an hourglass form from one end of the poppet seal 268 to the other. The chamfered surfaces 315a, 315b of the sealing wall 314 may be angled to match a configuration of surfaces of the poppet 270 to allow the poppet 270 to selectively seal the poppet aperture 306.

The poppet seal 268 may also define a seating extension 308 that extends from a thick proximal flange 307. The seating extension 308 may be spaced apart from the proximal flange 307 so as to define a seating channel 310 positioned between a distal frustum 309 of the seating extension 308 and the proximal flange 307 of the poppet seal 268. The seating channel 310 may be an annular groove and, as shown in FIG. 10, may receive the seating wall 284 of the regulator body 264. The distal frustum 309 may define an engagement wall 312 that abuts the seating channel 310. The engagement wall 312 may assist in retaining the seating wall 284 within the seating channel 310.

Figure 15A:
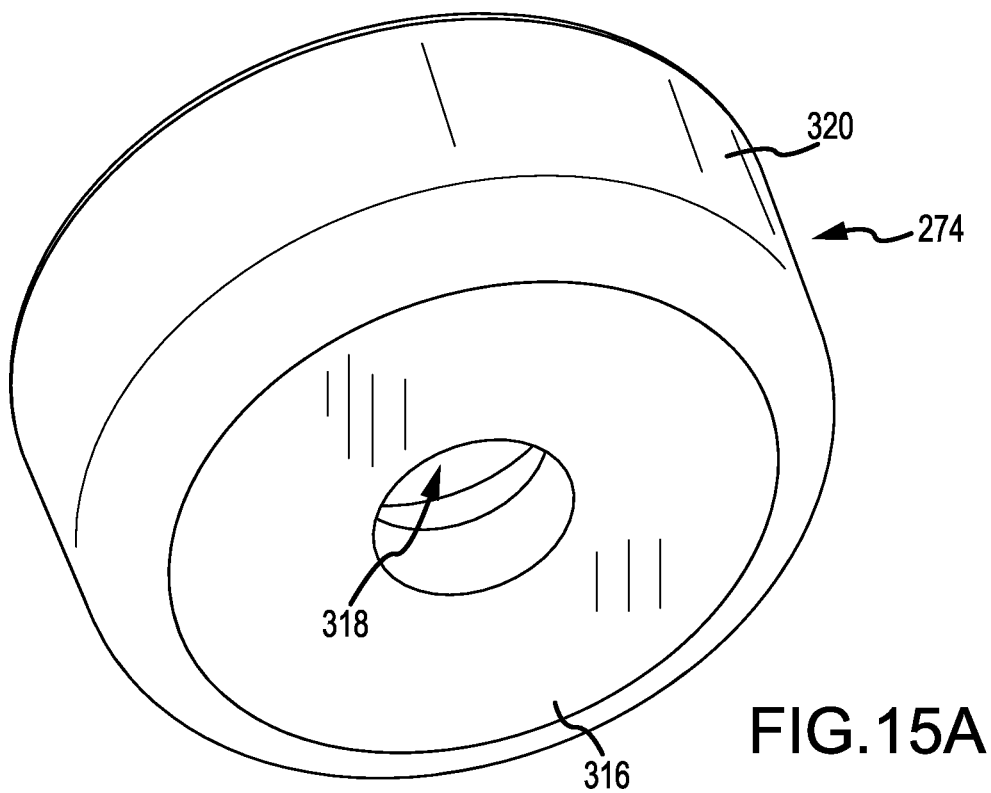
FIG. 15A is a rear isometric view of a piston of the pressure regulator assembly.
Figure 15B:
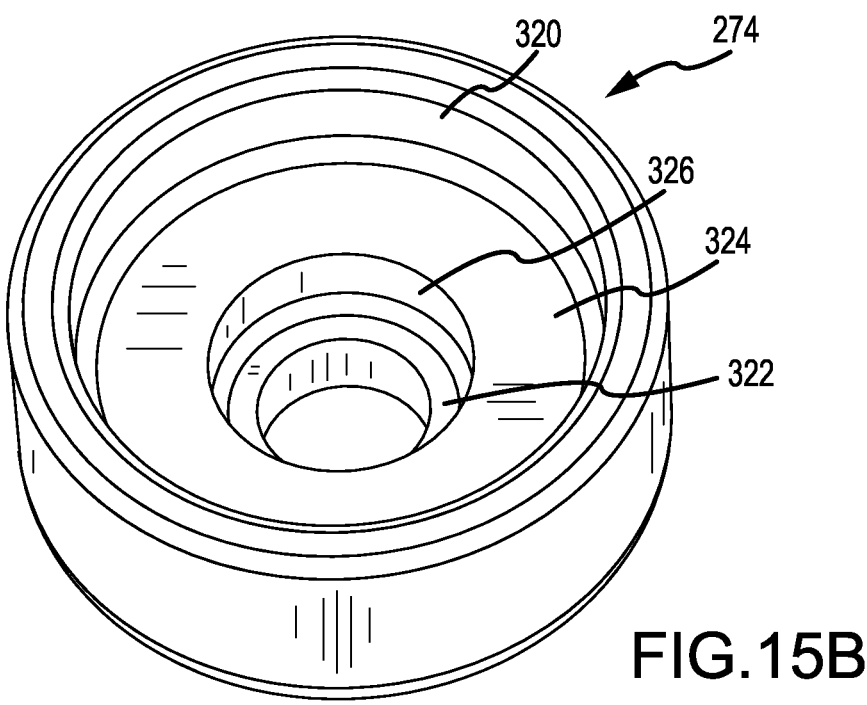
FIG. 15B is a front isometric view of the piston.

The piston 274 will now be discussed in more detail. FIG. 15A is a rear isometric view of the piston 274. FIG. 15B is a front isometric view of the piston 274. The piston 274 is operably connected to the poppet 270 and the biasing member 276. The piston 274 includes a back surface 316 and a front surface 324 with a receiving aperture 318 that extends through the back surface 316 and front surface 324. The diameter of the receiving aperture 318 increases as it transitions from the back surface 316 to the front surface 324 to define an engagement seat 322. The engagement seat 322 is recessed front the front surface 324 and may be surrounded by an interior wall 326. The outer perimeter of the front surface 324 may include an outer wall 320 that extends outward away from the front surface 324.

Figure 16:
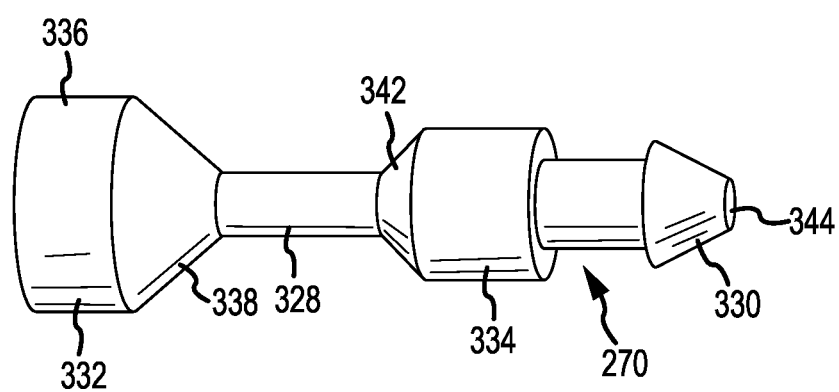
FIG. 16 is a side isometric view of a poppet of the pressure regulator assembly.

FIG. 16 is a side elevation view of the poppet 270. The poppet 270 includes an elongated body 328 having a head 330 on one end and a sealing member 332 on a second end. Additionally, a middle portion of the body 328 includes an engagement segment 334 positioned between the head 330 and the sealing member 332. The head 330 may have a frustum or triangular shape that may have a planar or flat tip 344. The smaller diameter of the tip 344 of the head 330 allows the poppet 270 to be received within the receiving aperture 318 of the piston 274, and the larger diameter base formed by the angled outer walls engages with the engagement seat 322 to operably connect the poppet 270 to the piston 274.

The intermediate or engagement segment 334 has a larger diameter than the elongated body 328 and includes a cylindrical portion 340 and a frustum portion 342. The cylindrical portion 340 may face the head 330 and the frustum portion 342 may face the sealing member 322 at the opposite end of the poppet 270. In this manner, the engagement segment 334 may transition from a smaller diameter at the end of the frustum portion 342 to a larger diameter that then remains constant forming the cylindrical portion 340. The angled walls forming the frustum portion 342 may correspond to the chamfered surface 315b of the sealing wall 314 of the poppet seal 268.

The sealing member 332 of the poppet 270 may have a shape that is generally similar to the engagement segment 334, but may be oriented in a different direction. Specifically, the sealing member 332 may include a cylindrical portion 336 and a frustum portion 338, with the cylindrical portion 336 oriented at the end of the poppet 270 and the frustum portion 338 oriented towards the engagement segment 334. Additionally, the sealing member 332 may generally have a larger diameter than the engagement segment 334 and the head 330. The frustum portion 338 of the sealing member 332 may generally correspond to the angle of the sealing walls 314 of the poppet seal 268, but generally may allow the sealing member 332 to seal the poppet aperture 306 defined within the poppet seal 268.

With reference to FIG. 16, in some instances, the elongated body 328 may have a first diameter between the sealing member 332 and the engagement segment 334 and a second, larger, diameter between the cylindrical portion 340 and the head 330. Additionally, the sealing member 332, the engagement segment 334, and the head 330 may each have larger diameters than the elongated body 328.

Figure 17A:
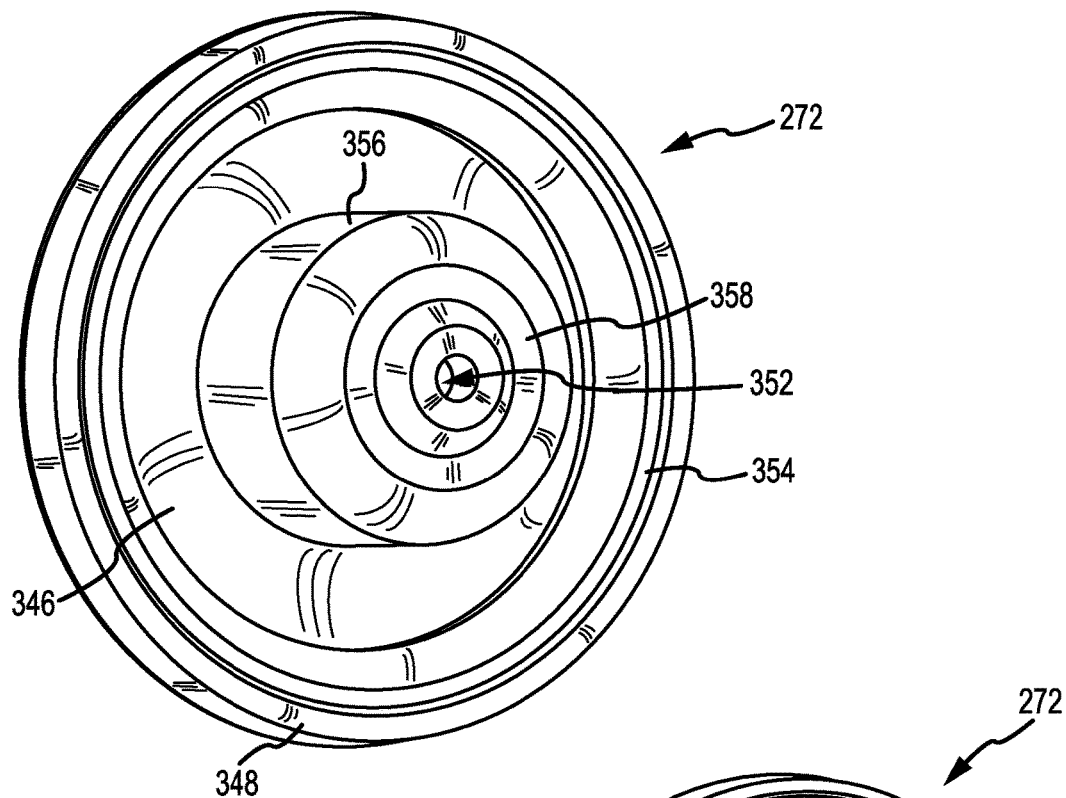
FIG. 17A is a rear isometric view of a diaphragm of the pressure regulator assembly.
Figure 17B:
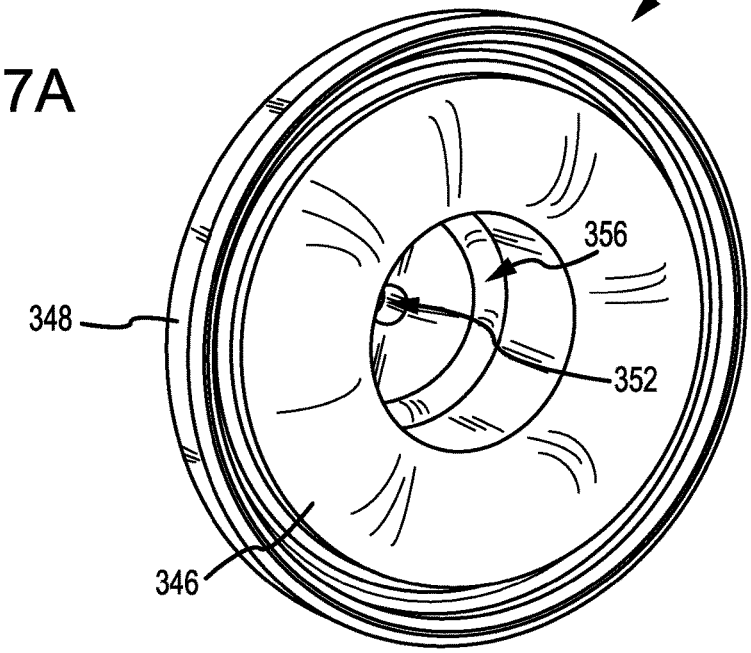
FIG. 17B is a front isometric view of the diaphragm.

The diaphragm 272 may have a flexible body 346 that may flex or bend as the pressure applied to it varies. FIG. 17A is a front isometric view of the diaphragm. FIG. 17B is a rear isometric view of the diaphragm. With reference to FIGS. 10, 17A, and 17B, the diaphragm 272 may have a flexible body 346 surrounded by a rim 348. The rim 348 surrounds outer perimeter of the flexible body 346. The flexible body 346 may flex under pressure without breaking or rupturing, which may allow the diaphragm (in conjunction with other elements of the regulator assembly 204) to control the water flow through to the water flosser 102.

A retaining wall 356 extends outward from a front side of the flexible body 346. A cap 358 extends to cover the open end of the retaining wall 356, so that the cap 358 and the retaining wall 356 define a biasing cavity 350 on the back side of the diaphragm 272. A body aperture 352 is defined through the cap 358 and is configured to correspond to the diameter of the elongated body 328 of the poppet 270.

The diaphragm 272 further may include an annular connecting groove 354 positioned between the rim 348 and the flexible body 346. The connecting groove 354 may engage with the pinch protrusion 302 of the regulator body 264.

Figure 18A:
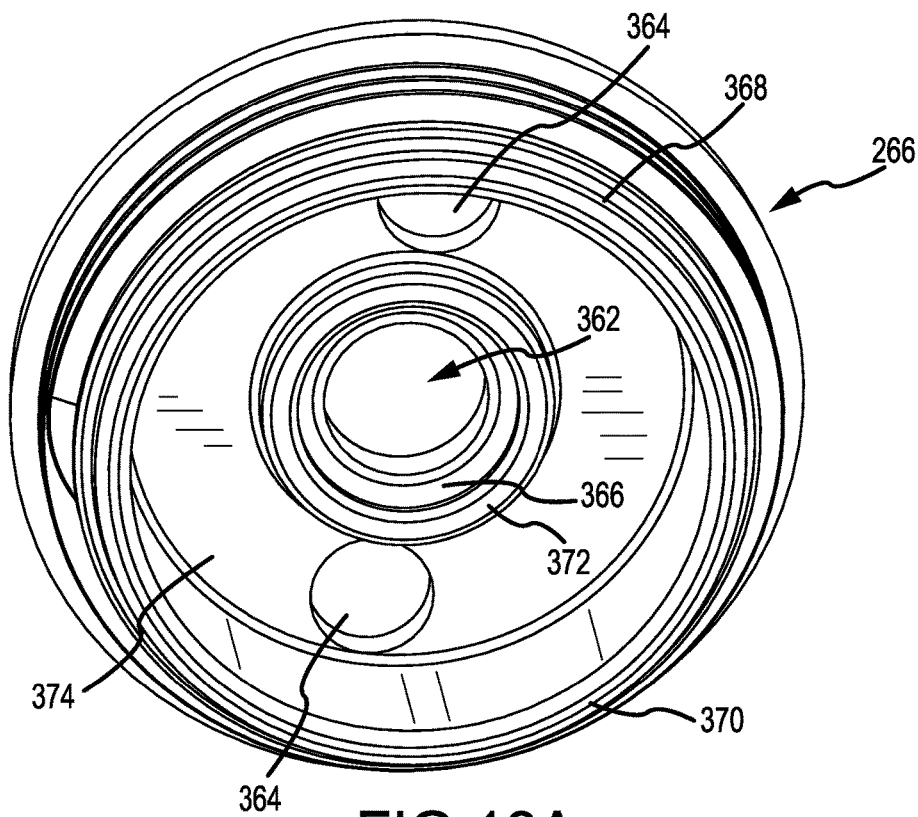
FIG. 18A is a rear isometric view of a regulator cap of the pressure regulator assembly.
Figure 18B:
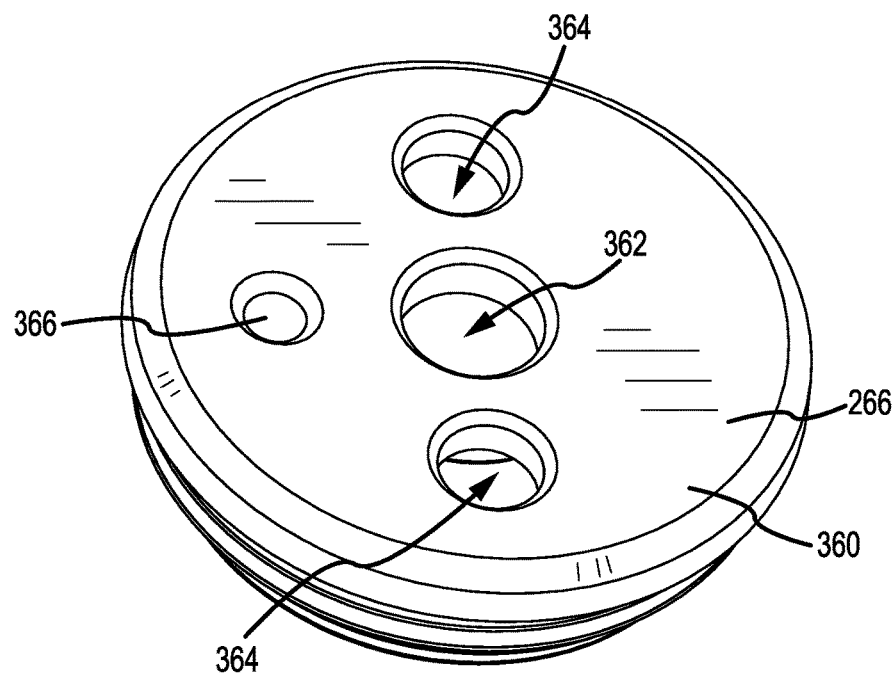
FIG. 18B is a front isometric view of the regulator cap.

The regulator cap 266 may operably connect to a front end of the regulator body 264. FIG. 18A is a rear isometric view of the regulator cap 266. FIG. 18B is a front isometric view of the regulator cap 266. With reference to FIGS. 10, 18A, and 18B, the regulator cap 266 has a first end 374 and a second end 360. A threaded cylinder 368 extends outward from the first end 374 to operably connect to the regulator body 264. The second end 360 may have a larger diameter than the threaded cylinder 368, which may allow the second end 360 to seal against the end of the regulator body 264 when the two components are connected together.

The terminal end of the threaded cylinder 368 may transition to form a pinch rim 370. With reference to FIG. 10, the pinch rim 370 may press against the rim 348 of the diaphragm 272 to sandwich it against the annular bulwark 301 of the regulator body 264.

The first end 374 of the regulator cap 266 may further include a biasing wall 372 that extends outward therefrom. The biasing wall 372 may receive an end of the biasing member 276 to operably connect the biasing member 276 to the cap 266. For example, in one embodiment, a grip channel 366 may be defined along an inner surface of the biasing wall 372 and an end portion of the biasing member 272 may be retained within the grip channel 366 (see FIG. 10). The biasing member 276 may be substantially any element which may exert a biasing force in a particular direction and/or may be compressible under a particular force. In some embodiments, the biasing member 276 may be a coil spring.

A retaining aperture 362 may be defined through a center of the regulator cap 266. Additionally, the regulator cap 266 may include one or more venting apertures 364, as well as a recess 366. The venting apertures 364 may provide for fluid communication between the first and second ends of the cap 266. The weep hole 234 may be provided within the pressure regulator housing portion 230 to be in fluid communication with the second end 360 of the regulator cap 266. The weep hole 234 may provide for air flow as the diaphragm 272 moves back and forth, thereby avoiding negative pressure effects on the movement of the diaphragm 272. The weep hole 234 may also indicate to a user that the O-ring 269*b* around the regulator body 264 has failed and needs replacement in order to ensure proper water pressure is provided to the water flosser 102.

With reference to FIG. 10, assembly of the pressure regulator assembly 204 will now be discussed. The poppet seal 268 may be operably connected to the regulator body 264 with the seating wall 284 of the regulator body 264 being received into the seating channel 310 of the poppet seal 268. The seating extension 308 may extend through the flow aperture 282 towards the distal end of the regulator body 264. In this manner, the engagement wall 312 of the poppet seal 268 may interface with a distal face of the seating wall 284. The annular shelf 288 of the regulator body 264 may substantially follow the outer surface of the poppet seat 268, so that the outer surface of the poppet seal 268 may generally seal against the interior surface of the annular shelf 288.

The poppet 270 is received into the poppet aperture 306 defined within the poppet seat 268. The poppet 270 may be oriented such that the head 330 may extend through the seating extension 308. In this orientation, the sealing member 332 of the poppet 270 may prevent the poppet 270 from being pulled entirely through the poppet seal 268, as the sealing member 332 abuts the chamfered surface 315*b* of the poppet seal 268. The poppet 270 head 330 extends through the seating extension 308 and engages with the diaphragm 272.

The head 330 of the poppet 330 may extend through the body aperture 352 in the diaphragm 272 to engage the piston 274. The head 330 of the poppet 270 extends through the receiving aperture 318 of the piston 274 and the bottom end of the head 330 sits within the engagement seat 322 of the piston 274. The frustum shape of the head 330 has a larger diameter than the receiving aperture 318 and therefore as the head 330 may be securely engaged with the piston 274. The biasing member 276 has a first end partially received within the interior wall 326 of piston 274, which operably connects the biasing member 276 to the piston 274.

The head 330 of the poppet 270, the piston 274, and the first end of the biasing member 276 may be received into biasing cavity 350 of the diaphragm 272. The poppet 270 may extend through the body aperture 352 of the diaphragm 272. The rim 348 of the diaphragm 272 may then be positioned within the diaphragm groove 300 of the regulator body 274 and the end cap 266 may be threaded onto the regulator body 274, securing the regulator cap 266 and the diaphragm 272 to the regulator body 274. For example, the threads 298 of the regulator body 264 engage with the external threads 368 of the regulator cap 266. The pinch rim 370 of the regulator cap 266 may press against a portion of the diaphragm 272 as the regulator cap 266 is secured in position.

Once the pressure regulator assembly 204 is operably connected, the entire assembly 204 may be positioned within the pressure regulator housing 230 defined in the bracket housing 134. As shown in FIG. 6, the regulator cap 266 may be positioned adjacent to an inner surface of the distal end 162 of the bracket housing 134. The distal face 279 may extend inward past a terminal end of the regulator housing 230. The O-ring 296*a* seals against the interior surface of the regulator housing 230 to prevent water from flowing between the regulator housing 230 and the pressure regulator body 274.

The regulator body 274 is orientated within the pressure regulator housing 230 so that the flow channel 292 is aligned with the irrigating flow aperture 336 defined in the regulator housing 230. As shown in FIG. 6, the two O-rings 296*a*, 296*b* seal against the regulator housing 230 on either side of the irrigating flow aperture 336, and so only fluid from the exit apertures 294 that travels through the flow channel 292 is in fluid communication with the irrigating flow aperture 336. Additionally, the second O-ring 296*b* may seal against the pressure regulator housing 230 to prevent water from flowing around the regulator body 274 to reach the regulator cap 266. In this manner, the weep hole 234 and the apertures defined within the regulator cap 266 may be in communication with each other, but separated from fluid communication with the water flow through the regulator body 274.

Once the pressure regulator assembly 204 is received within the pressure regulator housing 230, the water supply assembly 206 may be operably connected to the bracket housing 134. With continued reference to FIG. 6, the pivot seat 210 may be inserted into the bracket housing 134 with the fins 211 being aligned in the attachment slots 228. The pivot ball 220 and water filter 208 may then be positioned inside the bracket housing 134 and the coupling collar 136 may be threaded onto the receiving threads 226.

The Hose

Figure 2:
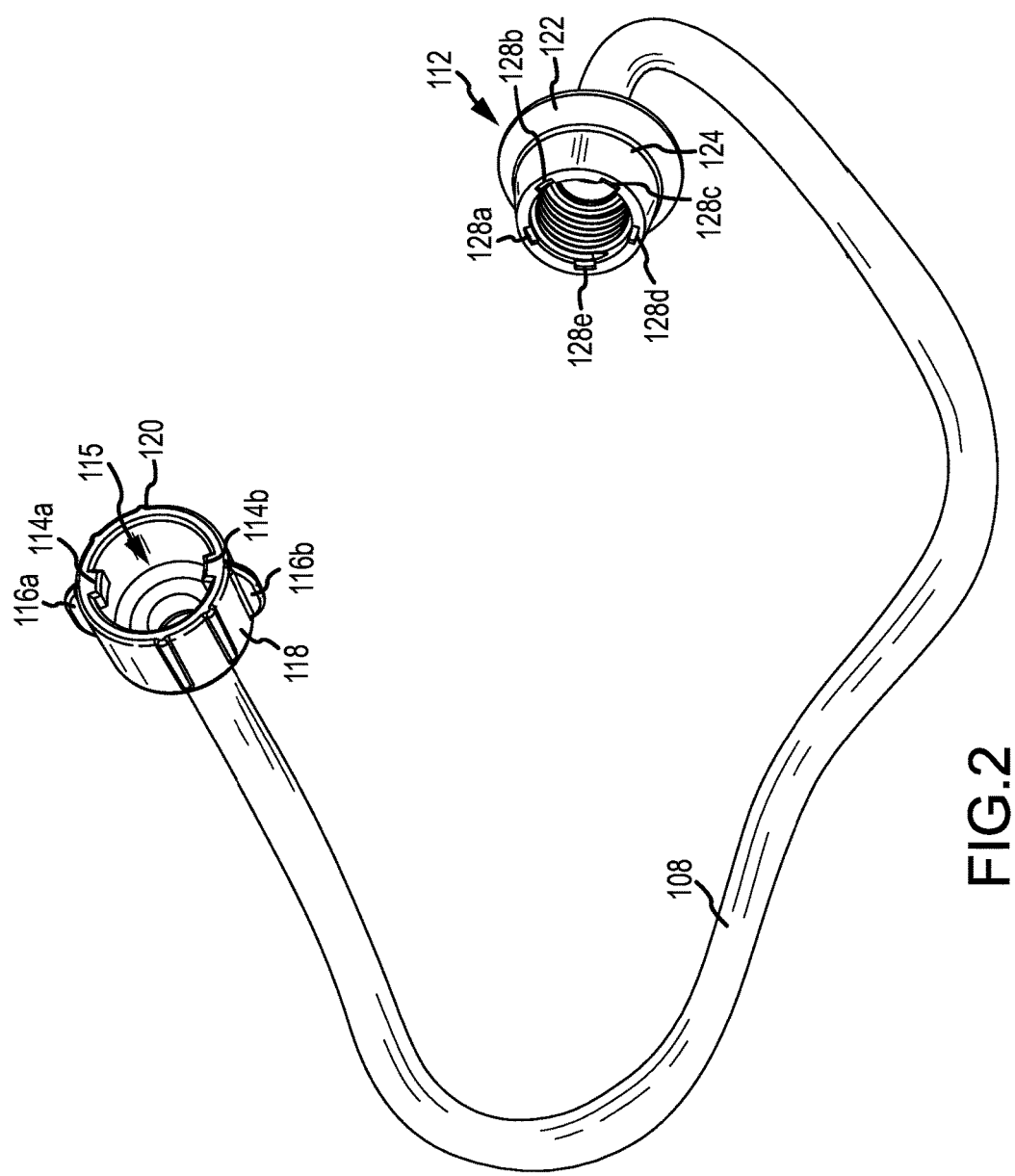
FIG. 2 is an isometric view of a hose for fluidly connecting the mounting bracket and the water flosser.

In one example, the water flosser 108 may be operably connected to the mounting bracket 104 through the cradle 130 and may be fluidly connected to the mounting bracket 104 through a hose 108 extending between the mounting bracket 104 and the water flosser 102. FIG. 2 is an enlarged isometric view of the hose detailing a first or bracket end 110 of the hose 108 and a second or irrigating end 112 of the hose 108. With reference to FIGS. 1B and 2, the hose 108 extends between the mounting bracket 104 and the water flosser 102 to provide fluid communication therebetween. The hose 108 may be a generally elongated hollow tube and may transport water or other fluids therethrough. The hose 108 may generally be flexible to allow a user to move the water flosser 102 in various angles and distances from the mounting bracket 104. For example, the hose 108 may be formed of a rubber or silicon material.

The first or bracket end 110 of the hose 108 operably connects the hose 108 to the mounting bracket 104. As shown in FIG. 2, the bracket end 110 of the hose 108 may include a bracket hose connector 118 that may have a larger diameter than the hose 108 and, in some instances, may be a harder material than the body of the hose 108. The hose connector 110 may be integrally formed with the hose 108 or may be operably connected, for example, rotatably connected, thereto. The hose 108 may extend into a back end of the hose connector 118, which may be sealed with respect to the bracket end 110 of the hose 108. The front end of the hose connector 118 may be open in order to be in fluid communication with the mounting bracket when connected thereto, as discussed in more detail below. Two more connection nubbins 114*a* and 114*b* may be formed on a surface of an inner wall 115 of the hose connector 118. The nubbins 114a and 114b may be configured to interface with the connection grooves 144 and connection on the water flosser coupling 170 of the mounting bracket 104.

The outer surface of the bracket hose connector 118 may include one or more finger grips 120 or ridges that may extend outwardly therefrom to assist a user in griping and aligning the hose connector 118. Additionally, the bracket hose connector 118 may include one or more finger flanges 116a, 116b, which, similar to the finger grips 120, may assist a user in handling and manipulating the bracket hose connector 118, such as to attach the bracket end 110 to the mounting bracket 104. The finger flanges 116a, 116b may extend farther outward from the outer surface of the bracket hose connector 118 than the finger grips 120 and may generally be configured to be grasped between a user's fingers to assist the user in attaching the hose 108 to the mounting bracket 104.

With continued reference to FIG. 2, the second or irrigating end 112 of the hose 108 operably connects the hose 108 to the water flosser 102. In one exemplary embodiment, the irrigating end 112 may include a threaded connector 124 that extends outward from the terminal end of the hose 108 and includes internal threads 126 configured to mate with the water flosser 102, as discussed in more detail below. The threaded connector 124 may also define one or more alignment recesses 128a, 128b, 128c, 128d, 128e on a front end. The alignment recesses 128a, 128b, 128c, 128d, 128e may be recessed from the outer surface on the front open end of the threaded cylinder 124.

With reference to FIGS. 1B and 2, the irrigating end 112 of the hose 108 may also include a retaining lip 122 positioned between the threaded connector 124 and the hose 108. The retaining lip 124 may assist in retaining the water flosser 102 within the cradle 130 of the mounting bracket 104. For example, when the water flosser 102 is placed in the cradle 130, the cradle 130 may extend around the threaded connector 124 to hold the water flosser 102 in a snap fit manner or merely provide a support surface from which the water flosser 102 hangs. In this example, the retaining lip 124 extends radially outward from the threaded connector 124 as an annular ring to engage with the outer walls of the cradle 130 that extend around the threaded connector 124. In this manner, the retaining lip 124 may help to retain the water flosser 102 in a secure orientation within the cradle 130.

The Water Flosser

The water flosser 102 will now be discussed in more detail. FIGS. 19A-19F illustrate various views of the water flosser 102. The water flosser 102 may include a water flosser body 380, a water flosser housing 385, a tip 382, a water flosser port 386 extending from the water flosser body 380, a switch 388, and a battery pack 392. The water flosser 102 may also include a tip cover 384 for covering the tip 382 and a hand grip 390 on the water flosser body 380 to provide a gripping surface for a user.

The tip 382 may be operably connected to a top end of the water flosser body 380 and, in some embodiments, may be removable from the oral irrigating body 380. The water flosser 102 may include a tip release button 394 that may allow the tip 382 to be removed from the water flosser body 380. The water flosser port 382 may extend from a top rear end of the water flosser body 380 and may operably connect with the hose 108. The water flosser port 382 may also be retained in the cradle 130 when the water flosser is in a stored position, as discussed in more detail below.

The battery pack 392 may be removable from the water flosser body 380 and houses an energy source for the water flosser, e.g., standard or rechargeable batteries. In some embodiments, a stabilizing boss 396 may be formed extending from the housing of the battery pack 392 as shown in FIG. 3.

The switch 388 may extend through a switch slot 398 and may move parallel to a longitudinal axis of the water flosser body 380. However, it should be noted that in other implementations the switch 388 may be configured in other manners, e.g., the switch 388 may move laterally relative to the body, may be compressible, and so on.

Figure 20A:
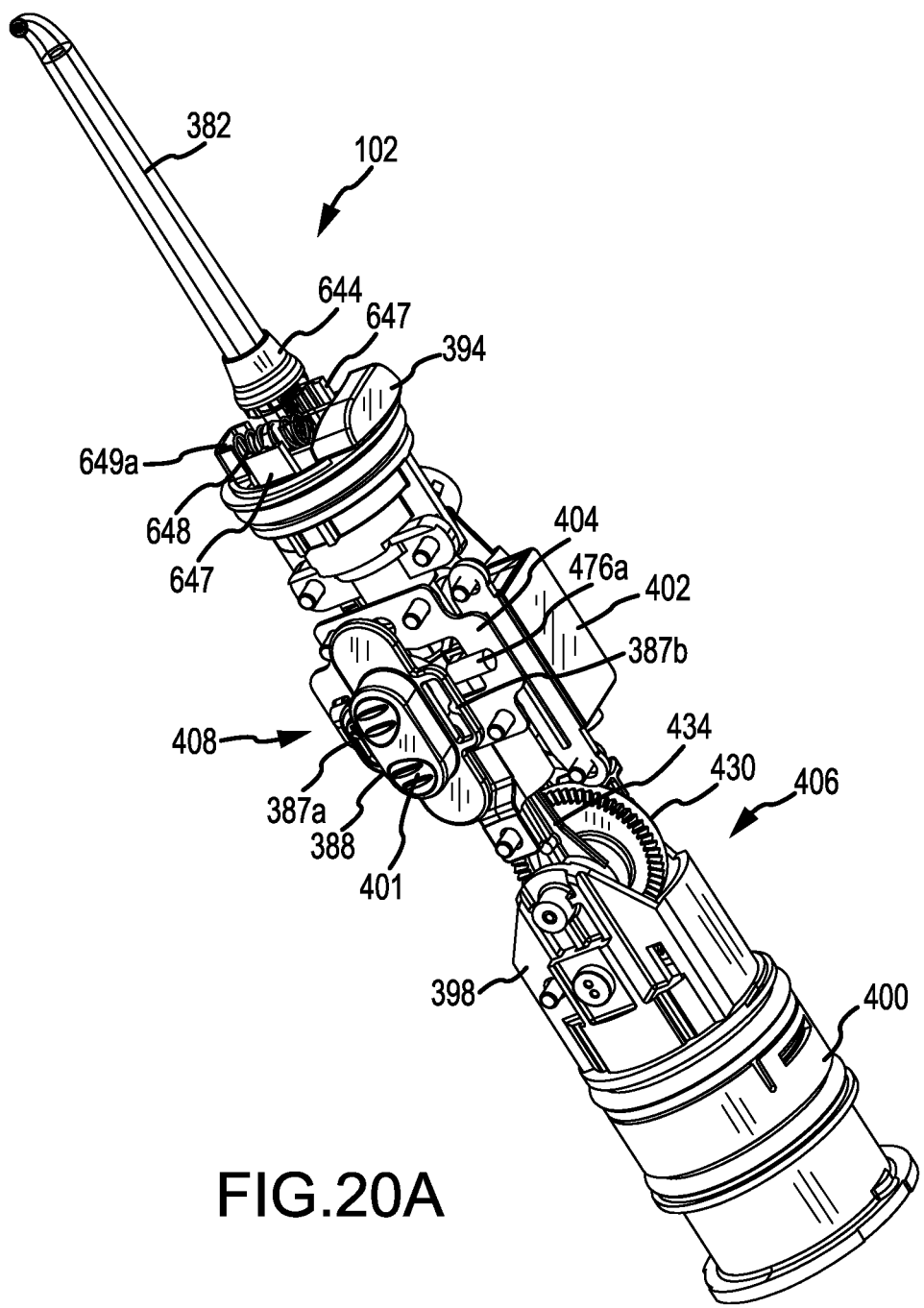
FIG. 20A is a front isometric view of the water flosser with an outer housing hidden.
Figure 20B:
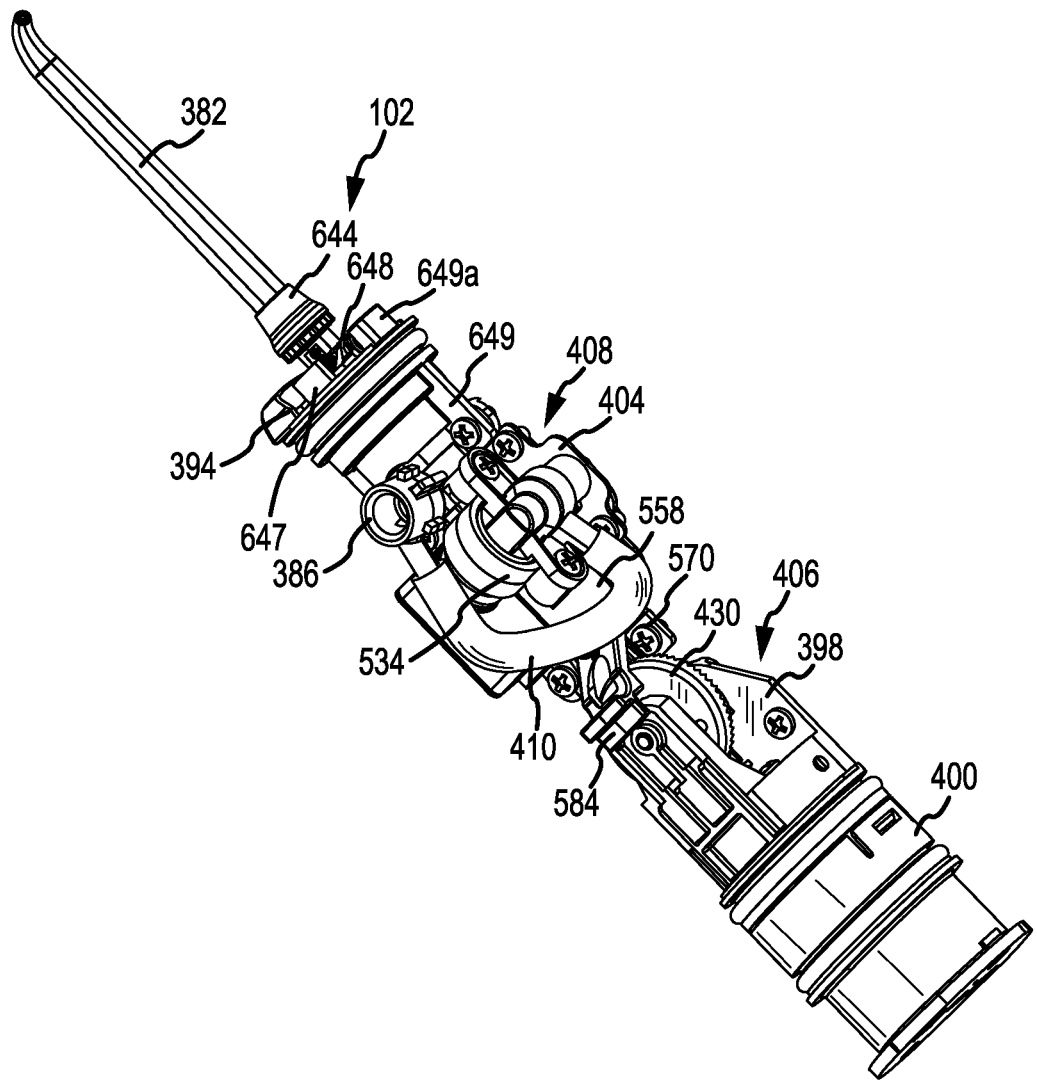
FIG. 20B is a rear isometric view of the water flosser with the outer housing hidden for clarity.

As shown in FIGS. 20A and 20B, the water flosser 102 may include a control assembly 408, which may control the functions of the water flosser 102, as well as a drive assembly 406 which may drive components of the water flosser 102. FIG. 20A is a front isometric view of the water flosser 102 with the water flosser body 380 removed. FIG. 20B is a rear isometric of the water flosser 102 with the water flosser body 380 removed. The control assembly 408 may include the switch 388, as well as one or more pressure and flow valves described in more detail below. The control assembly 408 and the drive assembly 406 may be operably connected and also select components of each assembly may be electrically connected and mechanically linked. Each the control assembly 408 and the drive assembly 406 will be discussed, in turn, below.

Drive Assembly

Figure 21:
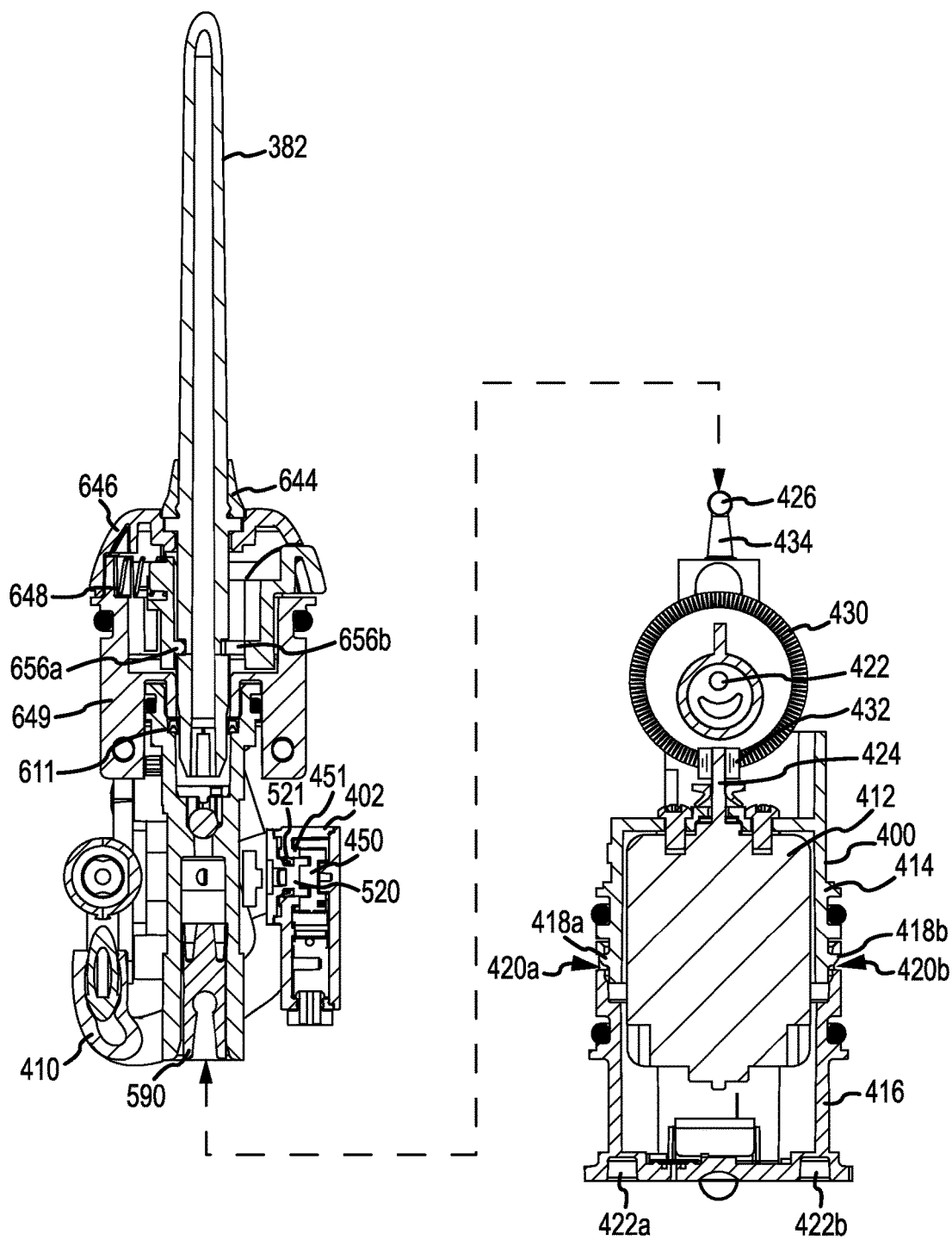
FIG. 21 is a cross-section view of the water flosser taken along line 21-21 in FIG. 19D.
Figure 22:
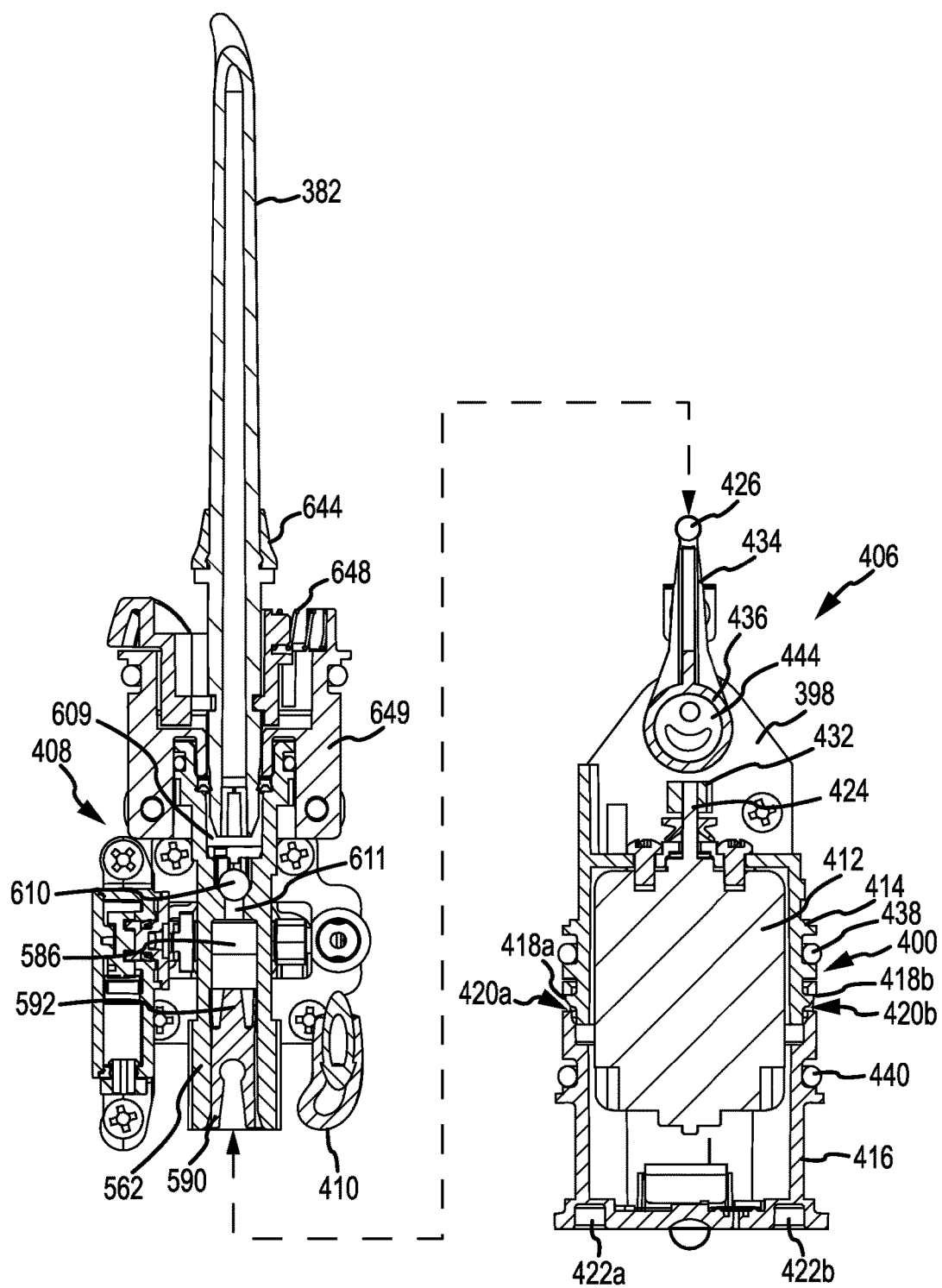
FIG. 22 is a cross-section view of the water flosser taken along line 22-22 in FIG. 19D.

The drive assembly 406 may include a motor 412, one or more gears, and a piston. FIG. 21 is a cross-section view of the water flosser 102 taken along line 21-21 in FIG. 19D. FIG. 22 is a cross-section view of the oral taken along line 22-22 in FIG. 19D. With reference to FIGS. 20A-22, the drive assembly 406 may include a motor 412 housed within a motor housing 400, a motor shaft 424 rotatably connected to the motor 412, a small gear 432 mounted on the motor shaft 424, and a large gear 430 operably connected to the small gear 432. The large gear 430 is operably connected to a pump piston arm 432 through a piston socket 436. The large gear 430, the small gear 432, and the motor 412 may be operably connected to a chassis 398 that may provide a support structure for the drive assembly components.

The motor housing 400 houses the motor 412 and may provide one or more electrical contacts 422a, 422b from the motor to a power source, e.g., batteries within the battery pack 392. The electrical contacts 422a, 422b may be defined on a bottom end of the motor housing 400, which may be in physical and electrical contact with one or more corresponding contacts on the battery pack 392, as discussed in more detail below. The electrical contacts 422a, 422b may be strips of a conductive material (e.g., metal) that may be in communication with both the motor 412 and the batteries.

In some embodiments, the motor housing 400 may include an upper motor housing 414 and a lower motor housing 416 operably connected together. As shown in FIG. 22, the upper motor housing 414 may include one or more detents 418a, 418b that are received within corresponding openings 420a, 420b on the lower motor housing 416. It should be noted that the upper motor housing 414 and the lower motor housing 416 may be operably connected together in other manners, such as, but not limited to, ultrasonic welding, adhesive, a twist lock connection, or the like. The motor housing 400 may also define one or more annular channels to receive sealing members, such as O-rings 438, 440.

The motor 412 may be received within the motor housing 400 and the motor shaft 424 driven by the motor 412 may extend through the housing 400. The small gear 432 is mounted on the free end of the motor shaft 424. The small gear 432 includes a plurality of teeth which are configured to mesh with teeth of the large gear 430 in order to rotate the large gear 430. In this manner, the small gear 432 and the large gear 430 may be movably connected together, and each of the gears may be driven by the motor shaft 424.

Figure 23:
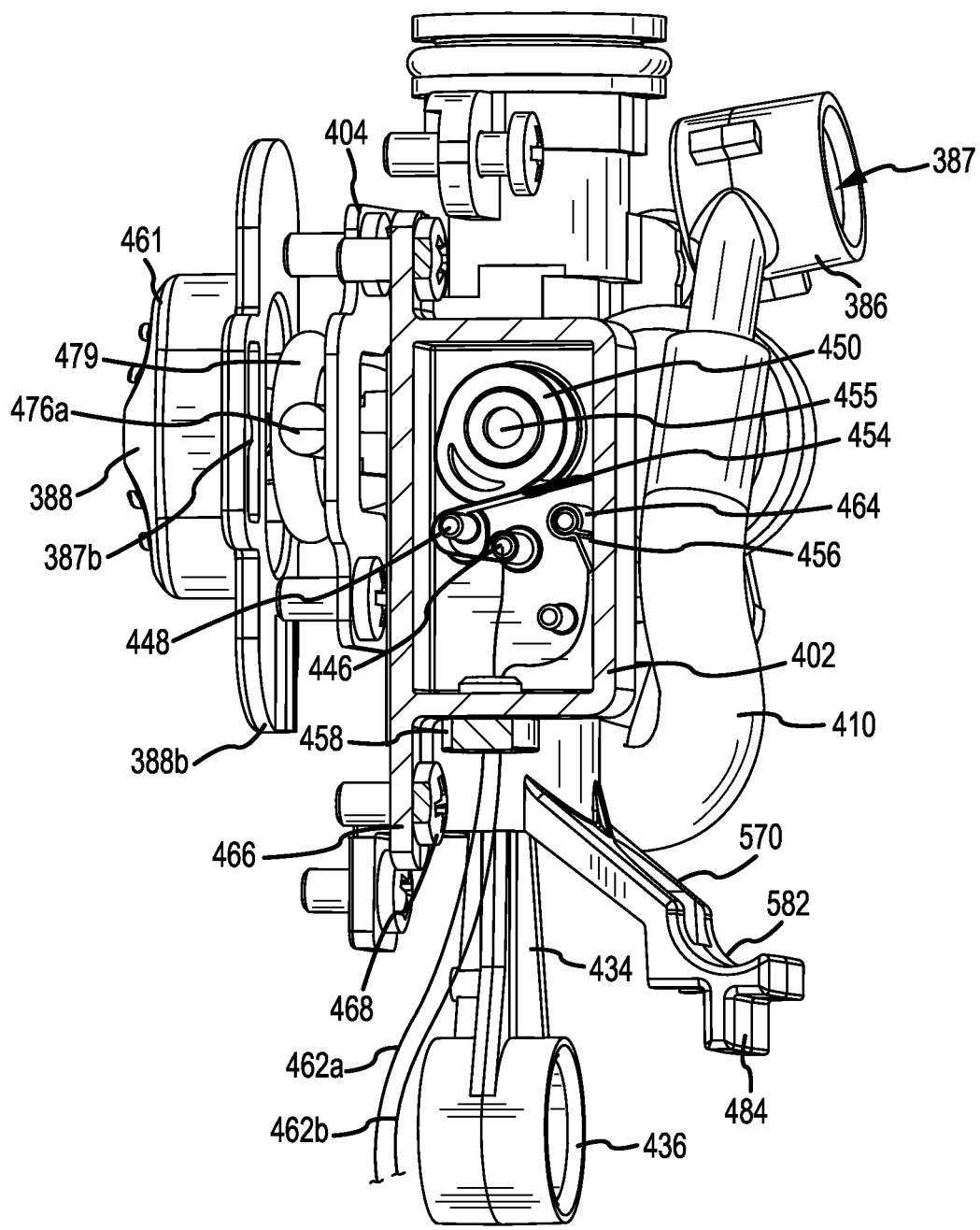
FIG. 23 is a partial cross-section view a control assembly of the water flosser with certain elements hidden for clarity.

FIG. 22 is a partial cross-section view of the water flosser 102 with the water flosser body 380 removed for clarity. As shown in FIG. 22, a piston post 444 may extend from a front surface of the large gear 430 and may be positioned offset from a center axis of the large gear 430. In one implementation, the piston post 444 may be received within a piston socket 436 defined within the pump piston arm 434. The piston socket 346 may rotate freely about the piston post 444. With reference to FIGS. 21, 22, and 23, a piston ball 426 may be formed at one end of the pump piston arm 434 at an opposite end from the piston socket 436. In some embodiments, the pump piston arm 434 may decrease in width from the piston socket 436 towards the piston ball 426. The piston socket 436 may be a hollow cylinder that extends from a bottom end of the pump piston arm 434. A center axis of the piston socket 436 may be parallel to an axis of the piston post 444. An axel pin 442 extends through an aperture in the center axis of the large gear 430 and additionally extends through a hollow shaft in the piston post 444, offset from the center axis of the piston post 444. The lateral ends of the axel pin 442 are received in sockets in the chassis 398. The lateral ends of the axel pin 442 may either be held fixed within the sockets in the chassis 398 or be free to rotate within the sockets in the chassis 398. Each of the large gear 430 and the piston post 444 are configured to rotate freely about the axel pin 442.

Primary Valve

Figure 32A:
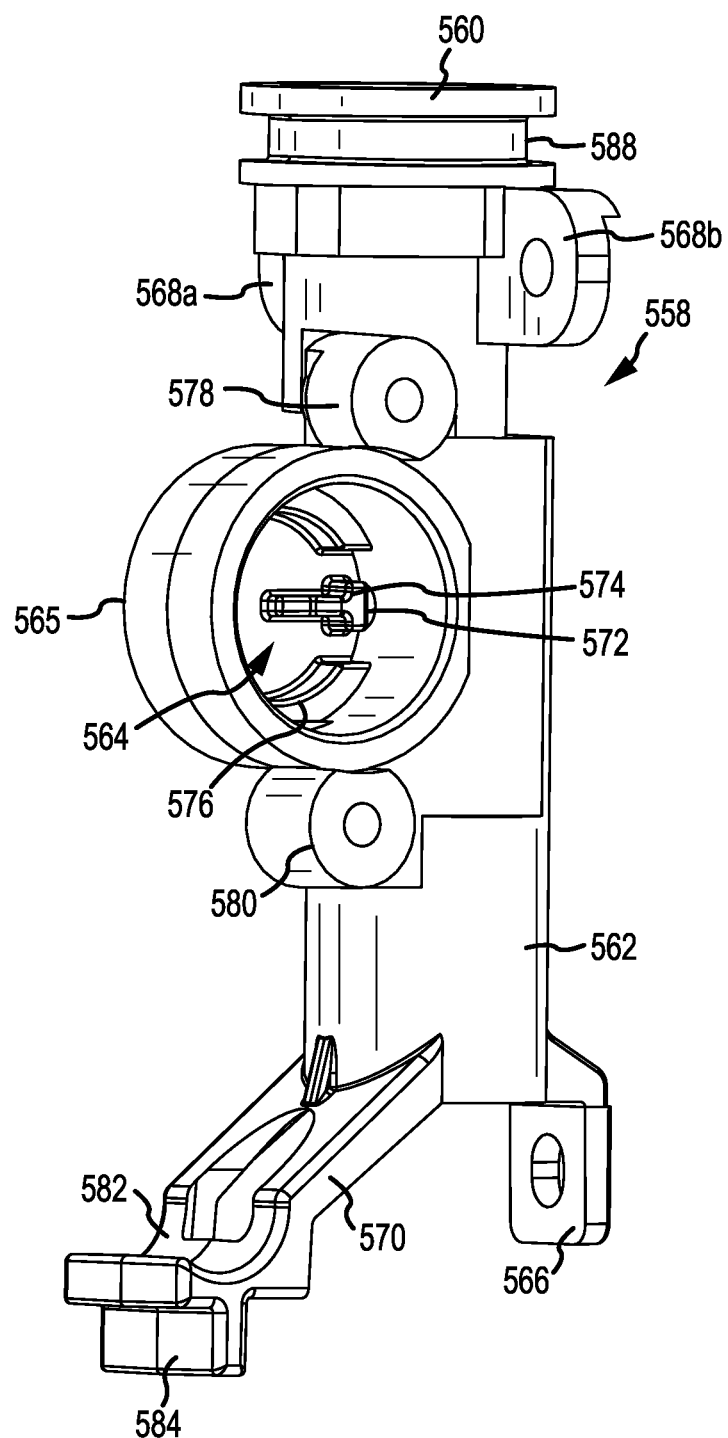
FIG. 32A is a front isometric view of a primary valve of the control assembly.
Figure 32B:
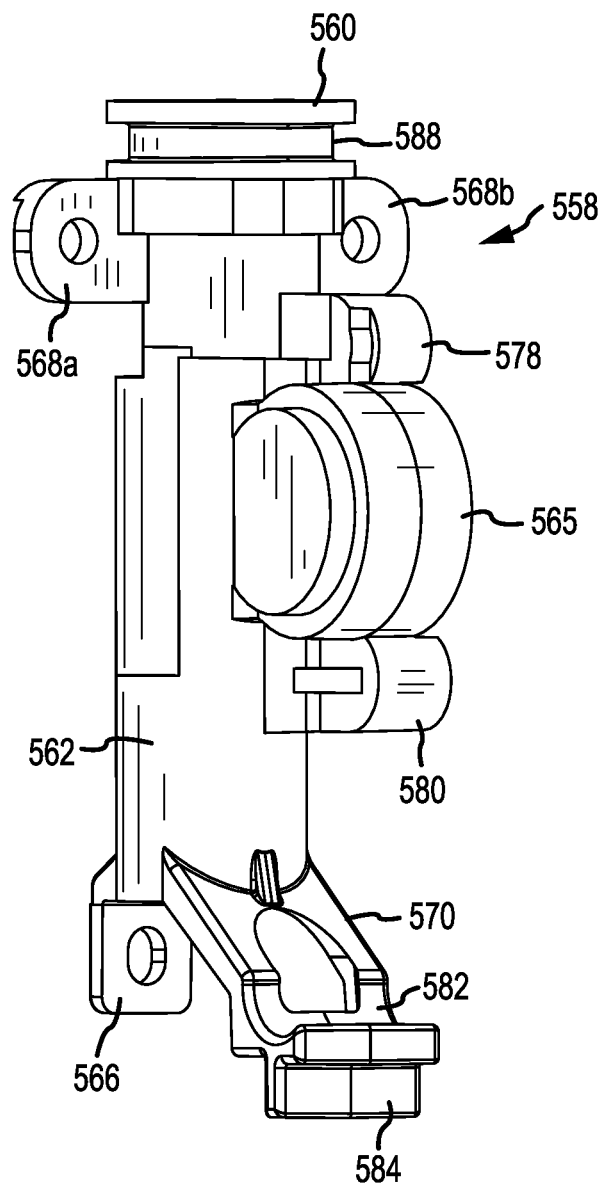
FIG. 32B is a rear isometric view of the primary valve.
Figure 33:
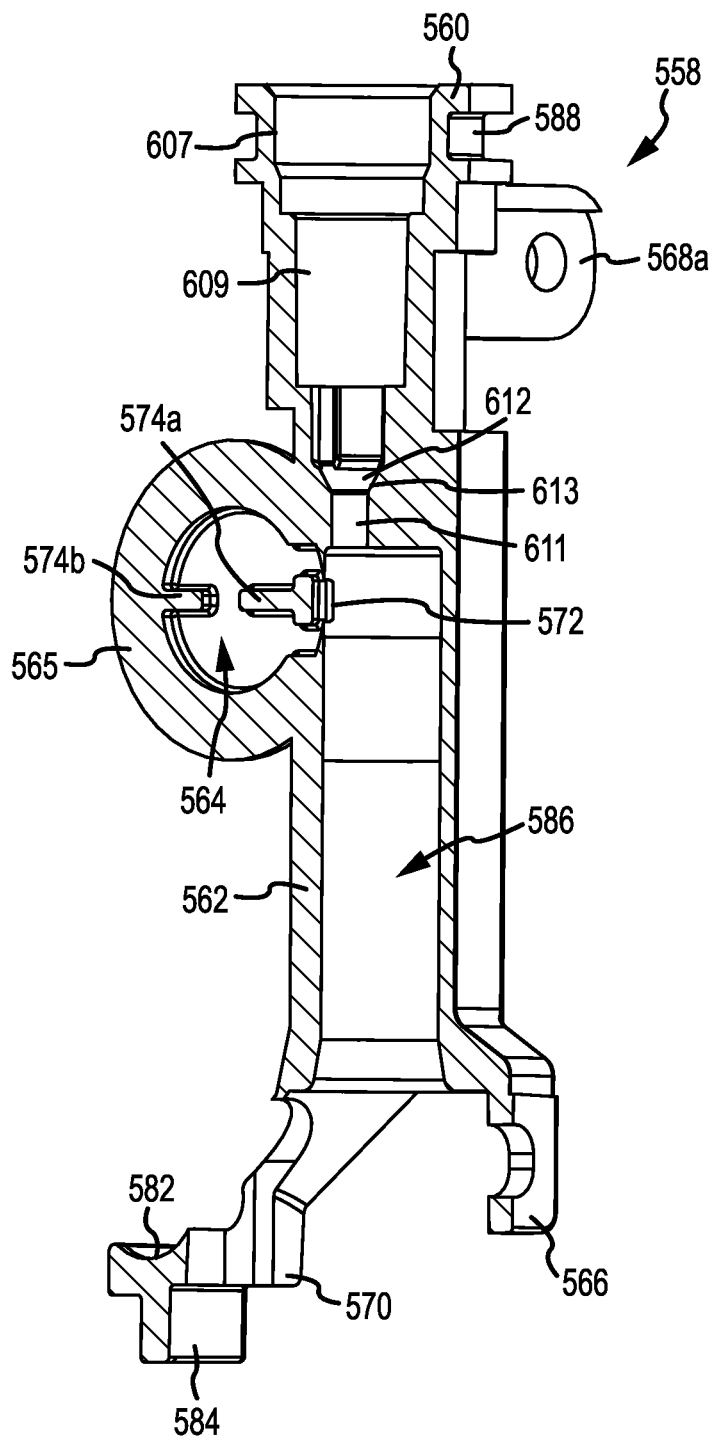
FIG. 33 is a partial cross-section view of the primary valve taken along line 33-33 in FIG. 32B.

The primary valve 558 will now be discussed in more detail. FIGS. 32A and 32B illustrate various isometric views of the primary valve. FIG. 33 is a partial cross-section view of the primary valve taken along line 33-33 in FIG. 32B. The primary valve 558 may have a primary valve body 562 and a reed valve body 565. The primary valve body 562 may also include one or more attachment brackets 568a, 568b, and 566. The attachment brackets 568a, 568b may be used to connect the primary valve body 562 to a tip connector 649 (described in detail below) and the bracket 566 may be used to connect the primary valve body 562 to the water flosser housing 385. Fasteners such as set screws may be used to fasten the attachment brackets 568a, 568b, 566 to the structures indicated above. One or more attachment bosses 578a, 578b may be appended to the reed valve body 565 for attachment of a pressure control valve assembly 492 (described in detail below). Fasteners such as set screws may be received within the bosses 578a, 578b.

A blocking arm 570 may extend at an angle outward from a lower end of the primary valve body 562. The blocking arm 570 may include a hose cradle 582 formed on upper surface thereof near a distal end of the blocking arm 570. An alignment tab 584 may extend from a bottom surface of the blocking arm 570 beneath the hose cradle 582. The alignment tab 584 may engage with a top end of the chassis 398 to align the primary valve 558 and the motor 412.

Figure 37:
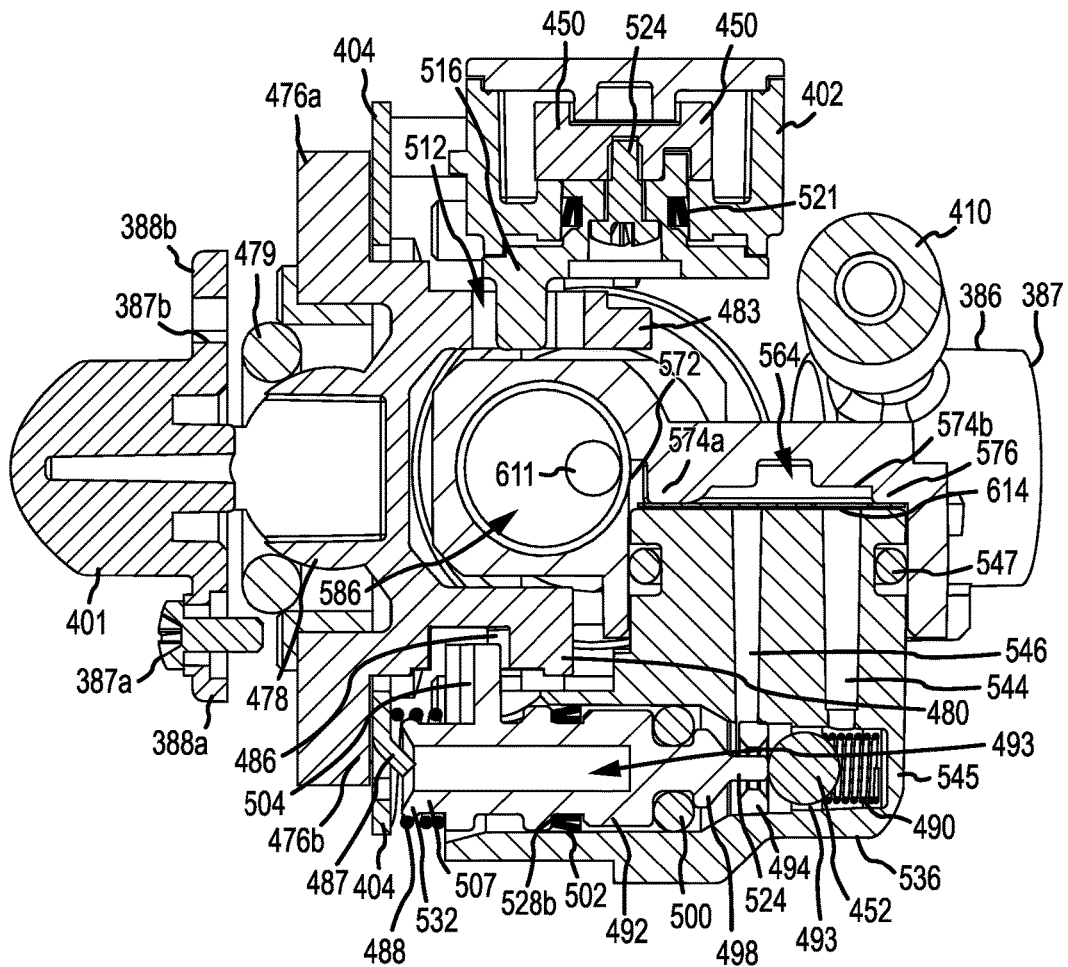
FIG. 37 is a cross-section view of the water flosser taken along line 37-37 in FIG. 19B.

The primary valve body 562 defines a primary valve chamber 586, which may be open at a bottom end to receive the pump piston arm 434 and the piston ball 426. An inlet port 572 (which is also the same as an outlet port from a chamber within the reed valve body 565 further described below) may be defined in a sidewall of the primary valve chambers 586 (as shown in FIGS. 33 and 37). An end wall opposite the bottom end may define an outlet port 611 (as shown in FIG. 33), which may be offset from the center axis of the primary valve chamber 586 (as shown in FIG. 37). A generally cylindrical backflow valve chamber 612 may be defined within the primary valve body 562 positioned immediately above and in fluid communication with the outlet port 611. A base of the backflow valve chamber 612 may be formed as a frustum that tapers between a larger diameter of the backflow chamber 612 to a smaller diameter of the outlet port 611. A generally cylindrical tip receiver section 609 may also be defined within the primary valve body 562 immediately above and in fluid communication with the backflow valve chamber 612. In the embodiment shown in FIG. 33, the tip receiver section 609 may be of a larger diameter than the diameter of the backflow valve chamber 612. A generally cylindrical collar receiver section 607 may further be defined within the primary valve body 562 immediately above the tip receiver section 609. The collar receiver section 607 may be of a larger diameter than the diameter of the tip receiver section 609. The collar receiver section 607 and the tip receiver section may together define the tip port 560.

With reference to FIG. 22, a shuttle 590 may be positioned within the primary valve chamber 586. FIG. 34 is an isometric view of the shuttle 590. FIG. 35 is a cross-section view of the shuttle 590 taken along line 34-34 in FIG. 33. With reference to FIGS. 34 and 35, the shuttle 590 may be a generally cylindrically shaped body with a crown 592 formed by a crown ring 596, which may be an annular perimeter wall formed on a top surface of the shuttle 590. An annular recess 598 may be defined top surface of the crown 592 between the crown ring 596 and a center portion of the crown 492.

As shown in FIG. 35, a piston pocket 594 may be defined as a cavity within the shuttle 590 having a frusto-spherical portion 594a that is configured to correspond to the outer diameter of the piston ball 426. The piston pocket 594 may be configured to snap-fit about the piston ball 426 to operably secure to the two components together such that the piston ball 426 may pivot within the piston chamber 594. The outer wall of the shuttle defining the piston pocket 594 may extend past the piston ball 426 to define a generally cylindrical portion 594b of the piston pocket 594 that receives a portion of the piston pump arm 434 within the piston chamber 594. The shuttle 590 may create a fluid tight seal with the inner wall of the primary valve chamber 586.

On an opposite end, the primary valve body 562 may have an open end forming a tip port 560. The tip 382 is operably connected to the tip port 560 and thereby fluidly connected to the primary valve 558. The primary valve body 562 may include an annular groove 588 defined below the tip port 560 to receive an O-ring or other sealing member to create a fluid tight seal with respect to the housing 385.

Back Flow Valve

Figure 26:
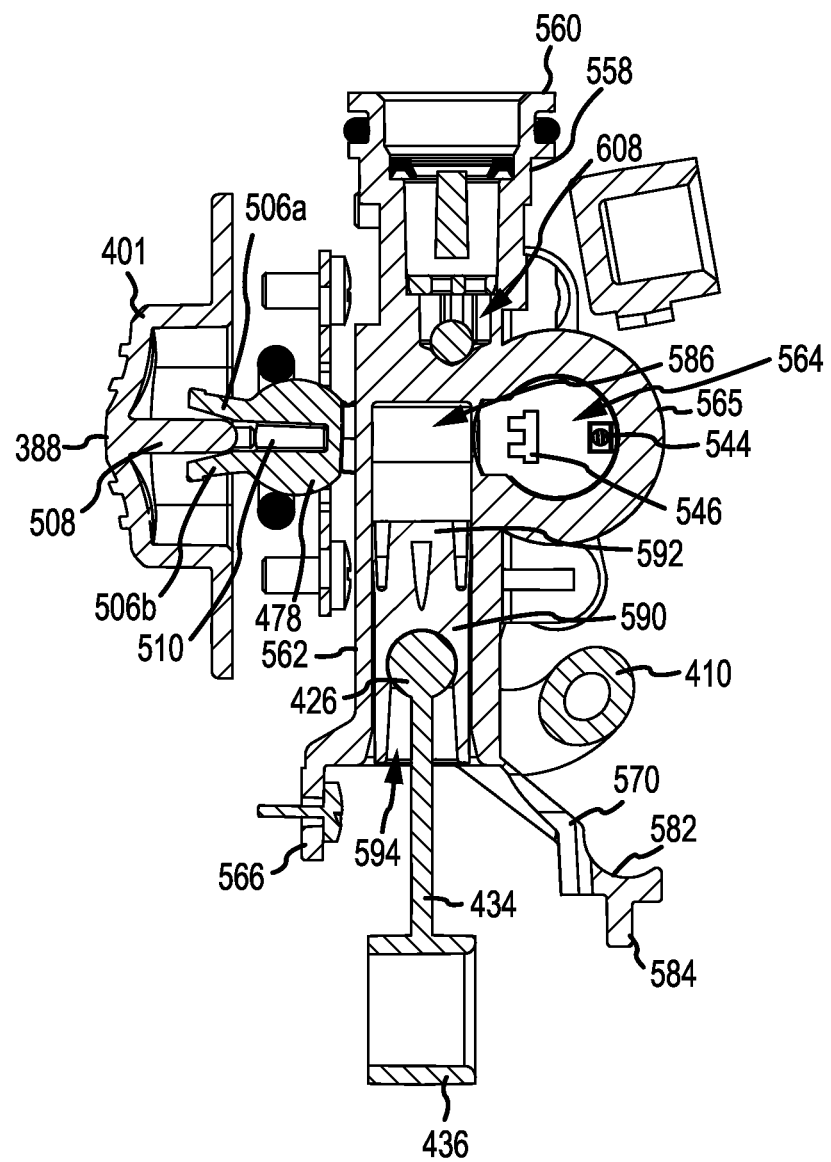
FIG. 26 is an enlarged cross-section view of the water flosser taken along line 26-26 in FIG. 19B with certain elements hidden for clarity.

With reference to FIG. 26, in some implementations, a back flow valve 608 may be used in the primary valve 588. The back flow valve 608 may help prevent water and other fluids within the tip 382 from flowing into the primary valve chamber 586. The black flow valve 608 may include a backflow ball 610 within the backflow chamber 612 located above the primary valve chamber outlet port 611 and a ball stop plate 600 positioned within the base of the tip receiver section 609. The backflow ball 610 may be of a larger diameter than the diameter of the outlet port 611 such that the backflow ball 610 cannot enter the primary valve chamber 586. The ball stop plate 600 may retain the backflow ball 610 within the backflow chamber 612.

Figure 36A:
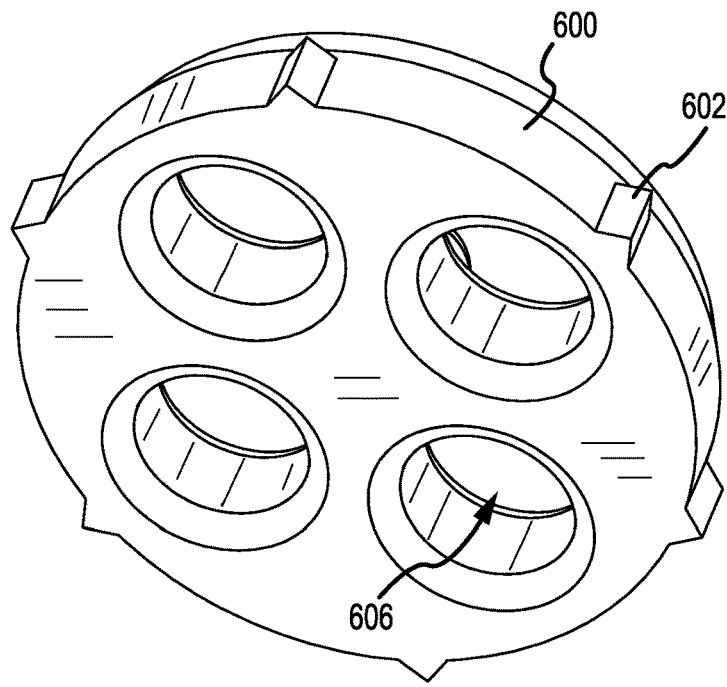
FIG. 36A is a top isometric view of a ball stop plate.
Figure 36B:
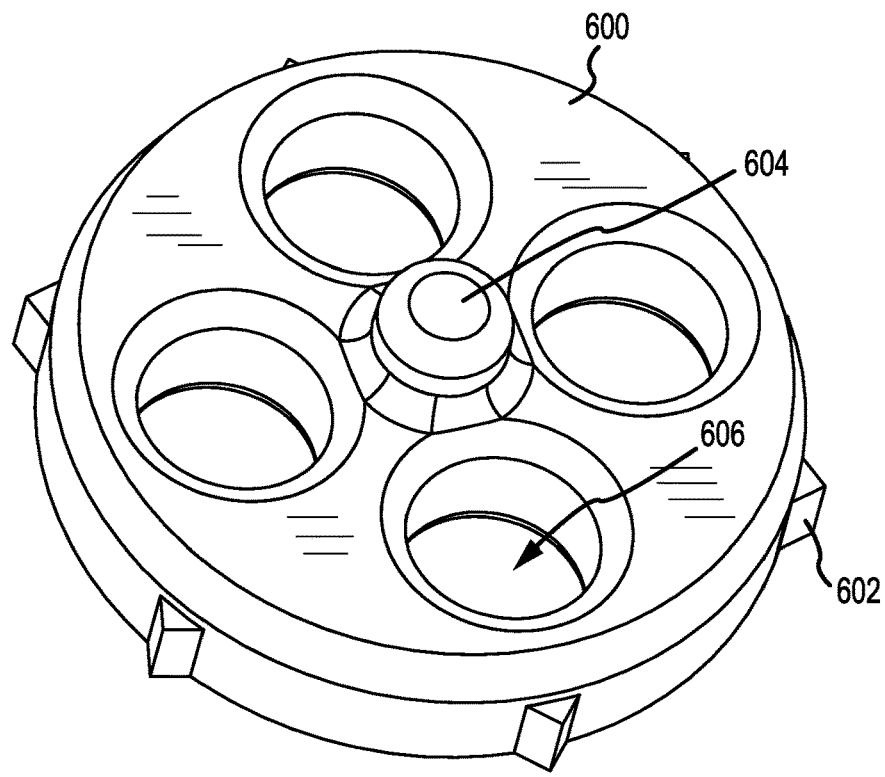
FIG. 36B is a bottom isometric view of the ball stop plate.

FIG. 36A is a top isometric view of the ball stop plate 600. FIG. 36B is a bottom isometric view of the ball stop plate 600. The ball stop plate 600 may include one or more flow apertures 606 defined therethrough. The flow apertures 606 may provide fluid communication with the tip 382 and, when the backflow ball 610 is not seated, the primary valve chamber 586. The number and size of the flow apertures 606 may be varied based on the desired water flow to the tip 382. As shown in the exemplary embodiment of FIGS. 36A and 36B, there may be four flow apertures 606. The ball stop plate 600 may further include a plurality of retention nubbins 602 defined an outer side surface thereof. The orientation nubbins 602 may grip the internal walls of the back flow chamber 612 to retain the ball stop plate 600 in position. A ball stopper 604 may be defined on a bottom of the ball stop plate 600. The ball stopper 604 may be a protrusion that extends outwards from the bottom surface of the ball stop plate 600.

Reed Valve

A reed valve body 565 may extend from one side of the primary valve body 562. The reed valve body 565 may define a generally cylindrical reed valve chamber 564 that may receive a flap valve, such as a reed valve 614 (see FIGS. 37 and 38). The reed valve chamber 564 may be sufficiently sized cavity to allow a portion of the reed valve 614 (e.g., the flap) to move laterally within the chamber so as to open and close a fluid port or channel, as described in more detail below.

The reed valve chamber 564 may include a retaining track 576 that may extend around an interior wall of the reed valve chamber 564. In some embodiments, the retaining track 576 may extend only partially around the interior sidewall of the reed valve chamber 564, and thus may form a "C" shape. Additionally, the reed valve chamber 564 may include one or more retaining nubbins 574a, 574b that extend from a rear interior surface of the reed valve chamber 564. The retaining nubbins 564a, 574b may help to retain the reed valve 614 within the reed valve chamber 564, but may also help to prevent the flap of the reed valve 614 from over extending when in the open position, discussed in more detail below.

Figure 38:
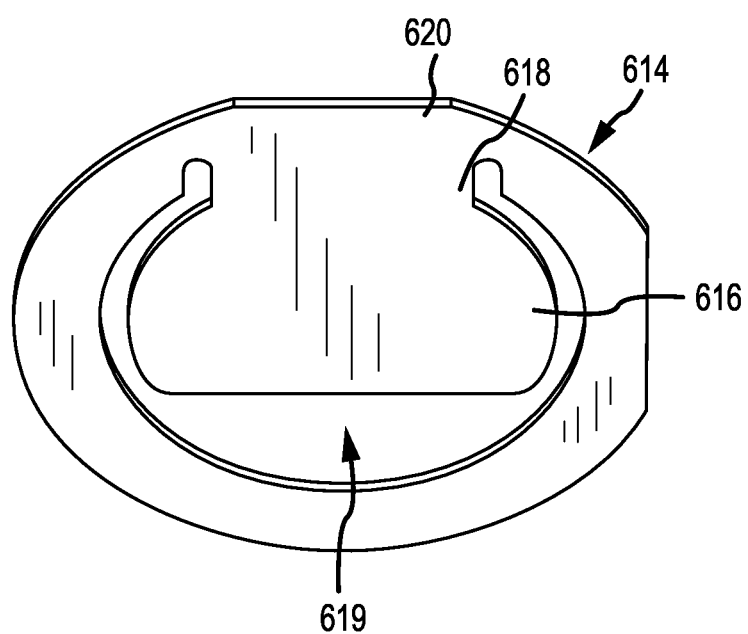
FIG. 38 is an isometric view of a reed valve.

As mentioned above and shown in FIGS. 33 and 37, an inlet port 572 to the primary valve chamber 558 is the same as an outlet port 572 of the reed valve chamber 564 which may be located beneath the lower retaining nubbin 574a in the reed valve chamber 564. FIG. 37 is a cross-section view of the water flosser 102 taken along line 37-37 in FIG. 19B showing the reed valve 614 in place within the reed valve chamber 564. FIG. 38 is a isometric view of an exemplary embodiment of a reed valve 614.

The reed valve 614 may include a flap 616 connected by a living hinge 618 to a perimeter flange 620. The flap 616 may have a semicircular shape with a distal straight edge and a curved proximal edge that transitions into the living hinge 618. Except for where connected by the living hinge 618, the flap 61 may be separated from the perimeter flange 620 by a separation space 169 allowing the flap 614 to move relative to the perimeter flange 620.

Switch and Control Assembly

Figure 24A:
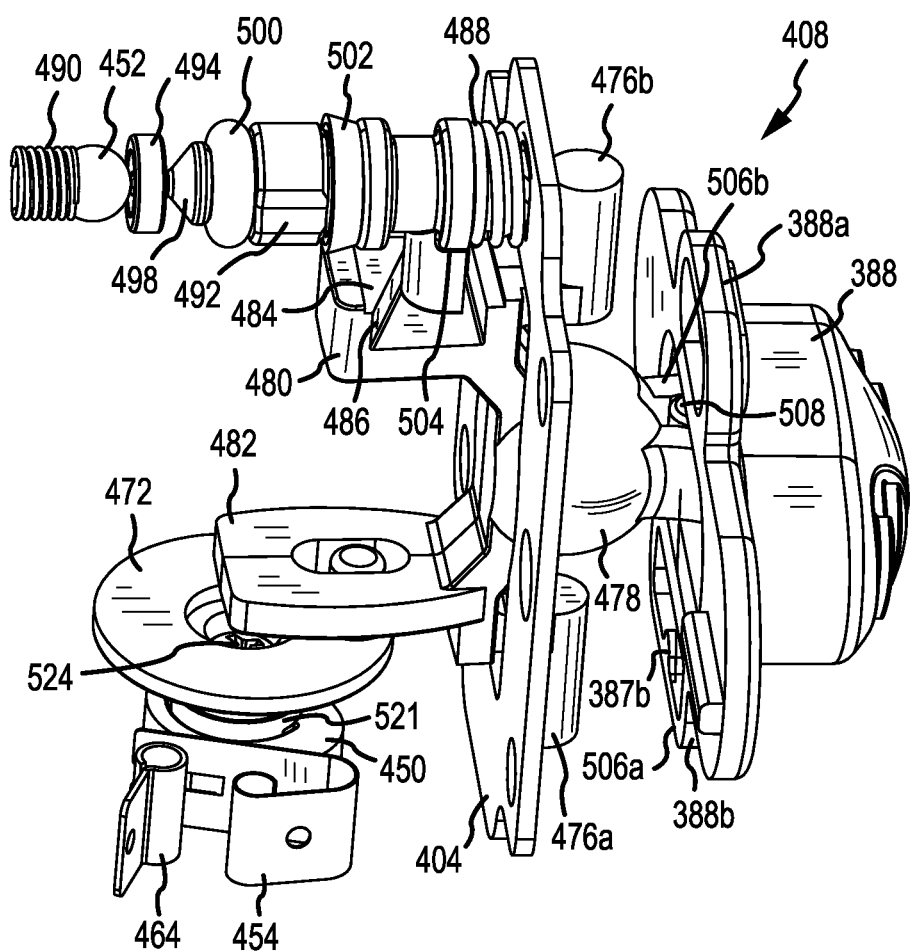
FIG. 24A is a bottom isometric view of the control assembly of the water flosser.
Figure 24B:
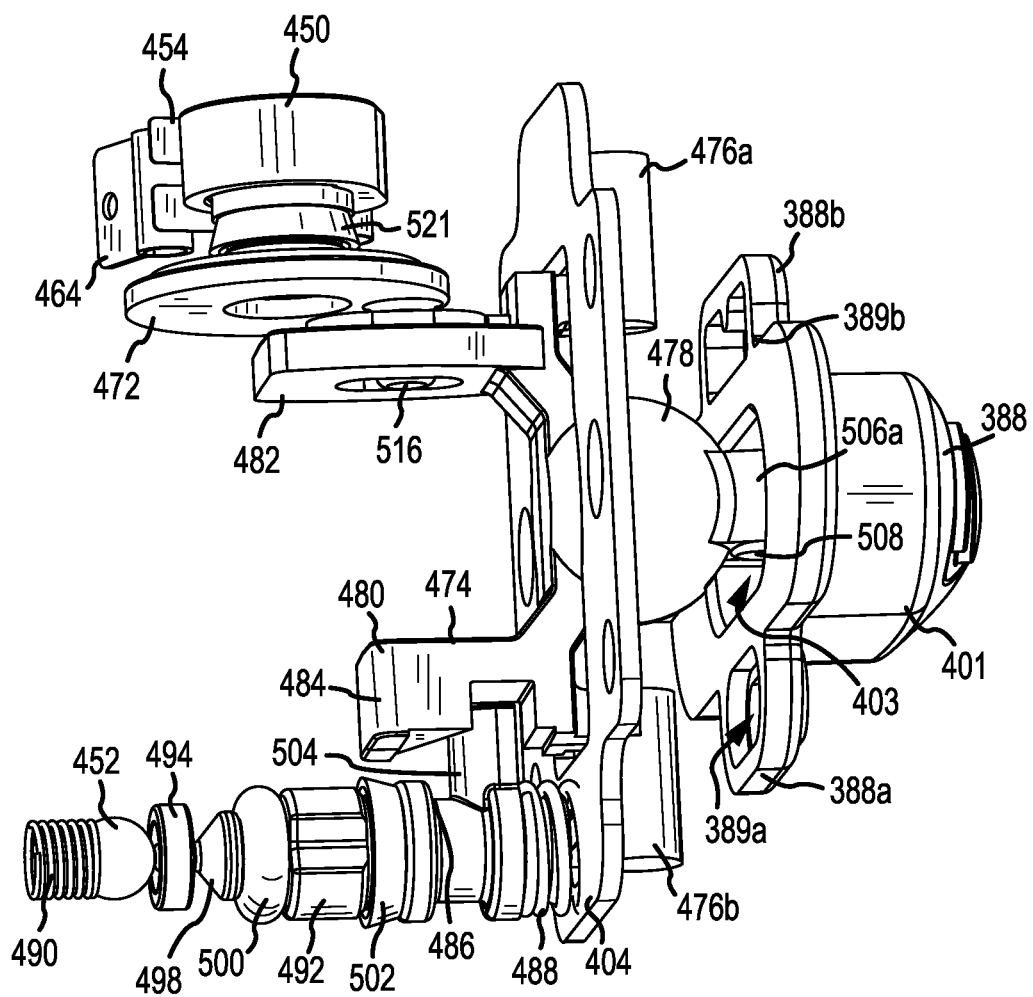
FIG. 24B is a top isometric view of the control assembly.

The switch 388 and corresponding control assembly 408 will now be discussed in more detail. FIGS. 24A and 24B are different isometric views of the control assembly 408 with select components removed for clarity. In this exemplary implementation, the switch 388 has a button portion 401 configured to protrude through an oblong aperture in the housing 385, allowing for a linear sliding actuation movement of the switch 388 by a user. A cavity 403 may be defined within the switch 388 underneath the button portion 401. A switch finger 508 extends outward from within the middle of the cavity 403 underneath the button portion 401 of the switch 388. The switch 388 may further have two flanges 388a, 388b extending from the lateral, long sides of the switch 388, each of which defines a generally linear slot 389a, 389b therein. As depicted in FIG. 20A, a set screw 387a may be inserted through one of the linear slots 389a in a first flange 388a to connect the switch 388 to a switch plate 404 that forms a part of a framework for the control assembly 408. The set screw 387a does not pull the first flange 388 tight against the switch plate 404, thereby allowing the switch 388 to move linearly with respect to the switch plate 404. A small tooth 387b may extend inward within the linear slot 389b in the second flange 388b from a sidewall of the linear slot 389b. The tooth 387b is configured to interface with a set of opposing ratchet teeth in a tab (not shown) extending from and inner wall of the housing 385. In an exemplary embodiment, there may be at least two ratchet teeth defining a groove in between in which the tooth 378b may rest in an intermediate position. The tooth 378b may also rest on either side of the tab, thereby providing three possible positions for the switch 388.

Figure 25A:
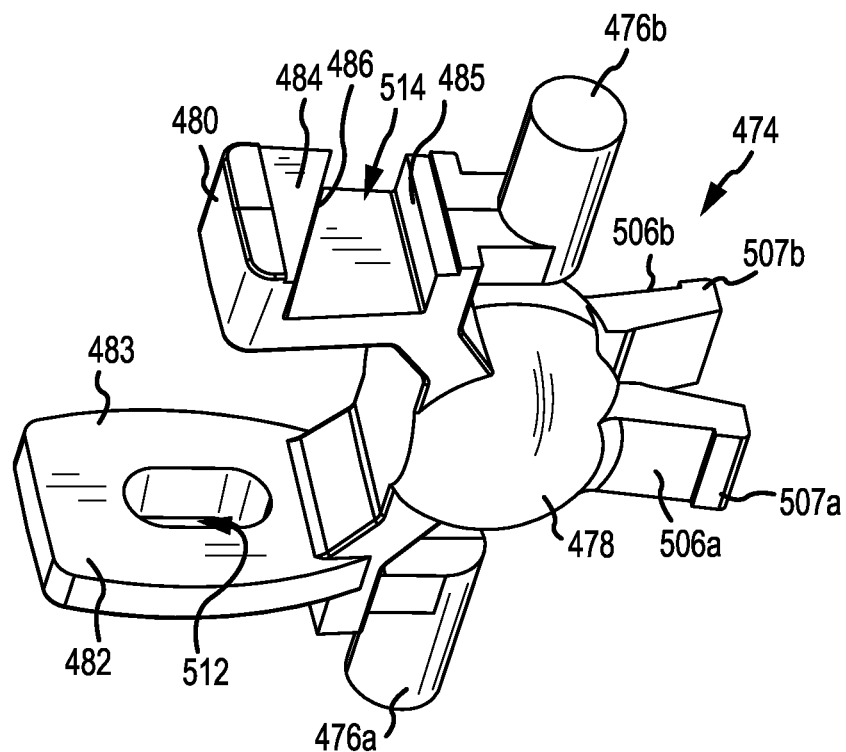
FIG. 25A is a bottom isometric view of a pivot connector of the control assembly.
Figure 25B:
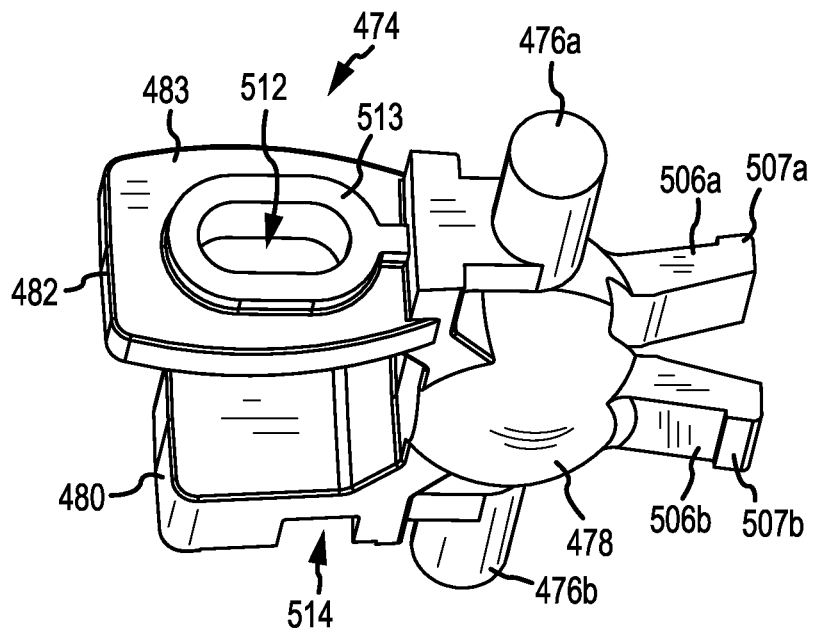
FIG. 25B is a top isometric view of the pivot connector.

With reference to FIGS. 23, 24A, and 24B, the switch 388 may effectuate control of fluid flow through the water flosser by actuating both electrical mechanical components through a pivot connector 474. FIG. 25A is an isometric view of the pivot connector 474 from a first side. FIG. 25B is an isometric view of the pivot connector from a second side. The base of the pivot connector 474 may be formed as a pivot ball 478. A pair of pivot legs 506a, 506b spaced slightly apart from each other may extend outward from one side of the pivot ball 478 at a slight angle away from each other. A ball recess 510 may be defined through at least a portion of the pivot ball 478 opening between the pivot legs 506 (as best shown in FIG. 26). The ball recess 510 may be configured to receive and connect with the switch finger 508 extending from the cavity 403 defined by the switch 388. One or more tabs 507a, 507b, detents, or other securing features may be formed on the distal ends of each of the pivot legs 506 that may be configured to snap fit into the cavity 403 in the bottom of the switch 388 on either side of the switch finger 508. An O-ring 479 may be positioned on the pivot ball 478 beneath the pivot rods 476a, 476b and above the pivot legs 506 and interface with a molded structure on an inner wall of the housing 385 that extends between the switch 388 and the pivot ball 478 to provide a seal between the pivot connector 474 and the housing 385 around an opening in the housing 385 provided for the switch 388.

A switch control arm 482 and a valve control arm 480 extend from the pivot ball 478 in substantially opposing orientations from the pivot legs 506a, 506b. In some embodiments, the switch control arm 482 and the valve control arm 480 may extend outwards from either side of a top of the pivot ball 478. Two pivot rods 476a, 476b extend laterally outward in opposite directions from the bottoms of each of the switch control arm 482 and the valve control arm 480. As shown in FIGS. 24A and 24B, the switch control arm 482 and the valve control arm 480 may extend through an opening 404a in the switch plate 404 while the pivot rods 476a, 476b are positioned on a bottom side of the switch plate 404. The pivot rods 476a, 476b may have a circular cross section that are configured to roll back and forth on the bottom side of the switch plate 404 and within respective arcuate channels molded on the inside wall of the housing 385 that hold the pivot rods 476a, 476b against the switch plate 404.

The switch control arm 482 extends above a first of the pivot rods 476a above the switch plate 404 generally in the form of a slab 483 or wall. A lever slot 512 is formed as an oblong aperture in the slab 483 such that the long walls of the lever slot 512 are oriented perpendicular to the plane of the switch plate 404. An inner side of the slab 483 may be generally planar while a raised wall may be formed around a perimeter of the lever slot 512 on an outer side of the slab 483 to act as a spacer between other components as will be described later herein.

The valve control arm extends above a second of the pivot rods 476b above the switch plate 404 generally in the form of a block 485. An inner side of the block 485 may be generally planar. An outer side of the block 485 may define a cam recess 514 bounded on lower and upper sides by a planar bottom wall 485 and a cam surface 486, respectively. The lateral sides of the cam recess 514 may be open. The cam surface 486 may be a planar surface formed at an angle with respect to the plane of the bottom wall 584. Thus, one of the open lateral sides of the cam recess 514 is wider than the opposing open side.

Figure 27A:
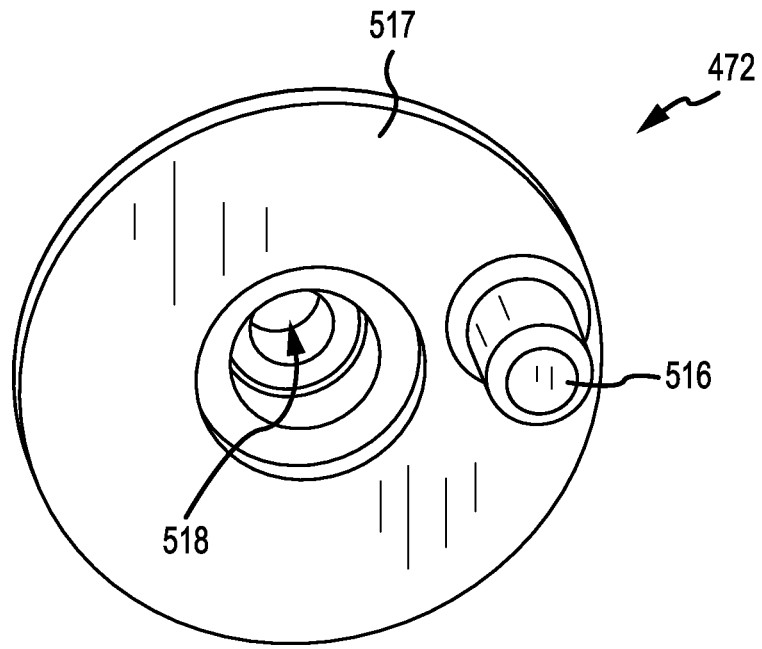
FIG. 27A is a front isometric view of a switch driver of the control assembly.
Figure 27B:
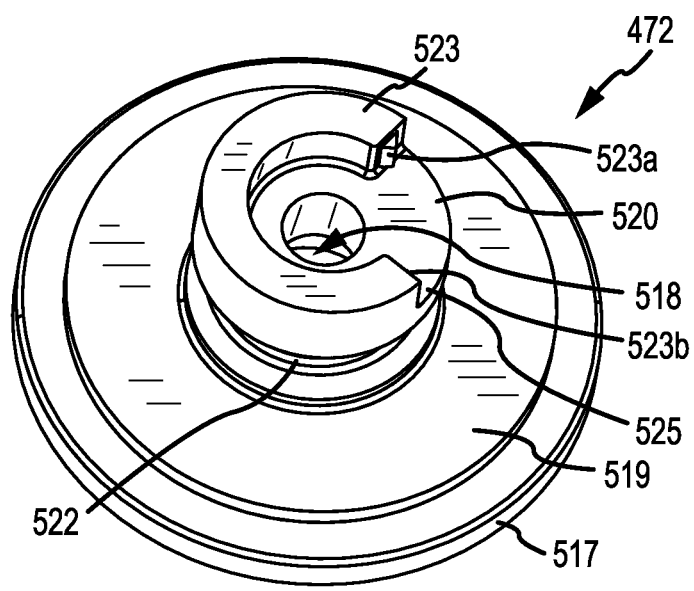
FIG. 27B is a rear isometric view of the switch driver.

As shown in FIGS. 24A and 24B, a switch driver 472 operably connects the switch control arm 482 to components housed within the switch box 402, which will be described in greater detail below. The switch driver 472 is shown in isolation in FIGS. 27A and 27B. A driver disk 472 forms the core of the switch driver 472 and is a generally flat disk. A fastener aperture 518 is formed through a center of the driver disk 517. A driver post 516 extends from a flat surface of the driver disk 517 on an inner side of the switch driver 472. The driver post 516 fits within the lever slot 512 of the switch control arm 482 of the pivot connector 474, thereby mechanically coupling the switch driver 472 and the pivot connector 474.

A switch cam coupler 520 extends generally as a post from an outer side of the driver disk 517. The fastener aperture 518 is defined through the center of the switch cam coupler 520. A raised annular platform 519 with a smaller diameter than a diameter of the driver disk 517 provides a stepped surface on the outer side of the driver disk 517 and the switch cam coupler 520 extends above the platform 519. An annular groove 522 is defined in a sidewall of the switch cam coupler 520 and is configured to receive a cup seal 521 or other seal structure (as shown in FIGS. 24A and 24B) that provides a seal between the switch driver 472 and the switch box 402. A lever key 523 may be formed on a top surface of the switch cam coupler 520 and configured as a C-shaped wall having a width measured radially from an outer edge of the switch cam coupler 520 to an inner edge of the lever key 523 that is spaced apart from the fastener aperture 518. A generally annular, recessed platform 525 is thereby defined around the fastener aperture 518 at the base of the lever key 523 and further extends radially outward as a wedge-shaped surface between the ends of the C-shaped wall forming the lever key 523 to the outer diameter of the switch cam coupler 520. Retention nubbins 523a, 523b may also protrude from each end of the lever key 523.

The switch box 402 may house one or more actuation components. In the exemplary implementation shown in FIG. 23, the switch box 402 is a generally rectangular and at least partially hollow housing. The switch box 402 may further include one or more anchoring flanges 466 extending from one or more sides to connect the switch box 402 to the water flosser housing 385. One or more fasteners 468, 470, e.g., screws, may be used to secure the anchoring flanges 466 to the housing 385 and mount the switch box 402 in position. An aperture formed in the back wall of the switch box 402 receives the switch cam coupler 520, which extends therethrough into the switch box 402. An annular wall 451 may extend from the back wall of the switch box 402 around the aperture as shown in FIGS. 21 and 22. As previously noted, the cup seal 521 around the switch cam coupler 520 provides a fluid tight seal between the switch cam coupler 520 and the annular wall 451 in the switch box 402.

Figure 27C:
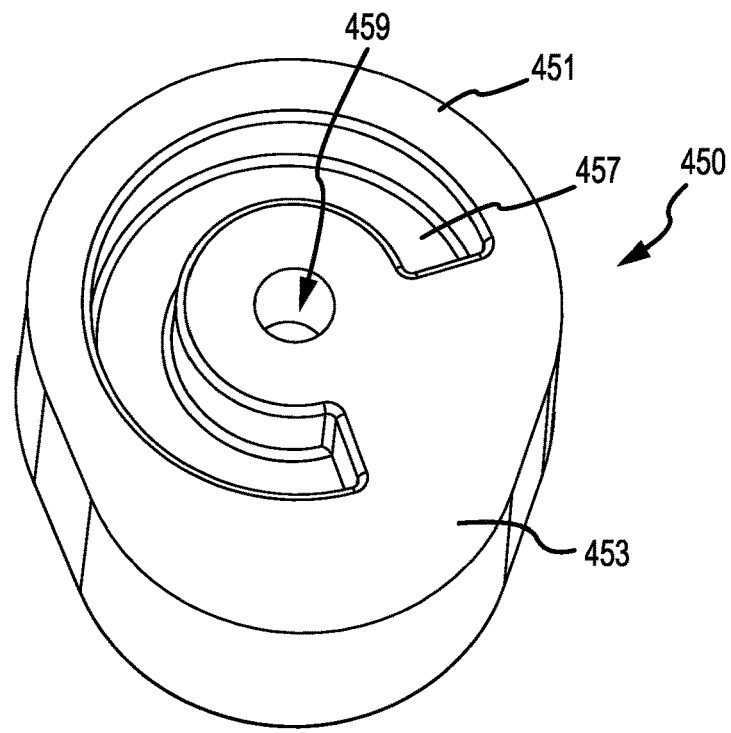
FIG. 27C is a front isometric view of a switch cam of the control assembly.
Figure 27D:
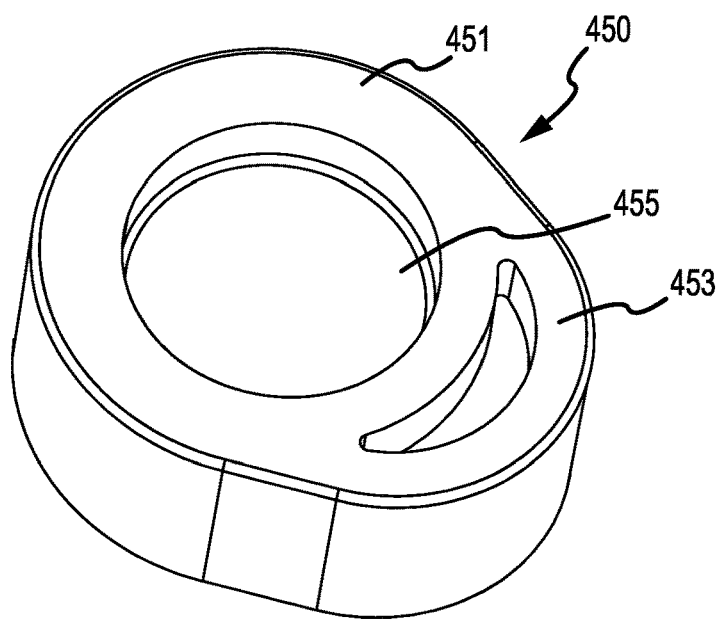
FIG. 27D is a rear isometric view of the switch cam of the control assembly.

A switch cam 450 is mounted on the top of the switch cam coupler 520 extending through the back wall of the switch box 402. As shown in detail in FIGS. 27C and 27D, the switch cam 450 may be a slab having a generally oblong, pear-shaped form with a larger base portion 451 that tapers to a narrower compression portion 453. A circular depression 455 may be formed in the top side of the switch cam 450. A C-shaped keyway channel 457 may be formed in at bottom surface of the switch cam 450. A fastener receiver 459 may be formed as cylindrical cavity in the bottom surface of the switch cam 450 centered within the C-shape of the keyway channel 457.

The switch cam 450 may be mounted on the switch cam coupler 520 such that the lever key 523 fits within the keyway channel 457 on the bottom side of the switch cam 450. The retention nubbins 523a, 523b on the ends of the lever key 523 may be slightly compressed against the walls of the keyway channel 457 in order to create a tight friction fit between the switch cam 450 and the switch cam coupler 520. The switch cam 450 is further fastened to the switch cam coupler 520 by a fastener, e.g., a set screw (not shown) that extends from the inner side of the switch driver 472 through the fastener aperture 518 and engages the fastener receiver 459 in the bottom side of the switch cam 450. In this manner, the switch cam 450 and the switch driver 472 are connected in a fixed relationship. Further, a cover (not shown) may be placed on the switch box 402 to enclose the components housed therein. An annular or cylindrical boss (not shown) my extend from the inner side of the cover to fit within the circular depression 455 in the top surface of the switch cam 450 to aid in the alignment of the switch cam 450 and the driver disk 517 with respect to the switch box 402. The cover may be fastened, adhered, ultrasonically welded, or otherwise fixed to the switch box 402.

With reference to FIG. 23, the switch box 402 may also house an anchor pin 446 and a fulcrum pin 448, each extending upward as posts from the back surface of the switch box 402. The anchor pin 446 may be spatially separated from the fulcrum pin 448. The anchor pin 446 may be operably connected to a contact leaf 454 and may act to secure the contact leaf 454 to the switch box 402. In one embodiment, a first end of the contact leaf 454 may wrap around at least a portion of the outer surface of the anchor pin 446. The contact leaf 454 may then extend to wrap around at least a portion of the fulcrum pin 448 to secure it in place. A free end of the contact leaf 454 may extend beyond the fulcrum pin 448 a selected distance. In this manner the fulcrum pin 448 may support the contact leaf 454 and provide an inflection point support for the contact leaf 454.

The contact leaf 454 may be a generally rectangular strip of electrically conductive material, such as, metal, but may also be at least somewhat flexible. The width of the contact leaf 454 may provide a contact surface to compress against a contact without requiring the exact precision that could be required if, for example, the contact leaf 454 had a smaller surface area (such as a wire or the like). The contact leaf 454 is sufficiently flexible to bend into a contact position and then resiliently spring back to an original, non-contact position once the bending force is removed. In some embodiments, such as the embodiment illustrated in FIG. 23, the contact leaf 454 may be bent in a U or V shape as it wraps around the fulcrum pin 448 positioned at the inflection point.

With continued reference to FIG. 23, the switch box 402 may also include a contact pin 456. The contact pin 456 may be surrounded by an electrical contact 464, which similar to the contact leaf 454, may be composed of an electrically conductive material, such as a metal. The contact pin 456 may be spatially separated from the anchor pin 446 and the fulcrum pin 448 within the switch box 402, but may be sufficiently close to the fulcrum pin 448 such that as the free end of the contact leaf 454 is compressed, the contact leaf 454 may contact the electrical contact 464 on the outer surface of the contact pin 456.

The switch box 402 may also house two or more communication wires. A first wire 462a may be in communication with the contact leaf 454 and a second wire 462b may be in communication with the electrical contact 464 on the contact pin 456. A side end of the switch box 402 may include a sheath 458 positioned through an aperture defined through the switch box 402. The communication wires 462a, 462b may extend through the sheath 458 to exit the switch box 402. The sheath 458 guides and protects the wires 462a, 462b as they pass through the aperture within the switch box 402. The opposite ends of the communication wires 462a, 462b may be connected to the motor 412.

Figure 29:
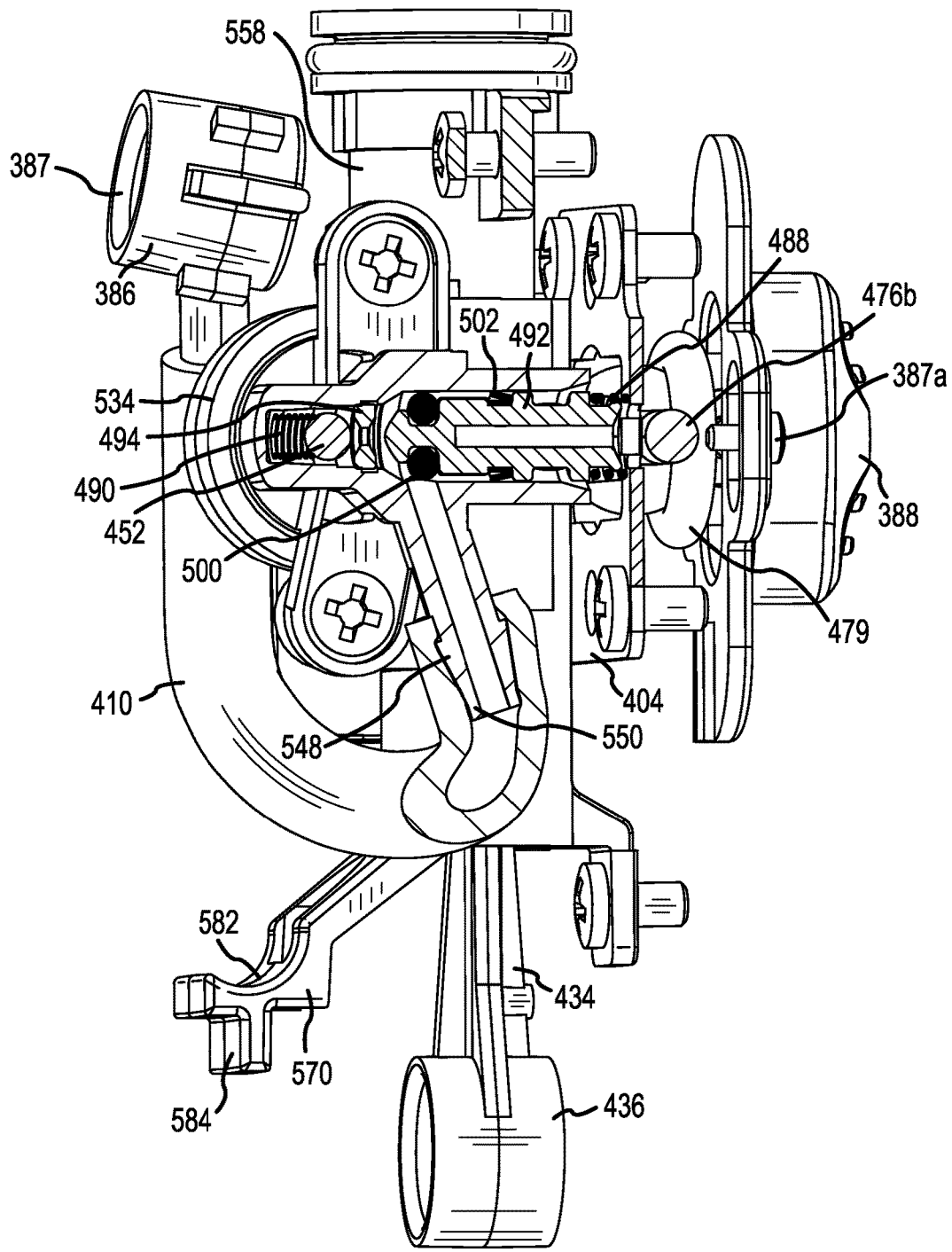
FIG. 29 is a partial cross section view of the water flosser taken along line 29-29 in FIG. 19F.
Figure 30A:
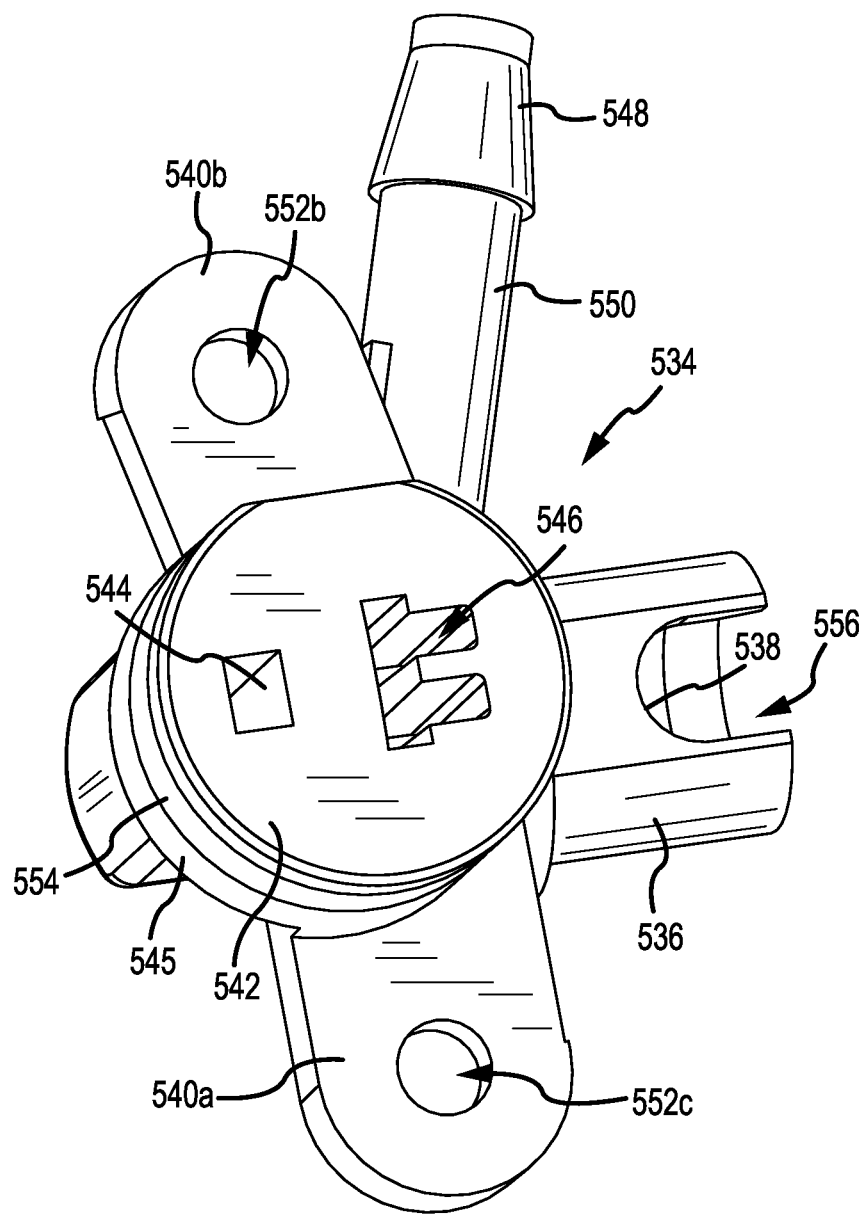
FIG. 30A is a front isometric view of a pressure control assembly.
Figure 30B:
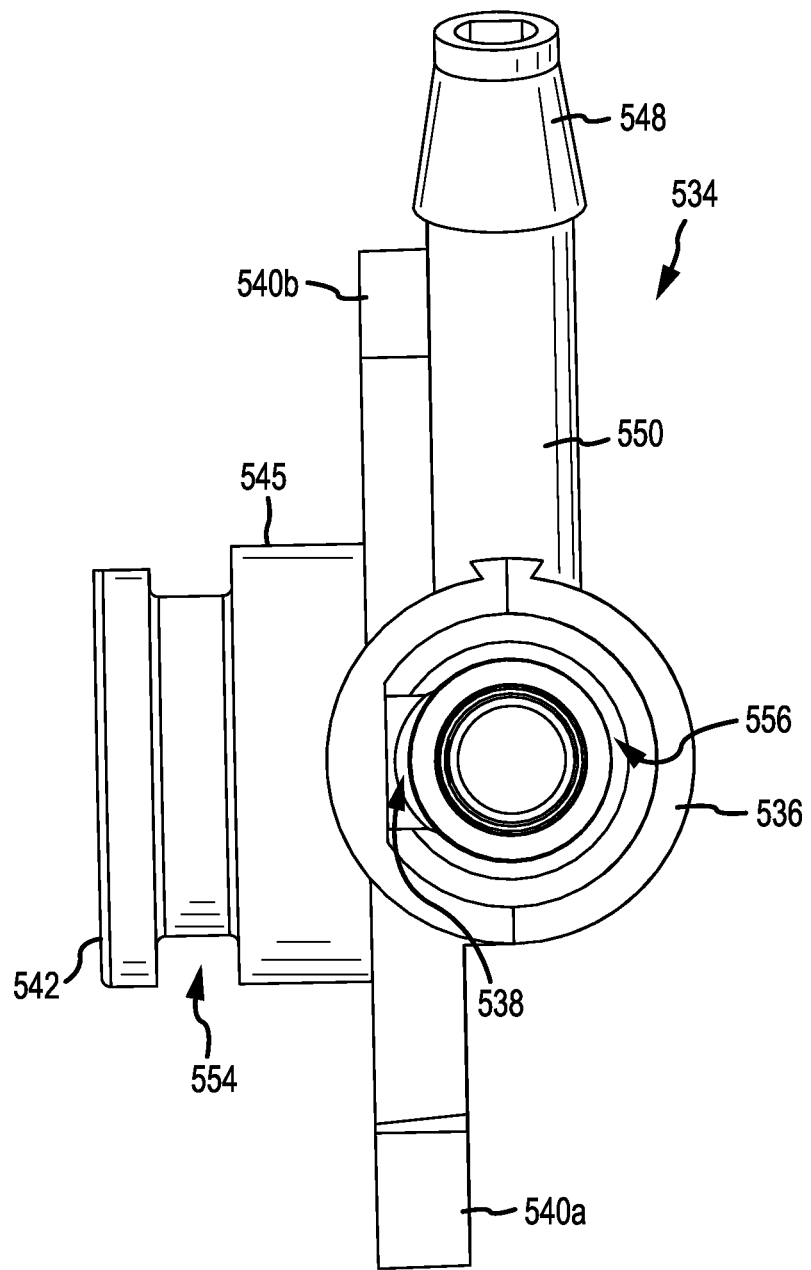
FIG. 30B is a side elevation view of the pressure control assembly.
Figure 31:
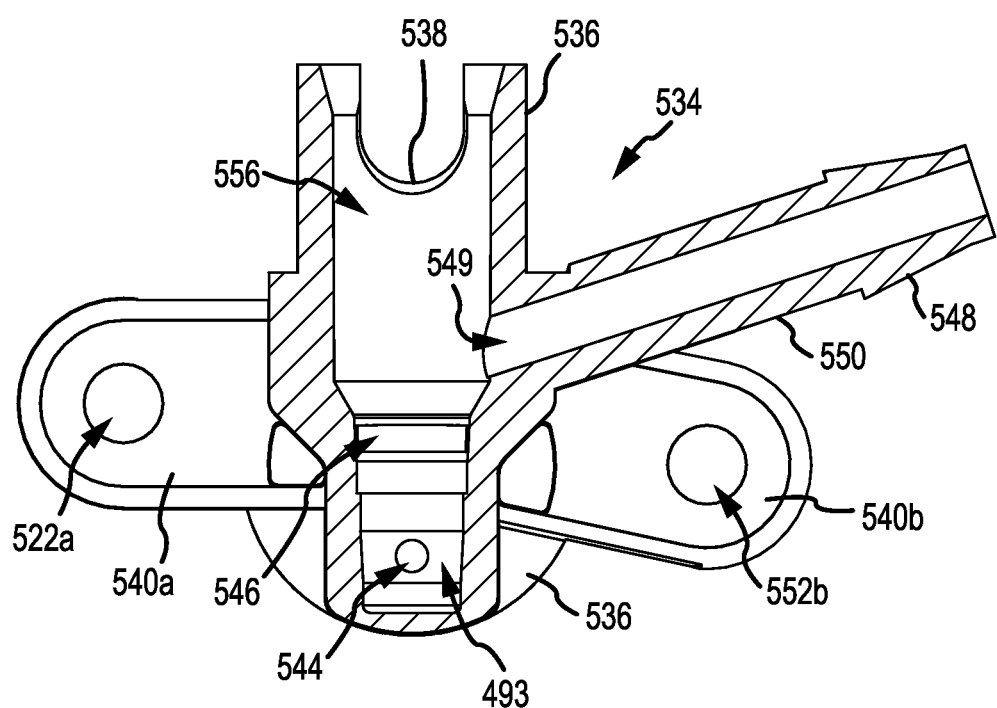
FIG. 31 is a cross-section of the pressure control assembly taken along line 31-31 in FIG. 30A.

The pressure control assembly 534 will now be discussed in more detail. A pressure control valve 492 may be received within a valve housing 536 of the pressure control assembly 534. FIG. 29 is a partial cross section view of the water flosser taken along line 29-29 in FIG. 19F, with select elements not shown for clarity. FIG. 30A is a front isometric view of the pressure control assembly 534. FIG. 30B is a side elevation view of the pressure control assembly 534. FIG. 31 is a cross-section of the pressure control assembly 534 taken along line 31-31 in FIG. 30A. The pressure control assembly 534 may include the valve housing 536 which receives the pressure control valve 492, a valve water inlet port 550, and a pressure control loop extension 545.

The valve water inlet port 550 may provide water to the valve housing 536. The valve water inlet 550 may be an elongated tubular member having a barb 548 on a terminal end. The barb 548 may function as a retaining member to provide a secure connection with the transport hose 410 as shown in FIG. 29, an opposite end of which is connected to the water flosser inlet port connector 387. In some embodiments, the transport hose 410 may vary in length e.g., due to manufacturing variances and, accordingly, may have a longer length than illustrated in the present disclosure. In such embodiments, the blocking arm 570 extending from the primary valve body 562 may provide a support surface for the transport hose 410 to prevent the transport hose 410 from interfering with the gears 430, 432.

The valve housing 536 may define a valve chamber 556, open at a bottom end and closed at a top end. The valve water inlet port 550 connects with the valve housing 536 and an aperture 549 in the valve housing 536 at this connection location provides fluid communication between the valve water inlet port 550 and the valve chamber 556 within the valve housing 536. The valve housing 536 may also define a cam arm collar 538. The cam arm collar 538 may be a U-shaped cutout or recess within the valve housing 536 that allows the cam arm 504 of the pressure control valve 492 to extend therethrough when the pressure control valve 492 is received in the valve housing 536.

Figure 28A:
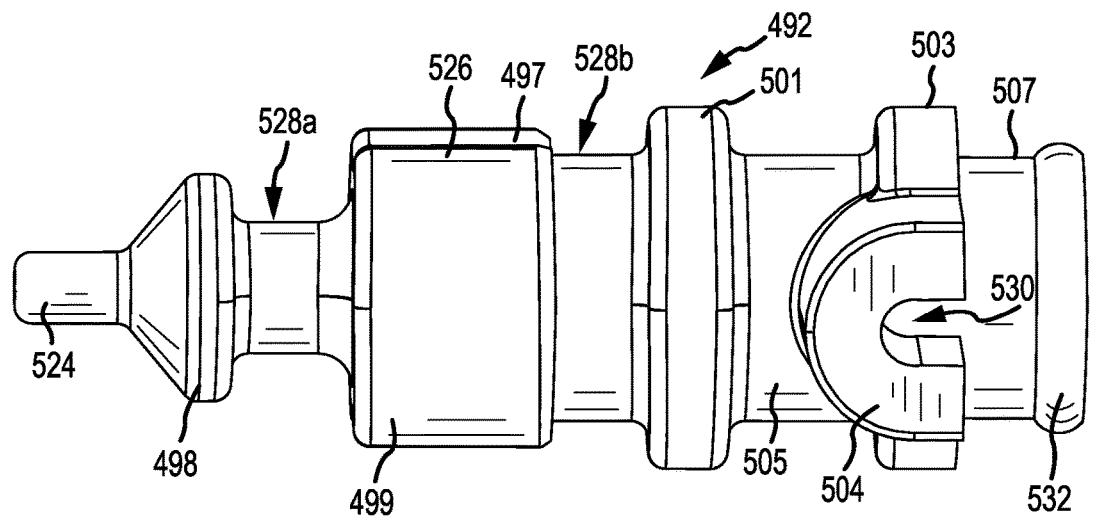
FIG. 28A is a right elevation view of a pressure control valve of the control assembly.
Figure 28B:
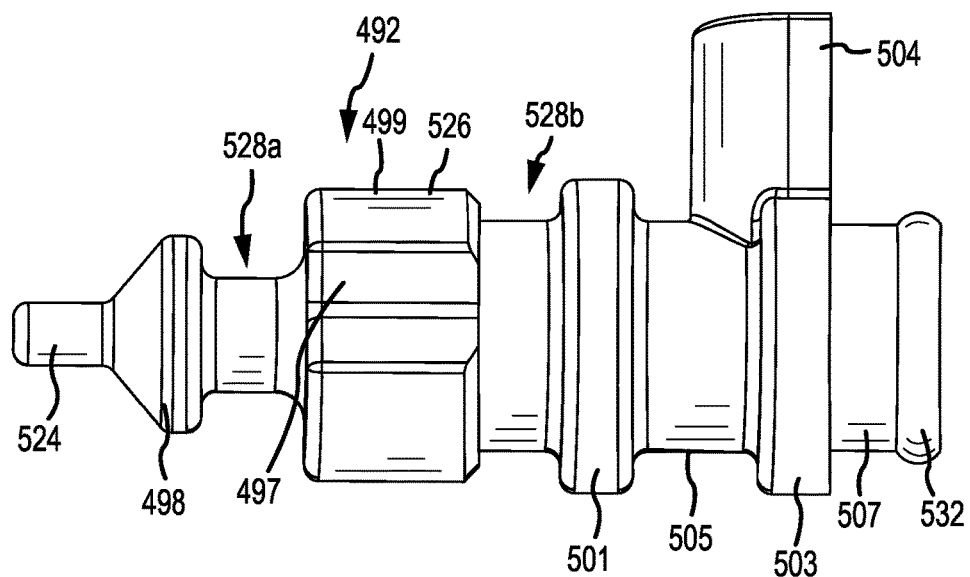
FIG. 28B is a front elevation view of the pressure control valve.

FIGS. 28A and 28B illustrate various elevation views of the pressure control valve 492, which is housed within a valve housing 536 in the pressure control assembly 534 as shown in FIGS. 29 and 37. With reference to FIGS. 24A, 24B, 28A, and 28B, the pressure control valve 492 may have a valve body 526 that is a generally cylindrical member that may define a hollow core 493. However, in other embodiments, the valve body 526 may be a solid component. Two or more annular channels 528a, 528b may be defined within an outer surface of the valve body 526. The annular channels 528a, 528b may be configured to receive one or more sealing members. The valve body 526 may have a base end 532 and a second end terminating at a nose 524. The base end 532 may formed as an annular band with a convexly curved surface between a bottom edge and a top edge of the base end 532. The nose 524 may be formed as a narrow cylindrical post that extends from a head 498 of the valve body 526. The head 498 may have a cone or frustum shape with the nose 524 extending from a narrow tip thereof.

A wide base of the frustum shape of the head 498 may assist in retaining a sealing O-ring 500 in position on the valve body 526 in a first of the annular channels 528a formed between the base of the head 498 and an upper band 499 that may be formed as a cylindrical wall with a larger diameter than the base of the head 498. The upper band 499 may further define a pair of longitudinally oriented wedges 499 in the sidewall thereof. A sealing member, for example, and O-ring 500 of a relatively large cross sectional diameter may be seated within the first annular channel 528a below the base of the head 498. The second annular channel 528b may be formed between the upper band 499 and a middle ring 501 positioned below the upper band 499. A sealing member, for example, a cup seal 502 may be seated within the second annular channel 528b. The middle ring 501 may be both narrower in width and larger in diameter than the upper band 499.

An upper shaft 505 extends below the middle ring 501 in a generally cylindrical form and may have a diameter similar to the diameter of the second annular channel 528b. The upper shaft 505 may transition into a lower ring 502 that may have a similar diameter to that of the middle ring 501. An upper edge of the lower ring 503 may be contoured while a lower edge of the lower ring 502 may be formed as perpendicular shoulder such that the lower ring 503 has a flat bottom surface that returns radially inward to interface with a cylindrical wall of a lower shaft 507 at a right angle. The lower shaft 507 may have substantially the same diameter as the upper shaft 505 and may transition into the base end 532. The curved surface of the base end 532 may extend radially further outward to an apex that has a diameter larger than the diameter of the lower shaft 507.

A cam arm 504 extends from one side of the valve body 526 generally from a position overlapping a portion of both the upper shaft 505 and the lower ring 503. The cam arm 504 may have a curved outer surface with an arm recess 530 defined on an opposite side of the curved surface. In other words, the cam arm 504 may have a horseshoe or "U" shaped cross section. The curved surface of the cam arm 504 extends into the region defined by the upper shaft 505 while the free ends of the U-shape may be aligned with the flat bottom surface of the lower ring 503. The cam arm 504 extends from the valve housing 536 of the pressure control assembly 534 to a position whereby the curved outer surface of the cam arm 504 interfaces with the cam surface 486 of the valve control arm 480 of the pivot connector 474.

As shown in FIG. 37, the base end 532 of the pressure control valve 492 may, in some configurations, extend below a bottom of the valve housing 536. A flow control spring 488 may be attached around the base end 532 and the lower shaft 507, abutting the lower ring 503. The opposite end of the flow control spring 488 may be connected to the switch plate 404. In the exemplary embodiment shown, the flow control spring 488 is embedded within the switch plate 404. An alignment clip 487 may also extend at an angle from the switch plate 404 into the hollow core 493 of the pressure control valve 492 in order to help ensure that the base of the pressure control valve 492 maintains a proper position.

As shown in FIGS. 30A and 37, the pressure control loop extension 545 may be formed at a top end of the valve housing 536 and extend laterally therefrom toward and seats within the reed valve body 565 on the primary valve 558. With reference to FIG. 30B, an annular sealing groove 554 may be defined within an outer surface of the pressure control loop extension 545. The annular sealing groove 546 may receive a sealing member, such as an O-ring 547 that seals the pressure control loop extension 545 against the interior sidewall of the reed valve body 565. The pressure control assembly 534 may be connected to the attachment bosses 578a, 578b on the primary valve 558 via a set of wings 540 or tabs extending from lateral sides of the pressure control loop extension 545. The wings 540 may include one or more fastener apertures 552 defined therethrough.

The pressure control loop extension 545 may define a loop chamber 493 positioned above the valve chamber 556 and in fluid communication therewith. A sealing washer 494 may snap fit in between the loop chamber 493 and the valve chamber 556. The sealing washer 494 may define a central aperture through which the nose 524 of the valve body 526 is configured to fit. A sealing ball 452 is configured to reside within the loop chamber 493 above the sealing washer 494. A diameter of the loop chamber 493 larger than the diameter of the sealing ball 452 while the diameter of the sealing ball 452 is larger than a diameter of the central aperture of the sealing washer 494. A pressure control spring 490 may be positioned within the loop chamber 493 above the sealing ball 452 to bias the sealing ball 452 downward toward and against the sealing washer 494.

The pressure loop extension may further define a pressure release conduit 544 and an outlet conduit 546 therein, each extending from the loop chamber 493 to exit within a sealing face 542 of the pressure control loop extension 545. The sealing face is contained within the reed valve body 565 and thus provides a wall of the reed valve chamber 564. The pressure release conduit 544 and the outlet conduit 546 may thus provide fluid communication between the loop chamber 493 and the reed valve chamber 564. In some embodiments, the outlet conduit 546 may be spatially separated form the pressure release conduit 544. An inlet end of the outlet conduit 546 may be located in an upper portion of the valve chamber 556 beneath the sealing washer 494 while the pressure release conduit 544 may be located in an upper portion of the loop chamber 493 above the sealing ball 452 as shown in FIG. 37. Similarly, the outlet conduit 546 may be located in a lower portion of the reed valve chamber 564 while the pressure release conduit 544 may be located in an upper portion of the reed valve chamber 564.

In some embodiments, the pressure release conduit 544 may be a generally rectangular shaped aperture on the sealing face 542 that may transition to a circular shaped aperture when it reaches the loop chamber 493. Similarly, the outlet conduit 546 may have a rectangular shape with two legs (e.g., shaped like the pi (Π) symbol) defined in the sealing face 542, but may transition to a generally rectangular shaped aperture as it reaches the loop chamber 493. The shape of the pressure release conduit 544 and the outlet conduit 546 may be varied based on a desired manufacturing process (e.g., molding techniques), or may otherwise be varied as desired. In some implementations, the diameter of the channels 544, 546 may affect the variation in water pressure and total water pressure produced through the tip of the water flosser 102, as will be discussed in more detail below, and so the diameters may be varied to accommodate changes in pressure as desired.

The sealing face 542 may be generally circular in form and may interface with the reed valve 614. The reed valve 614 may be positioned against the sealing face 542 of the pressure control assembly 535 and be retained in position by the retaining nubbins 574a, 574b in the reed valve chamber 564. The semicircular shape of the flap 616 of the reed valve 614 results in the reed valve covering the opening of the outlet conduit 546 in the sealing face 542 while not covering opening of the pressure release conduit 544 in the sealing face 542.

Battery Pack

Figure 39A:
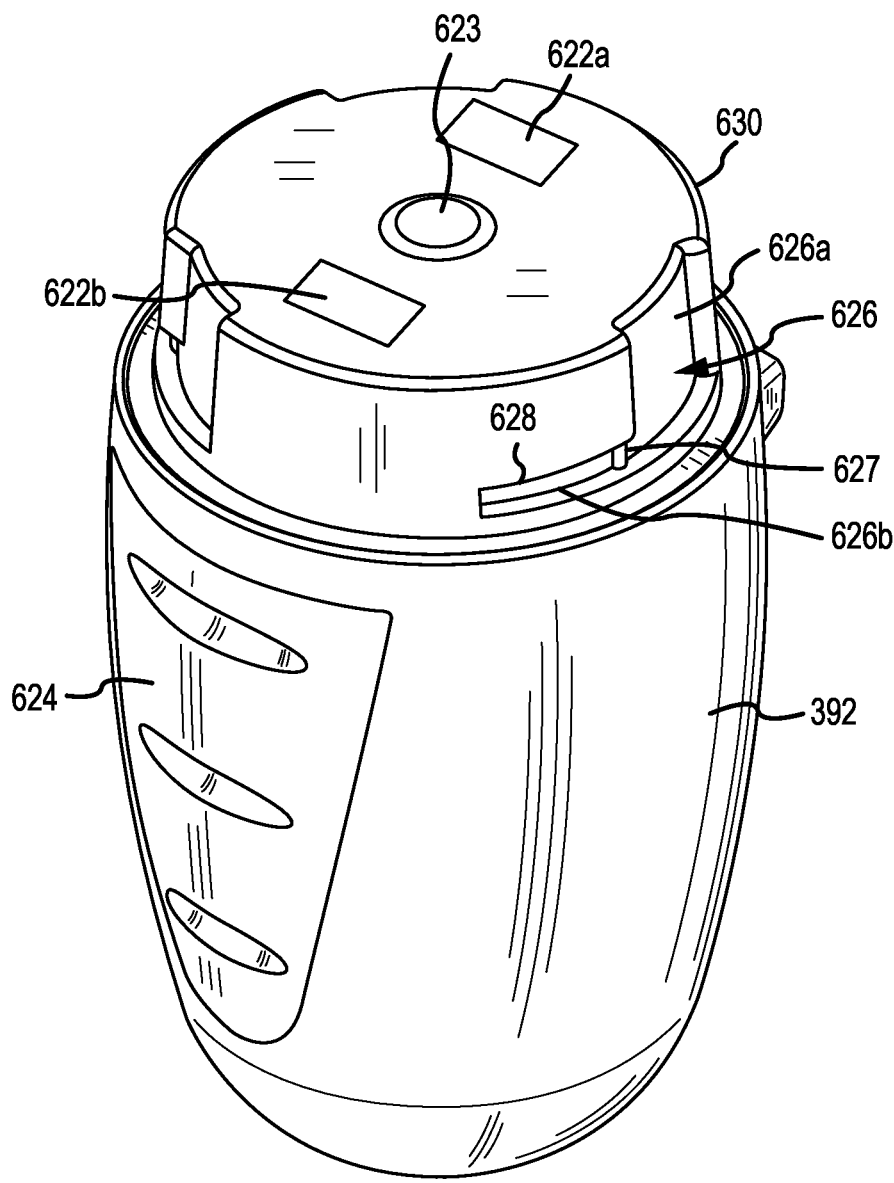
FIG. 39A is a top isometric view of a battery pack for the water flosser.
Figure 39B:
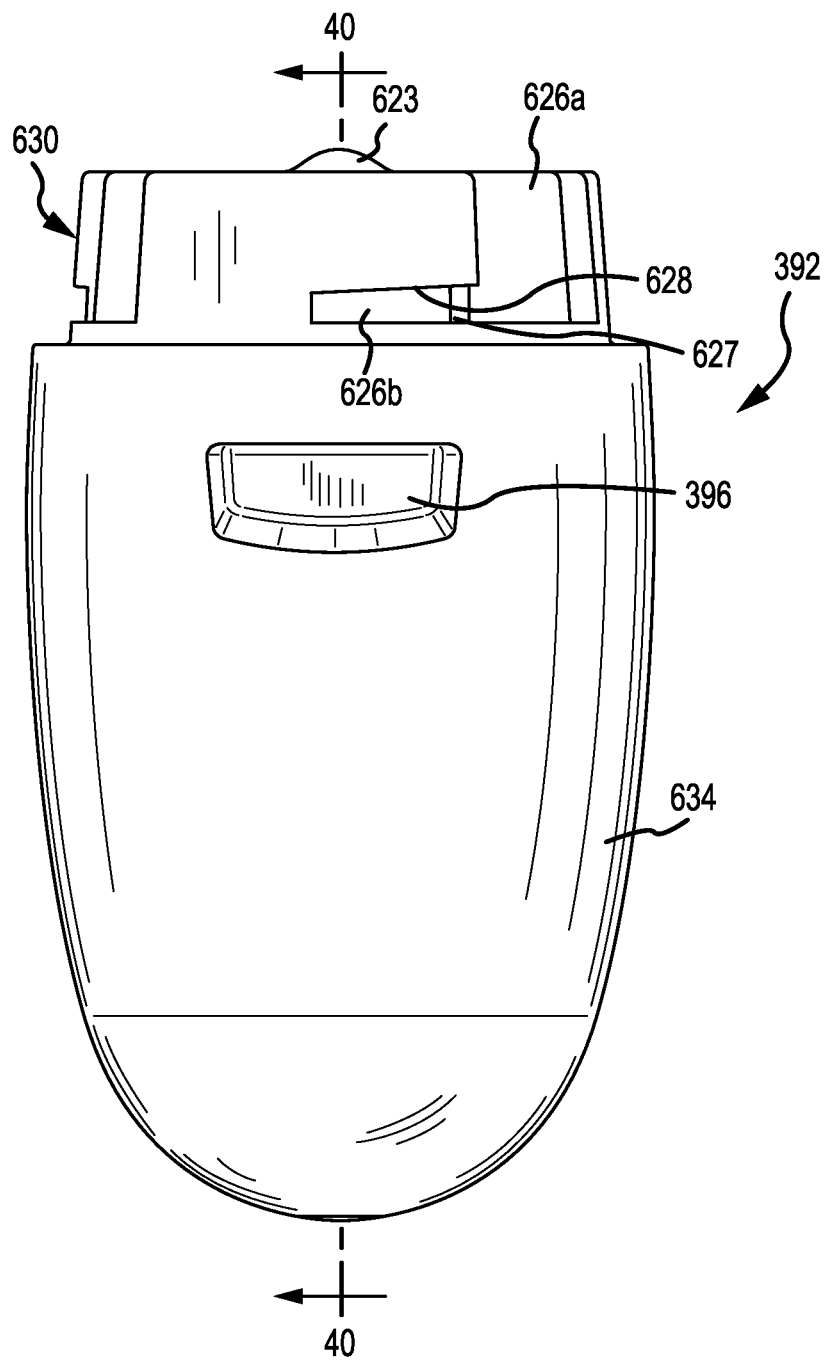
FIG. 39B is a rear elevation view of the battery pack.
Figure 39C:
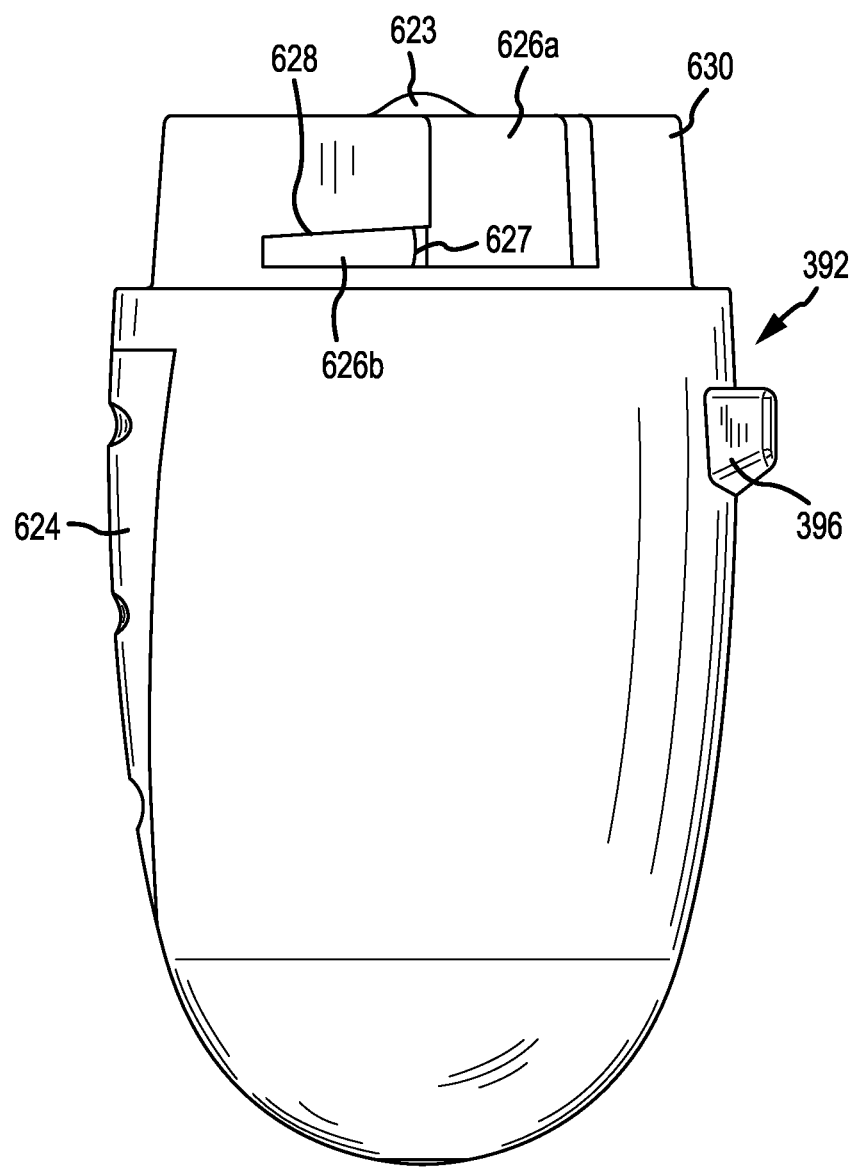
FIG. 39C is a side elevation view of the battery pack.
Figure 40:
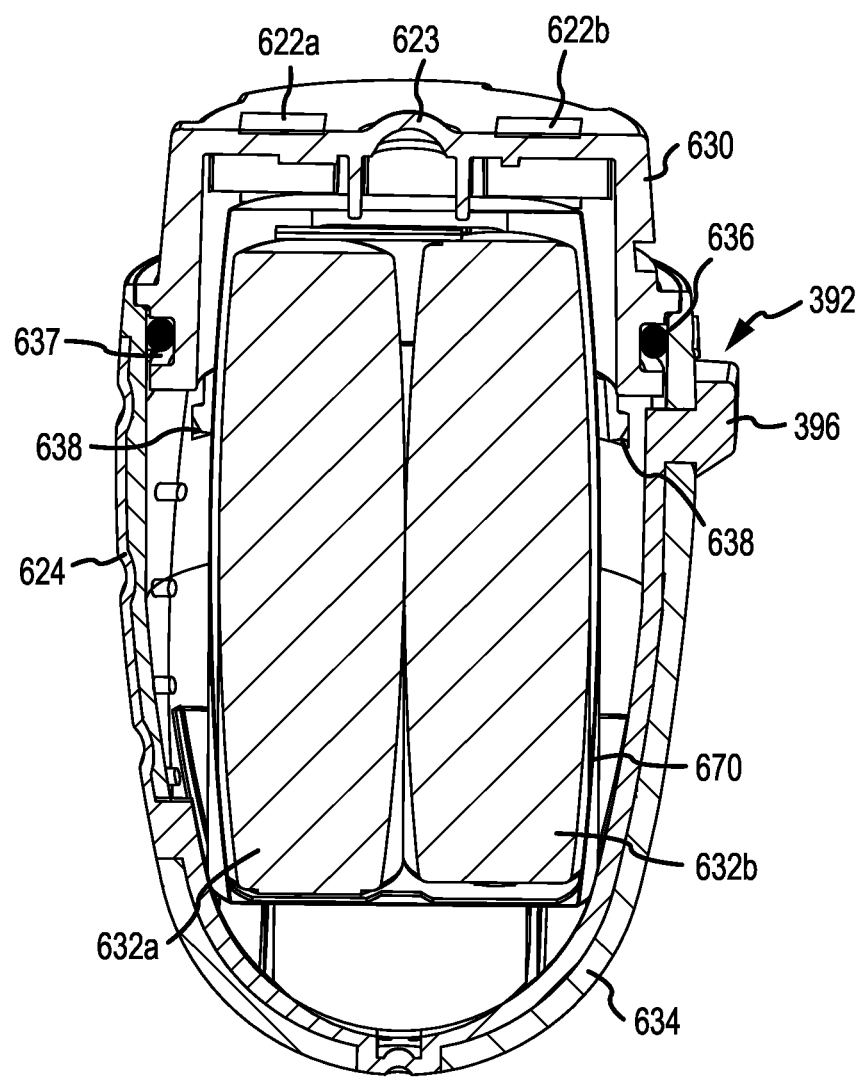
FIG. 40 is a cross-section view of the battery pack taken along line 40-40 in FIG. 39B.

The battery pack 392 will now be discussed in more detail. FIG. 39A is a front isometric view of the battery pack 392. FIG. 39B is a side elevation view of the battery pack 392. FIG. 40 is a cross-section view of the battery pack 392 taken along line 40-40 in FIG. 39B. The battery pack 392 operably connects to the bottom of the water flosser body 380. The battery pack 392 may include a battery housing 634 that houses one or more batteries 632a, 632b.

The battery housing 634 may further include a bottom grip 624 and the stabilizing detent 638. In some embodiments, such as the embodiment illustrated in FIG. 40, the bottom grip 624 and the stabilizing detent 638 may be formed of an overmolded elastomer or rubber. Additionally, the overmold may extend through an interior of the battery housing 634 to connect the bottom grip 624 and the stabilizing detent 638. In these embodiments, a portion of the interior walls of the battery housing 634 may include an overmolded surface.

The stabilizing detent 638 may extend outwards from an aperture within a sidewall of the battery housing 634. In some embodiments, the stabilizing detent 638 may help to prevent the battery pack 392 from easily rolling off flat surfaces when positioned on one of its sides. In other words, the stabilizing detent 638 may interrupt the smooth rounded surface of the battery housing 634, which may interrupt a rolling motion of the battery housing 634 on a smooth surface.

In some embodiments, the batteries 632a, 632b may be positioned asymmetrically within the battery housing 634. In other words, the batteries 632a, 632b may be oriented at an angle relative to the bottom surface of the battery housing 634. In this manner, the batteries 632a, 632b may form an asymmetric mass within the battery housing 634, which may help to reduce the likelihood that the battery pack 392 will roll off a flat surface if positioned on its side.

Figure 41A:
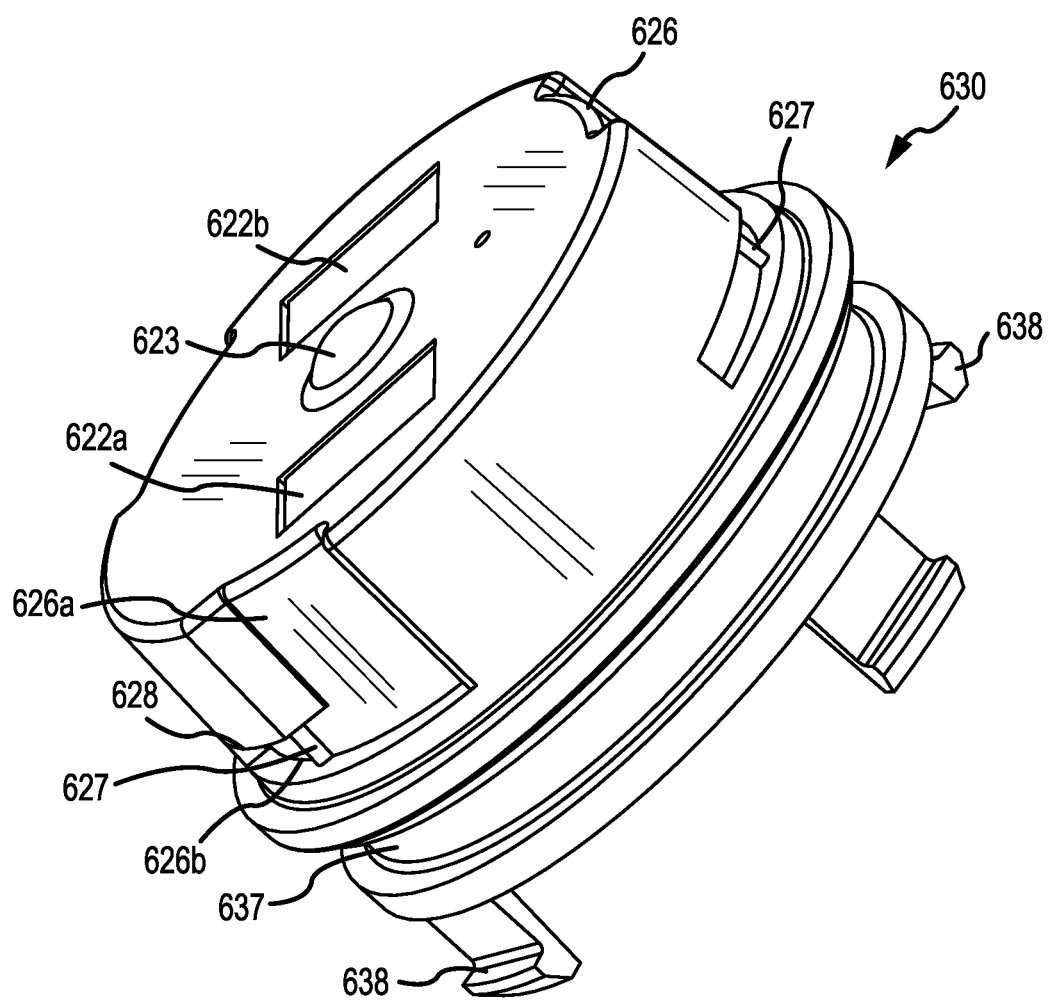
FIG. 41A is a side isometric view of a cap for the battery pack.
Figure 41B:
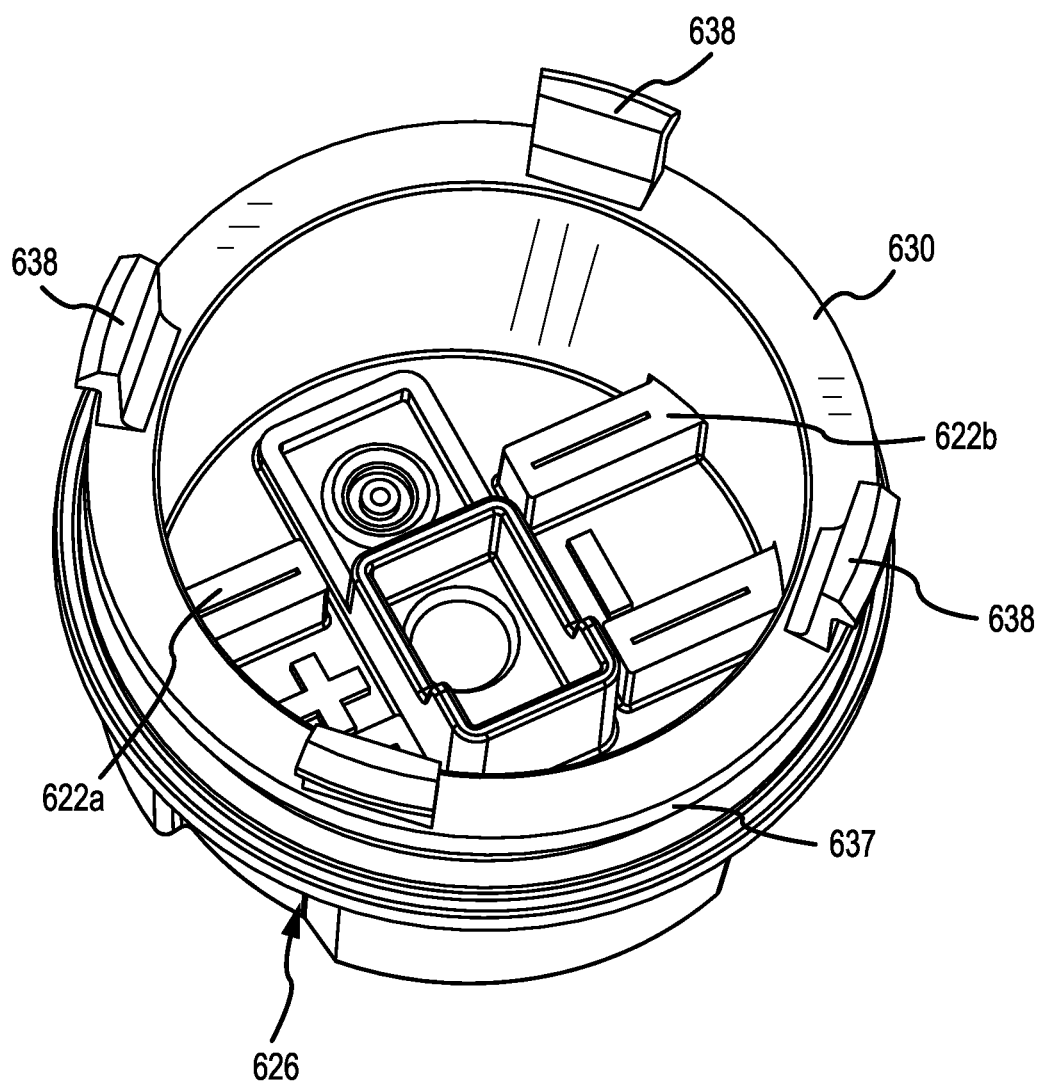
FIG. 41B is a bottom isometric view of the cap.

A battery cap 630 may be operably connected to the top end of the battery housing 634 to enclose the batteries 632a, 632b within the battery housing 634. The battery cap 630 operably connects to the water flosser body 380 and the battery housing 634. FIG. 41A is a top isometric view of the battery cap 630. FIG. 41B is a bottom isometric view of the battery cap. A bottom section of the battery cap 630 may be received within the battery housing 634. The battery cap 630 may operably connect to the battery housing 634 by any of several different mechanisms, such as, but not limited to, twist-lock, snap-fit, and so on. In an exemplary embodiment, the battery cap 630 may include one or more locking detents 638 that may snap-fit into recesses formed within an inner wall of the battery housing 634. The battery cap 630 may also define a seal channel 637 on an outer surface that may receive an O-ring 636 therein. The O-ring 636 may provide a fluid tight seal with an inner wall of the battery housing 634 upon connection between the battery cap 630 and the battery housing 634.

Additionally, the battery cap 630 may operably connect the battery pack 392 to the bottom of the water flosser body 380. As shown in FIG. 41A, the battery cap 630 may have a twist lock interface with two or more a securing slots 626 and a securing feature 628 that may correspond to one or more raised locking features formed on an interior sidewall within a bottom of the water flosser body 380. In this example, each securing slot 626 may be a backward "L"-shape indention with a longitudinal portion 626a and a lateral portion 626b. The slot 626 may be formed within and extend partially around the outer sidewall of the battery cap 630. The securing feature 628 may be a raised portion of the wall above the lateral portion 626b of the slot 626. The locking feature on the interior sidewall of the water flosser body 380 may be in the form of a horizontal ridge. A width of the longitudinal portion 626a may be substantially the same as a width of the lateral portion 626b, both of which may be substantially the same as a length of the horizontal ridge on the interior sidewall of the water flosser body 380. A raised bump or catch 627 may be formed at the interface between the longitudinal portion 626a and the lateral portion 626b to help retain the horizontal ridge within the lateral portion 626b. water flosser With reference to FIGS. 40 and 41A, the top surface of the battery cap 630 may include a raised tension or compression nubbin 638. The tension nubbin 638 may be a rounded protrusion that extends outward from the top surface of the battery cap 630. The top surface of the battery cap 630 may also include one or more battery contacts 622a, 622b. The battery contacts 622a, 622b may extend through the top surface to be in electrical communication with the batteries 632a, 632b. When the battery pack 392 is connected with the water flosser body 380, the battery contacts 622a, 622b may be aligned and in contact with corresponding contacts on the water flosser body 380. The battery contacts 622a, 622b may be formed of an electrically conductive material that transmits power from the batteries 632a, 632b to the motor 412.

With reference to FIG. 40, the batteries 632a, 632b may be received into the battery housing 634 and held within a battery case 670. The battery cap 630 may then be positioned over a top end of the batteries 632a, 632b and the battery case 670 and secured to the battery housing 634. In some embodiments, when connected, a bottom end of the battery cap 630 may extend partially into the battery housing 634. The battery contacts 622a, 622b may be aligned with battery contacts on the battery case 670, so that the battery contacts 622a, 622b may be in electrical communication with the batteries 632a, 632b.

Figure 19A:
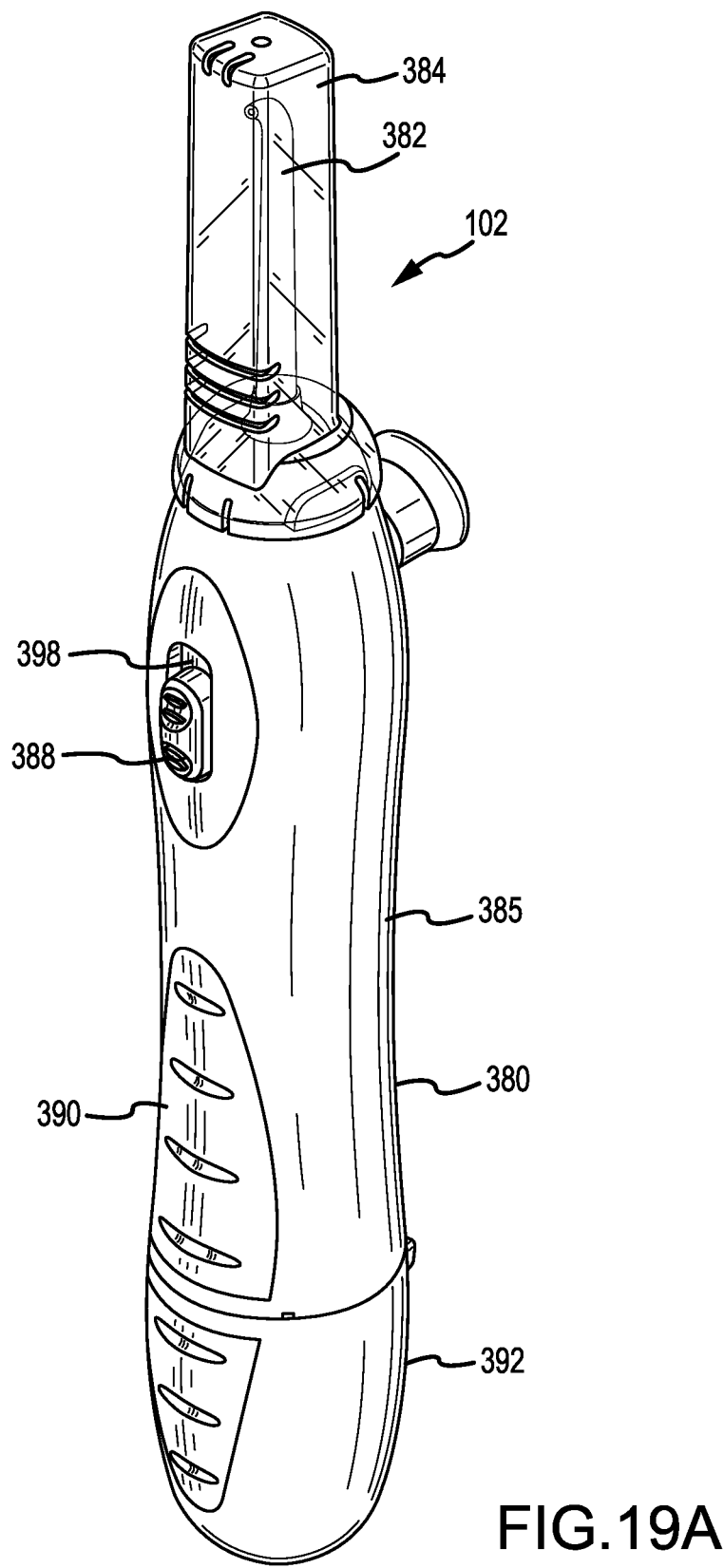
FIG. 19A is a front isometric view of the water flosser.
Figure 19B:
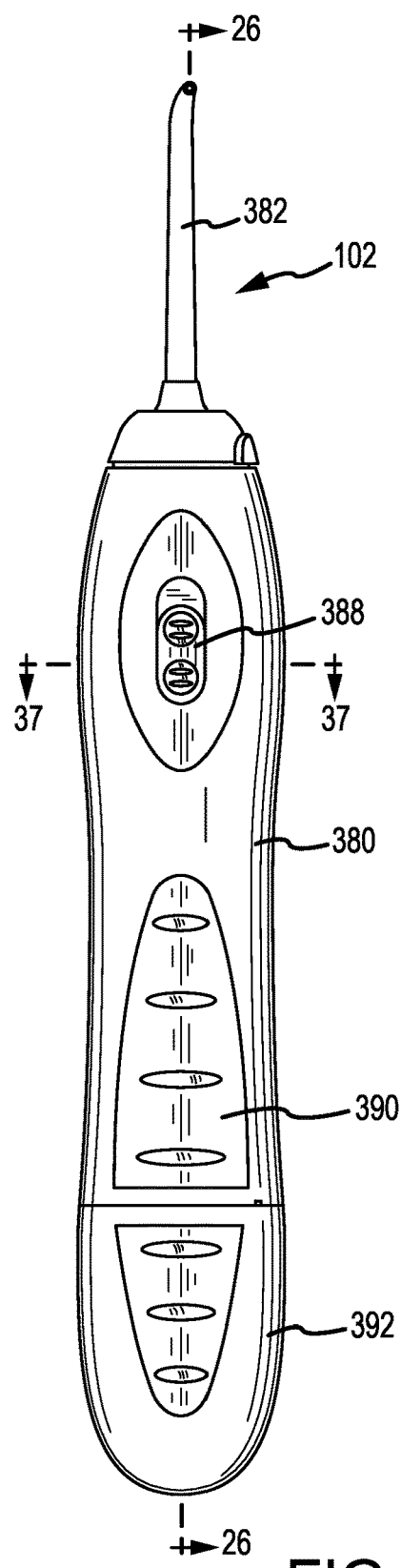
FIG. 19B is a front elevation view of the water flosser.
Figure 19C:
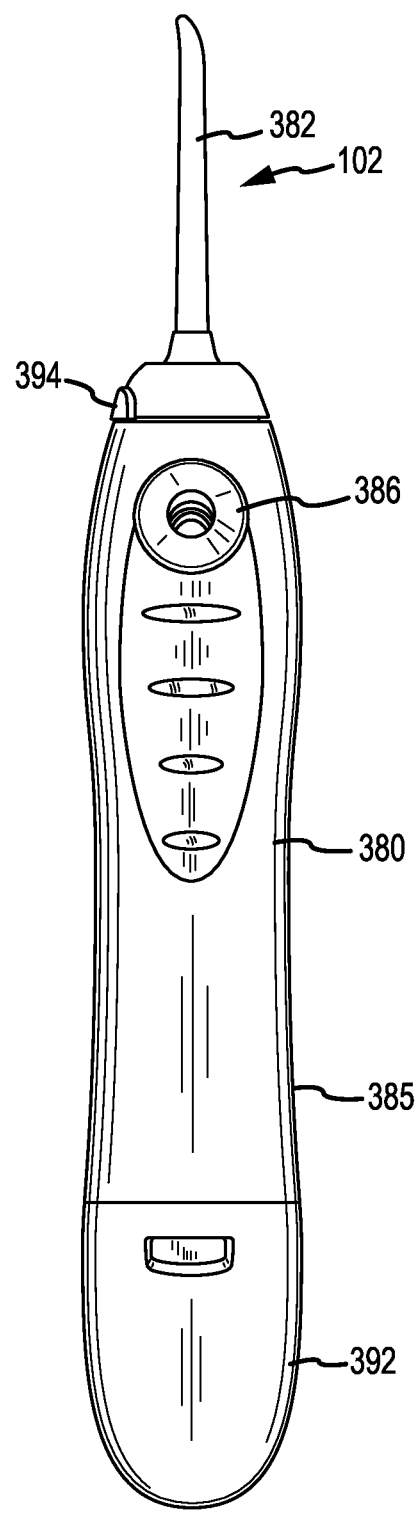
FIG. 19C is a rear elevation view of the water flosser.
Figure 19D:
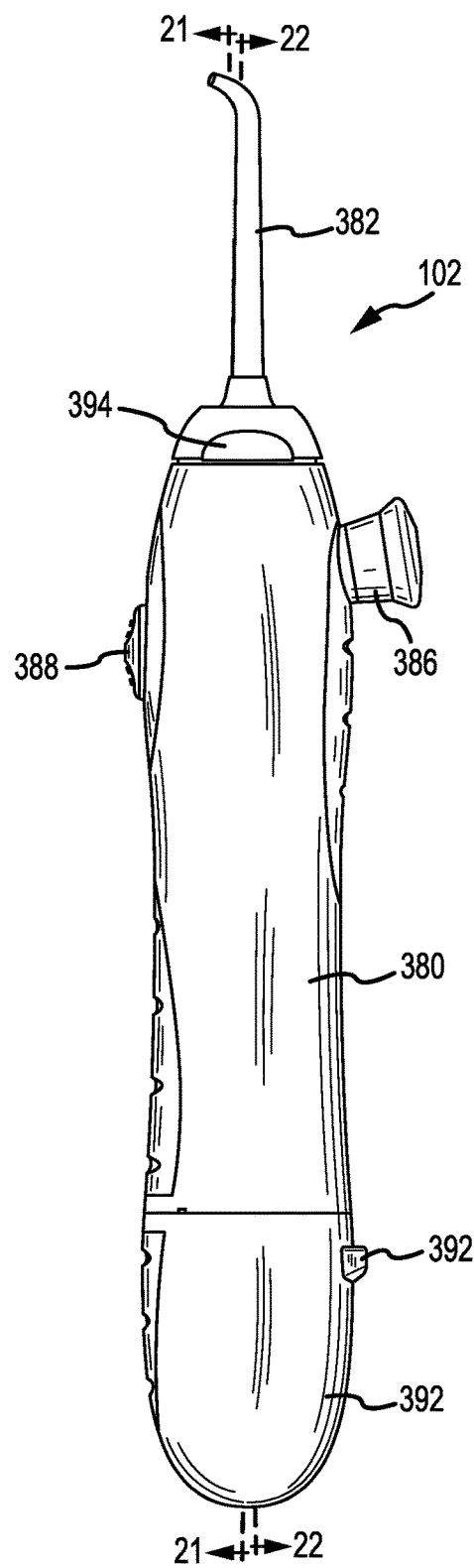
FIG. 19D is a side elevation view of the water flosser.
Figure 19E:
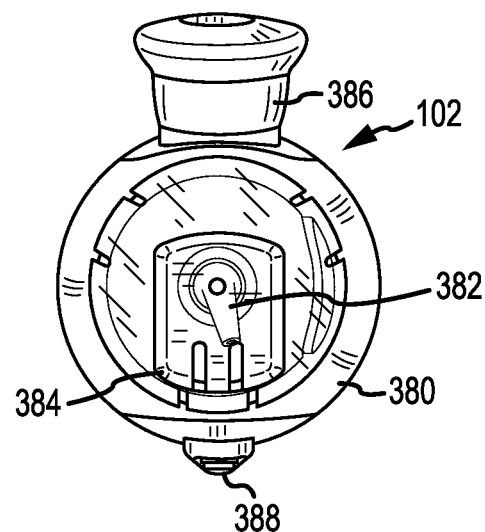
FIG. 19E is a top elevation view of the water flosser.
Figure 19F:
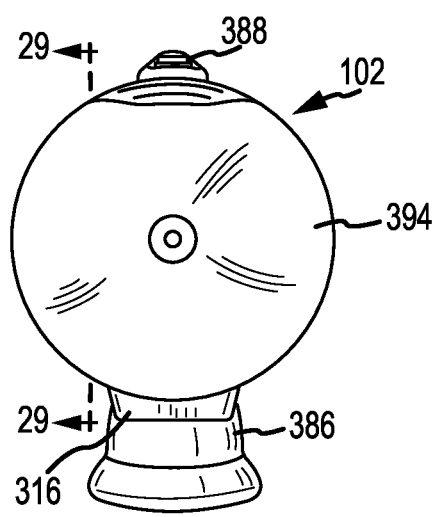
FIG. 19F is a bottom elevation view of the water flosser.

With reference to FIGS. 19A, 21, and 39A, the battery pack 392 may be operably connected to a bottom end of the motor housing 400. When the battery pack 392 is connected to the water flosser housing 385, the tension nubbin 638 may be received into a nubbin recess 428 defined on the bottom of the motor housing 400 to provide a small longitudinal tension between a base of the water flosser housing 385 and the top surface of the battery cap 630 to aid in maintaining a secure connection between the battery pack 392 and the water flosser housing 385. The electrical contacts 622a, 622b on the top surface of the battery pack 392 may be aligned with the electrical contacts 422a, 422b on the bottom surface of the motor housing 400 when the battery pack 392 is inserted into the water flosser housing 385, twisted, and locked into place. In this manner, the motor 412 may be placed in electrical communication with the batteries 632a, 632b.

It should be noted that in some embodiments, the batteries 632a, 632b may be rechargeable. In these embodiments, the battery pack 392 may be removable from the water flosser body 385 and may be received into a battery charger, such as a wall-mount charger. In this example, the battery contacts 622a, 622b may transfer power to the batteries 632a, 632b when in communication with a suitably configured wall mount or other battery charger design. In some exemplary implementations, the batteries 632a, 632b may be charged inductively in a suitable induction charger. Alternatively, the batteries 632a, 632b may be single-use and may be replaced by a user.

Water Flosser Tip

Figure 42A:
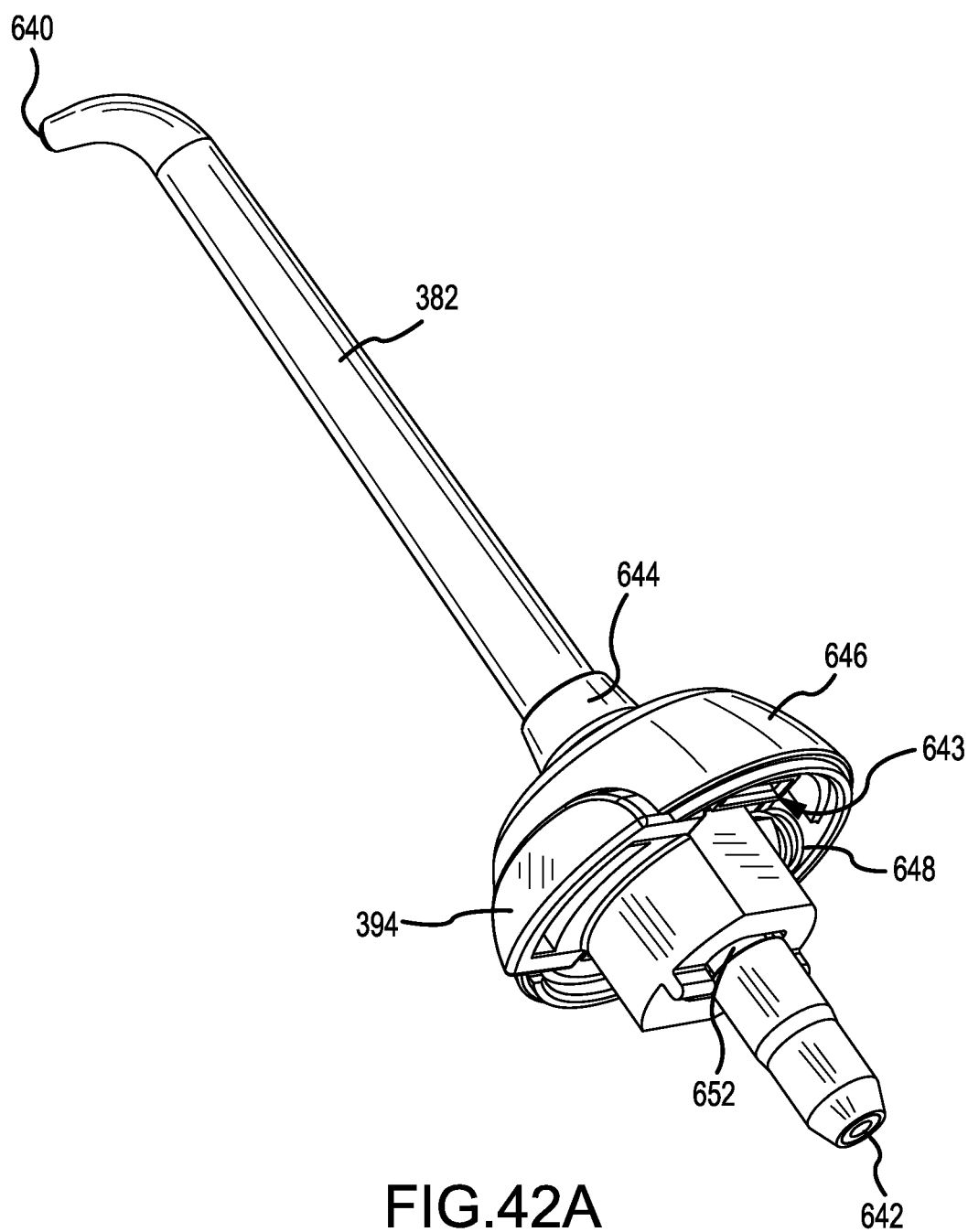
FIG. 42A is a side isometric view of a tip assembly for the water flosser.
Figure 42B:
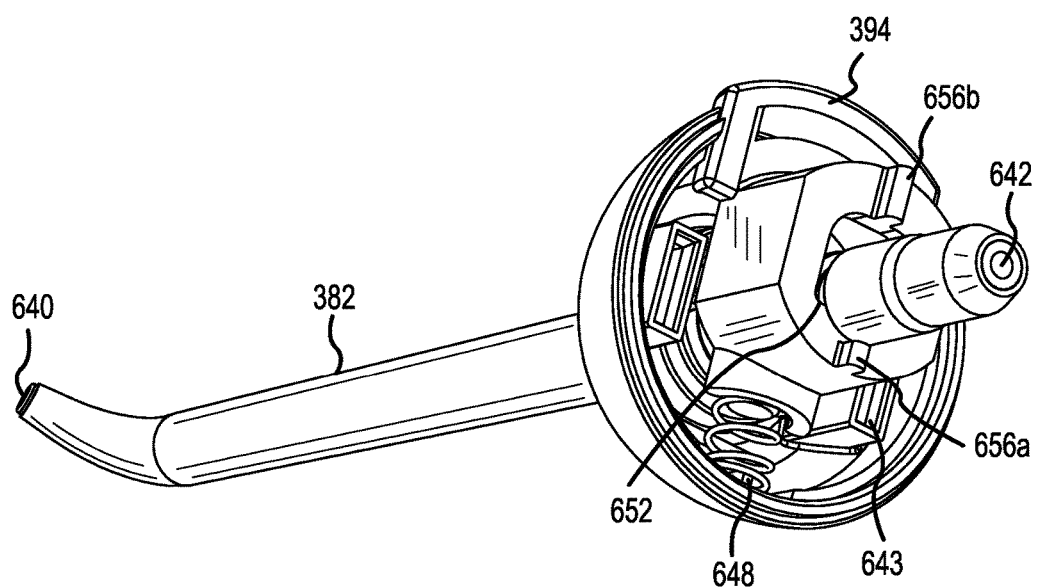
FIG. 42B is a bottom isometric view of the tip assembly.
Figure 43:
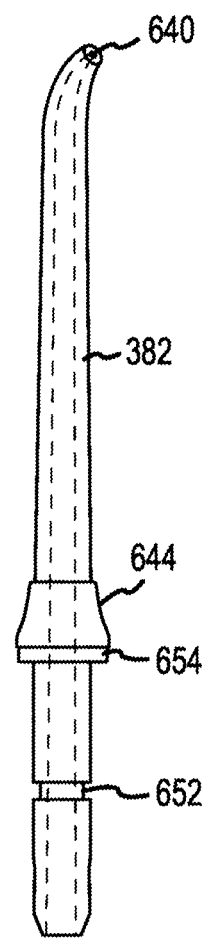
FIG. 43 is a side elevation view of a tip for the water flosser.

The tip 382 of the water flosser 102 may be releasably attached to the water flosser body 380. FIG. 42A is a front isometric view of the tip 382. FIG. 42B is a bottom isometric view of the tip 382. FIG. 43 is a front elevation view of the tip removed from its base. The tip 382 may be formed as a tapered longitudinal tube and may include a tip outlet 640 and a tip inlet 642. The tip inlet 642 may be fluidly connected to the primary valve 558 and may provide fluid to the tip outlet 640. In some embodiments, the tip outlet 640 may have a reduced diameter as compared to the tip inlet 642. The tip outlet 640 may be angled or curved away from a longitudinal axis of the tip 382.

The tip 382 may include a locking groove 652, which may be defined as an annular groove near a bottom end of the tip 382. Additionally, in some embodiments, the tip 382 may have a reduced diameter towards a bottom end adjacent the tip inlet 642.

The tip 382 may further be operably connected to a tip collar 644 and a tip base 646. The tip collar 644 may be a frustum shaped member that extends around the outer wall of the tip 382. The tip collar 644 may also define a shelf 654, which may be configured to receive one or more user indicators (e.g., colored bands to differentiate tips between multiple users).

The tip base 646 may be configured to receive the tip inlet 642 and a portion of the tip 382 that extends below the tip collar 644. The tip base 646 may include a tip locking mechanism 650 and a tip release button 394. The tip release button 394 may be movably connected to the tip base 646 and may selectively disengage the tip locking mechanism 650. The tip locking mechanism 650 may include a movable lock housing 658 that is selectively engageable with the tip 388 and, specifically, the tip locking groove 652. In the exemplary embodiment shown, the lock housing 658 may define an oblong aperture through which the tip 382 extends. A raised ridge 659 on an inner wall of the lock housing 658 defining the oblong aperture may be aligned with the tip locking groove 652. The tip release button 394 and the lock housing 658 may also be operably connected to a tip release spring 648. In the embodiment shown, the tip release spring 648 is positioned between the lock housing 658 and a wall 649a extending from the top of the tip connector 649. (See FIGS. 20A and 20B.) The tip release spring 648 biases the lock housing 658 into the locking groove 652 when the tip 382 is inserted through the tip base 646 into the tip connector 649. The tip release button 394 may be used to push the lock housing 658 against the tip release spring 648 and remove the edge of the lock housing 658 from within the locking groove 652, there by allowing the tip 382 to be removed from the tip base 646.

The tip locking mechanism 650 may include one or more alignment ridges 656a, 656b extending from a bottom surface thereof. The alignment ridges 656a, 656b may interface with one or more grooves or recesses defined in a top water flosser surface of the tip connector 649 to guide the travel of the button 394 and lock housing 658 when depressed. Further, in the exemplary embodiment shown, the tip base 646 may define a pair of sleeves 643 into which a pair of fluted walls 647 (see FIG. 22) extending from a top surface of the tip connector 649 are received in order to attach the tip base 646 to the tip connector 649. The tip base 646 may thus covers the tip connector 393 and the tip ort 560.

With reference to FIGS. 21, 22 and 33, the tip 382 may be operably connected to the primary valve 558 via the tip receiver section 609 of the tip port 560. A downwardly oriented annular wall of the tip connector 649 may be secured to the top end of the primary valve 558 within a connector receiver section 607 of the tip port 560 positioned above the tip receiver section 609. The tip inlet 642 may thereby pass through the connector receiver section 607 and seat within the tip receiver section 609. A sealing member 611 (e.g., an annular cup seal) may seat on an annular ledge of the tip receiver section 609 and be contained by the annular wall of the tip connector 649 to provide a fluid tight seal between the tip inlet 642 and the tip port 560. The tip inlet 642 is thereby retained within the tip port 560 of the primary valve 558 and a fluid tight seal is achieved.

Operation of the Pressure Regulator

In operation, water flows from the J pipe or other water source into the mounting bracket 104. With reference to FIGS. 1 and 6, water flows through the inlet port 150 and into water supply assembly 206. Water then enters into the pivot ball 220 and the water filter 208. Water exits the water supply assembly 206 through an aperture defined in the pivot seat 210. As the water exits the pivot seat 210, it enters the bracket cavity 224 and may then either enter into the regulator assembly 204 or travel through the showerhead extension 154 to the showerhead outlet port 132. In the showerhead flow path, water flows from the bracket cavity 224, around the outer surface of the pressure regulator housing 230, and into the showerhead outlet port 132. Once in the showerhead outlet port 132, the water may flow to the showerhead 106 operably connected to the showerhead extension 154. Water then may exit the showerhead 106 through one or more nozzles.

Alternatively, while the water is within the bracket cavity 224, it may enter into the regulator assembly 204. With reference to FIG. 6, water may flow past the distal face 279 of the regulator body 264 and flow around the poppet 270 through the poppet aperture 306 defined in the poppet seat 268. Once the water has exited through the poppet aperture 306, the water may be contained within the regulator body 264 between the diaphragm 272 and the poppet seal 268. The water may then exit the regulator body 264 through the two exit apertures 294 and enter the flow channel 292. However, the exit apertures 294 may be relatively small in diameter and may not allow a substantial amount of water to exit therethrough at a time. Accordingly, the water may press against the diaphragm 272, causing the flexible body 346 to flex or extend towards the regulator cap 266. As the diaphragm 272 flexes under increasing water pressure, the piston 274 (which is connected to the diaphragm 272) moves towards the regulator cap 266, pulling the poppet 270. The piston 274 compresses the biasing member 276 and moves the diaphragm 272 toward the regulator cap 266.

As the poppet 270 moves with the piston 274, the sealing member 332 of the poppet 270 is pulled toward and engages the sealing walls 314 of the poppet seal 268. At a predetermined water pressure, the sealing member 332 of the poppet 270 seals the poppet aperture 306 as the sealing member 332 (specifically the frustum portion 338) abuts against and engages the chamfered surface 315a of the sealing wall 314. With the poppet 270 sealing member 332 engaged with the chamfered surface 315a, water may be substantially prevented from being able to flow through the poppet aperture 306.

With the poppet aperture 306 sealed, the water pressure between the diaphragm 272 and the poppet seat 268 may gradually reduce as water flows through the exit apertures 294. As the water flows through the exit apertures 294, and without new water from the water supply being able to enter through the poppet aperture 306, the pressure within the regulator body 264 between the poppet seal 268 and the diaphragm 272 may be reduced. As the pressure reduces, the force exerted by the biasing member 276 on the piston 274 overcomes the water pressure and returns the diaphragm 272 and the piston 274 to their original positions. Because the poppet 270 is operably connected to the piston 274, the poppet 270 is forced backwards towards the distal face 279 of the regulator body 264. The sealing member 332 of the poppet 270 disengages from the chamfered surfaces 315a of the poppet seat 268 and unseals the poppet aperture 306. As the larger diameter of the sealing member 332 is moved away from the edges of the poppet seat aperture 306, the smaller diameter of the elongated body 328 of the poppet 270 is positioned between the sealing walls 314. Due to the smaller diameter of the elongated body 328, water may flow around the poppet 270 body and through the poppet aperture 306.

Once the poppet aperture 306 becomes unsealed, water may enter through the poppet aperture 306 faster than it exits out through the exit apertures 294. Again, the water pressure may build against the diaphragm 272 and, once the pressure reaches a predetermined level, may compress the biasing member 276, thereby pulling the poppet 270 to seal against the poppet aperture 306. As the poppet 270 moves back and forth within the poppet seat 268 it rapidly seals and unseals the poppet aperture 306, resulting in a relatively constant water pressure of the water flow through the irrigator flow aperture 236. Thus, the regulator assembly 204, and specifically, the movement of the poppet 270, reduces the pressure of the water from the supply source before providing the water to the water flosser 102. In some embodiments, the water provided to the water flosser 102 may have a pressure ranging between 8 to 15 Pascal.

As water exits the regulator body 264 through the exit aperture 294, the water flows into the flow channel 292 and out through the irrigator flow aperture 236 defined in the bottom of pressure regulator housing 230. The O-rings 296a, 296b provide a fluid tight seal between the regulator body 264 and the pressure regulator housing 230 and prevent water flowing out of the exit apertures 294 from leaking back into the bracket cavity 224, such that the water from the exit apertures 294 flows into the irrigator flow aperture 236.

The pressure regulation provides a consistent to the water flosser as opposed to the water pressure of the water supply source, which may vary depending upon the user setting of the valve supplying water to the shower pipe. The consistent water pressure is possible as the biasing force of the biasing member 272 may be configured to compress (sealing the poppet aperture 306) at a predetermined water pressure. Thus, by selecting the biasing force of the biasing member 272 (e.g., using a spring having a particular spring constant or k value), the water pressure of water exiting the regulator assembly 204 may be predetermined.

In some embodiments, it may be desirable to have a reduced water pressure provided to the water flosser 102 as compared to the water pressure provided to the showerhead 106. By reducing the pressure of the water from the water supply, the regulator assembly 204, the motor 412 does not have to overcome a large pressure head in the primary valve 558. If the water pressure entering the water flosser port 386 is too high, the motor 412 may not be able to generate enough power or torque to overcome the pressure on the shuttle 590 within the primary valve 558.

As water exits the irrigating flow aperture 236 it may travel through the hose 108 and into the oral irrigating port 386 of the water flosser 102. With reference to FIGS. 23 and 29, as water enters the oral irrigating port 386 it flows into the transport hose 410, which then provides the water to the valve water inlet port 550 of the pressure control assembly 534.

Operation of the Water Flosser

Once inside the pressure control assembly 534, the water flow may be determined by the switch 388. As described above, the switch 388 is operably connected to the pivot connector 474, which is in turn is operably connected to the contact leaf 454 and pressure control valve 492. Accordingly, as the switch 388 is moved relative to the water flosser body 385, the pivot connector 474 varies a position of the contact leaf 474 and the pressure control valve 492. As the contact leaf 474 moves, it completes a circuit between the batteries 632a, 632b and the motor 412), and as the pressure control valve 492 position changes, the water pressure outlet through the tip 382 may be varied. Therefore, by varying the position of the switch 388, the water flosser 102 may be switched between an "off" state, a "low pressure" state, and a "high pressure" state. Each state for the water flosser is discussed, in turn, below.

Off Position

Figure 44:
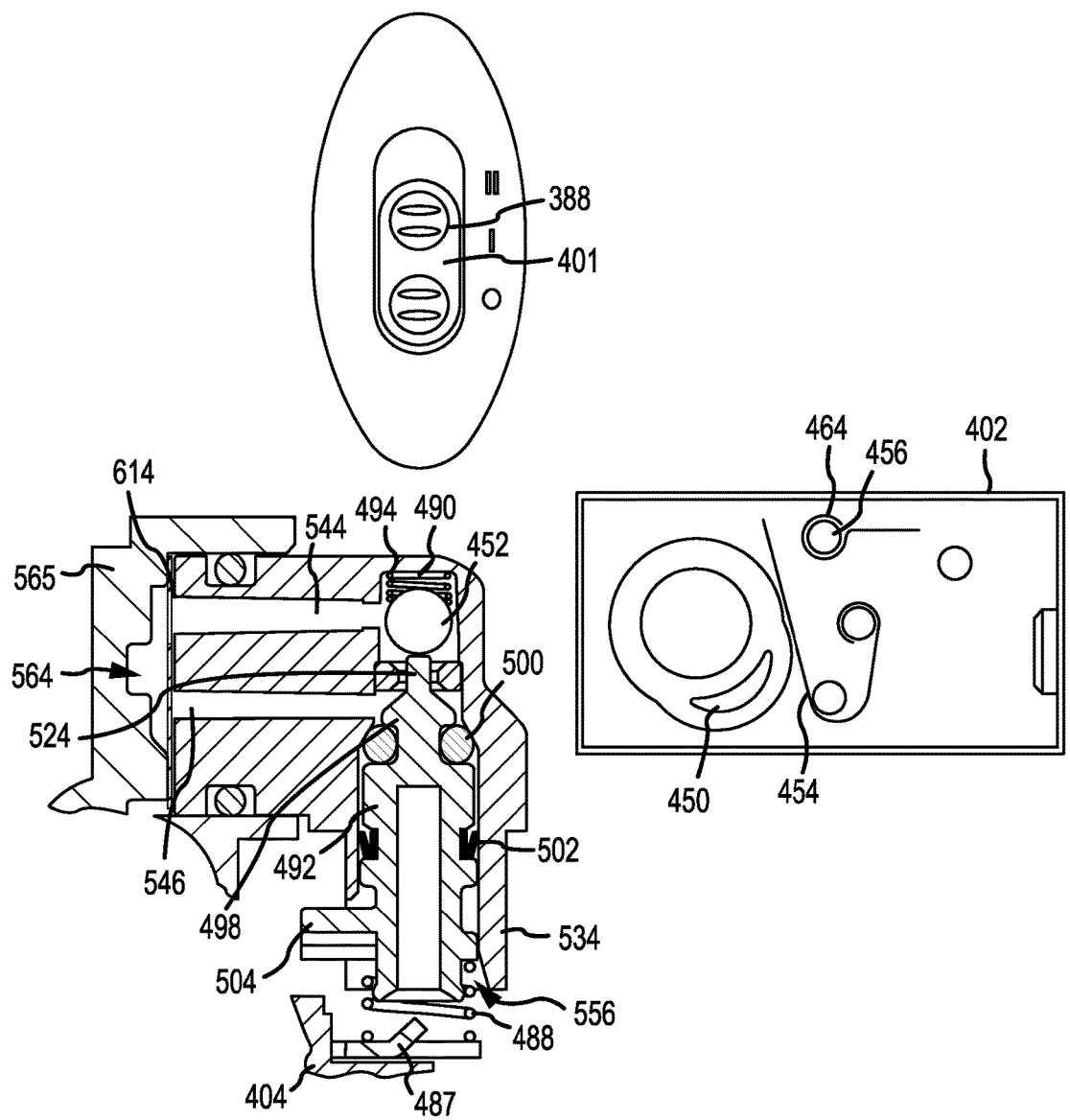
FIG. 44 is a simplified diagram of the switch, the pressure control assembly, and the switch box when the water flosser is in a low pressure state.

FIG. 44 is a simplified diagram of the pressure control assembly 534, the switch 388, and the switch box 402 when the switch 388 is in an off position. With reference to FIGS. 21, 24A, 37 and 44, as the switch 388 is positioned in a first or "off" position, the switch cam 450 may be in a first position and the contact leaf 292 presses against a side thereof. In the first or off position, the contact leaf 454 may be spatially separated from the electrical contact 464 on contact pin 456, as the switch cam 450 does not press the contact leaf 454 towards the contact pin 456.

In this first position, the contact leaf 454 is disconnected from the electrical contact 464. Thus, the electrical circuit between the power source (batteries 632a, 632b) and the motor 412 may be open preventing the transmission of current from the batteries to the motor 412 via the wires 462. In the disconnected state, the motor 412 does not rotate the motor shaft 424. Therefore the pump piston arm 434 is idle.

With reference to FIGS. 24A and 44, in the off position the pressure control valve 492 may be in a first position within the valve chamber 556 of the pressure control assembly 534. In this position, as shown in FIG. 44, the flow control spring 488 may provide a biasing force to push the nose 524 of the pressure control valve 492 against the sealing ball 452. In response, the sealing ball 452 compresses the pressure control spring 490, allowing the pressure control valve 492 to be positioned near to the top end of the valve chamber 556.

In the off position, the sealing O-ring 500 on the pressure control valve 492 seals against the sealing walls 545a, 545b within the valve chamber 556, thereby preventing water from the valve water inlet port 550 from flowing into the outlet conduit 556 and/or the pressure release conduit 554. Thus, the sealing O-ring 500 of the pressure control valve 492 prevents water from flowing from the transport hose 410 to the primary valve 558 and thus out the tip 382. Accordingly, in the off position, there is no water outflow through the tip 382.

The bias of the flow control spring 488 is associated with the position of the pivot connector 474. Specifically, in the off position, the cam arm 504 of the pressure control valve 492 may be positioned within the cam recess 514 at the largest dimension of the cam recess 514. In other words, the cam arm 504 is positioned against the cam surface 486 at a first, elevated edge of the cam surface 486, which slopes downward towards a second, lower edge of the cam surface 486. In this position, the valve block 484 does not force the pressure control valve 492 downward to compress the flow control spring 488. Accordingly, the flow control spring 488 biases the pressure control valve 492 upward in the valve channel 552 to the position illustrated in FIG. 44.

Low Pressure Position

Figure 45:
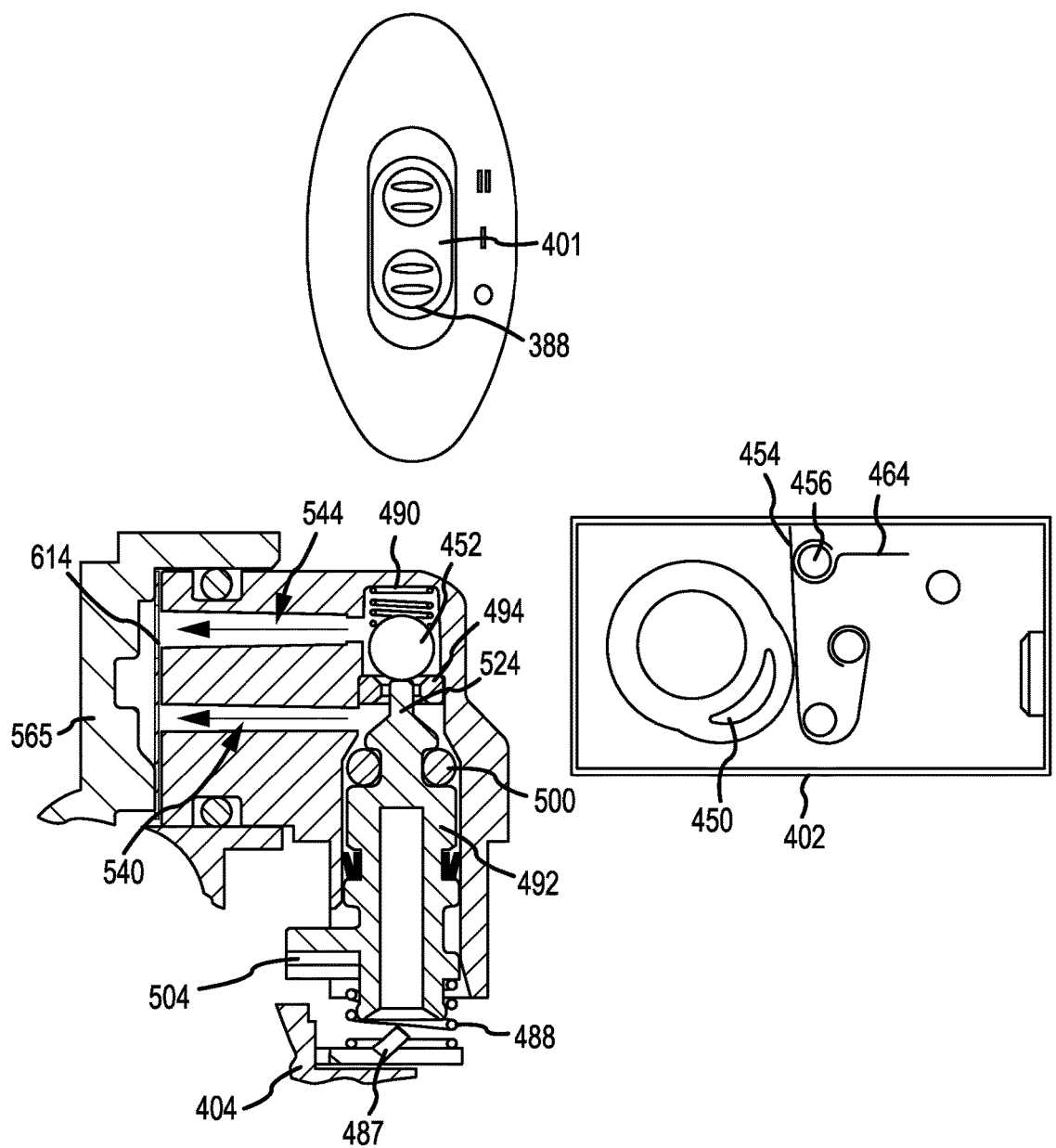
FIG. 45 is a simplified diagram of the switch, the pressure control assembly, and the switch box when the water flosser is in a low pressure state.

When the switch 388 is moved upwards relative to the water flosser body 385, the switch 388 may move into the second or "low pressure" position. In some embodiments, as described above, the switch frame may include one or more feedback detents or teeth that may indicate to a user that the switch 388 has been moved into a second position. FIG. 45 is a simplified diagram of the switch 388, the pressure control assembly 534, and the switch box 402 when the water flosser 102 is in a low pressure state. As the switch 388 is moved to the second position, the pivot ball 478 of the pivot connector 474 is rotated as the pivot ball legs 506a, 506b move correspondingly with the switch 388. As the pivot connector 474 pivots relative to the switch plate 404 on the pivot rods 476a, 476b, the valve control arm 480 and the switch control arm 482 move correspondingly.

With reference to FIGS. 24A and 45, as the switch control arm 482 moves in response to the movement of the switch 388 to the first position, the driver post 516 within the lever slot 512 of the switch control arm 482 moves, thereby rotating the pivot connector 474. As described, the pivot connector 474 is fixed to the switch driver 472, so rotation of the pivot connector 474 rotates the switch driver 472, which further rotates the switch cam 450. The switch cam 450 presses the contact leaf 454 into the electrical contact 465 and the contact pin 456, completing the circuit between the batteries 632a, 632b and the motor 412. As the circuit is completed, the motor 412 receives power and begins to rotate the motor shaft 424, which in turn rotates the small gear 432 and the large gear 430. The pump piston arm 434 is eccentrically connected to the large gear 430, thus the position of the pump piston arm 434 relative to the primary valve 558 oscillates as the large gear 430 rotates. The pump piston arm 434 moves up and down relative to the longitudinal axis of the water flosser 385 as the large gear 430 is rotated. The oscillation of the pump piston arm 434 consequently causes the shuttle 590 to move up and down or back and forth within the primary valve chamber 556.

With reference to FIG. 45, as the valve control arm 480 moves or rotates, the sloped cam surface 486 slides along the cam arm 504 of the pressure control valve 492. The cam surface 486 of the block 484 pushes the cam arm 504 downward (as compared to the off position) as an intermediate position of the cam surface 486 (i.e., a position between the elevated edge and the lower edge of the cam surface 486) contacts the cam arm 504. The downward force on the pressure control valve 492 compresses the flow control spring 488 (at least partially) and the pressure control valve 492 moves downward within the valve chamber 556 (e.g., away from the closed end of the valve chamber 556). As the pressure control valve 492 moves within the valve chamber 556, the sealing O-ring 500 disengages from the sealing walls 545a, 545b. Further, as the nose 524 of the control valve 492 moves downward, the sealing ball 452 also moves downward within the valve chamber 556 by the force exerted from the pressure control spring 490. However, as shown in FIG. 44, in the low pressure position, the sealing ball 452 remains slightly elevated above the sealing washer 494 by the nose 524 of the pressure control valve 492.

With the pressure control valve 492 in the low pressure position as illustrated in FIG. 45, water enters into the valve chamber 556 through the valve water inlet port 550 and flows around the sealing O-ring 500 and pressure control valve 492 to reach the outlet conduit 556. Additionally, because the nose 524 of the pressure control valve 492 supports the sealing ball 452 above the sealing washer 494 water flows through the sealing washer 494 to reach the pressure release conduit 554. Water further flows into the reed valve chamber 564 from the pressure release conduit 554 conduit 556.

With reference to FIG. 33, water that enters the reed valve chamber 562 then passes through the reed valve chamber outlet 572 to flow into the primary valve chamber 586. Once in the primary valve chamber 586, the water may be forced to the tip 382 by the shuttle 590 attached to the pump piston arm 434, which is operated by the motor 412.

During an induction or intake stroke (i.e., the pump piston arm 434 pulls the shuttle 590 downward), negative pressure may be created in the primary valve chamber 586. The negative pressure pulls open the flap 616 of the reed valve 614 and thus allows water within the outlet conduit 546 to flow into the reed valve chamber 564 and further be fluidly connected to the primary valve chamber 586. The reed valve nubbin 574 may prevent the flap 616 of the reed valve 614 from overextending, which could prevent the flap 616 from closing. The negative pressure also pulls the back flow ball 610 to seat against the back flow walls 613 in the black flow chamber 612, thereby preventing any water in the tip 382 from flowing back into the primary valve chamber 586.

During a compression stroke (i.e., the pump piston arm 434 pushes the shuttle 590 upward), water in the primary valve chamber 586 is forced through the outlet port 611 and to the back flow chamber 612. The water pressure in the black flow chamber 612 unseats the back flow ball 610 from the back flow walls 613 such that water can flow around the back flow ball 610 and through the flow apertures 606 defined in the ball stop plate 600. The water may then flow into the tip inlet 642 and eventually out through the tip outlet 640. The oscillating movement of the shuttle 590 and consequent intake and compression strokes, creates a pulsed water flow effect from the primary valve chamber 586 that exits the tip 382 in a pulsed stream.

The force of the water and the shuttle 590 during a compression stroke also passes through the reed valve chamber outlet/primary valve inlet 572 and closes the flap 616 of the reed valve 614 to prevent water from flowing out of (or into) the outlet conduit 546. However, water can still flow into the pressure release conduit 544 and into the valve chamber 556 of the pressure control assembly 534. To the extent that the pressure created by the shuttle 590 in the primary valve chamber 586 is greater than the water pressure in the water inlet port 550 received from the pressure regulator assembly 204, which it typically would be, water flow through the pressure release conduit 544 will push into the transport hose 410 and back against the water flow from the pressure regulator assembly 204. As a result of this pressure release through the pressure release conduit, the pressure of the water flow through the tip 382 in the low pressure configuration of the water flosser 102 will be less than if the pressure release conduit 544 were closed. It may be noted that in this configuration, the pressure on each side of the reed valve 614 will be equal and thus it will stay in the closed position during the compression stroke.

High Pressure Position

Figure 46:
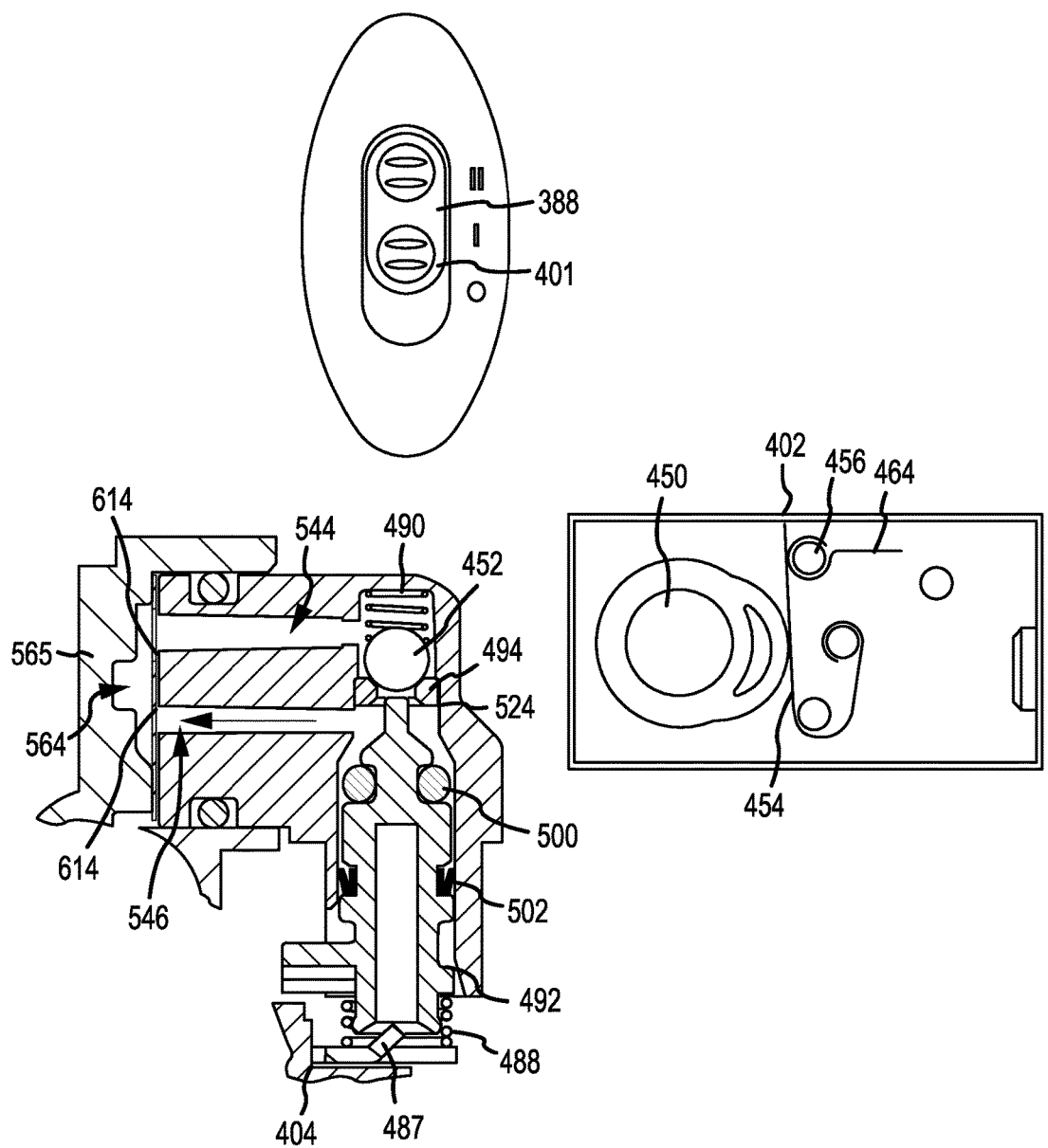
FIG. 46 is a simplified diagram of the switch, the pressure control assembly, and the switch box when the water flosser is in a high pressure state.

When the switch 388 is moved upwards from the low position to a third or "high pressure" position, the water flosser 102 may enter a high pressure state. FIG. 46 is a simplified diagram of the switch 388, the pressure control assembly 534, and the switch box 402 when the water flosser is in a high pressure state. As the switch 388 is moved to the third or high position, the pivot ball 478 of the pivot connector 474 is rotated as the pivot ball legs 506a, 506b move correspondingly with the switch 388. As the pivot connector 474 pivots on the pivot rods 476a, 476b relative to the switch plate 404, the valve control arm 480 and the switch control arm 482 move correspondingly.

With reference to FIGS. 24A and 46, as the switch control arm 482 moves in response to the movement of the switch 388 to the second position, the driver post 516 within the lever slot 512 of the switch control arm 482 moves further, thereby rotating the pivot connector 474 further. As before, rotation of the pivot connector 474 rotates the switch driver 472, which further rotates the switch cam 450. The switch cam 450 presses further on the contact leaf 454, which may flex against the electrical contact 465 and the contact pin 456 while maintaining the circuit between the batteries 632a, 632b and the motor 412. The motor 412 continues to rotate the motor shaft 424 at the same speed (i.e., the motor 412 need only be a single speed motor) to operate the pump.

With reference to FIG. 24A and FIG. 46, as the valve control arm 480 moves, the sloped cam surface 486 slides further with respect to the cam arm 504. The lower edge of the cam surface 486 defines the smallest dimension of the cam recess 514. In the high pressure position, the cam surface 486 further pushes the cam arm 504 downward (as compared to the low pressure position) as the lower edge of the sloped cam surface 486 contacts the cam arm 504. In this position, the cam surface 486 exerts a force on the cam arm 504 in the direction of the switch plate 404, which, in turn, causes the cam arm 504 to compress the flow control spring 488. As the flow control spring 488 is compressed, the pressure control valve 492 moves further out of the valve chamber 556.

With reference to FIG. 46, as the pressure control valve 492 moves downward within the valve chamber 556, the nose 524 of the pressure control valve 492 drops below the sealing washer 492, disengaging from the sealing ball 452. The sealing ball 452, which is biased by the pressure control spring 490, then seats on the sealing washer 492. The pressure control spring 490 counters the water pressure of water flowing in through the water inlet port 550 from the lifting the sealing ball 452 off of the sealing washer 494. With the sealing ball 452 seated on the sealing washer 492, water from the water inlet port 550 is blocked from reaching the pressure release conduit 554.

The entire flow of water may then be directed into the outlet conduit 556 and, when the flap 616 of the reed valve 614 is open (e.g., during an intake stroke of the pump piston arm 434), water flows through the reed valve chamber 564 and into the primary valve chamber 586. As in the low pressure state, the shuttle 590, in correlation with the pump piston arm 434, pulls the water into the primary valve chamber 586 during an intake stroke and pushes the water through the tip 382 during a compression stroke. Similar to the low pressure state, the oscillating movement of the pump piston arm 434 causes a pulsed water flow through the tip 382.

The force of the shuttle 590 on the water during a compression stroke also passes through the reed valve chamber outlet/primary valve inlet 572 and closes the flap 616 of the reed valve 614 to prevent water from flowing out of (or into) the outlet conduit 546. In contrast to the low pressure mode, in the high pressure mode, water is also prevented from flowing into the pressure release conduit 544 because the sealing ball 452 is seated on the sealing washer 492. Water from the pressure release conduit 544 is thus blocked from entering the valve chamber 556 of the pressure control assembly 534. With the pressure release conduit 544 closed, the full pressure generated by the pumping of the shuttle 590 is imparted to the water flow through the tip 382. The outflow pressure from the tip 382 is thus higher than in the low pressure configuration of the water flosser 102. It may be noted that in this configuration, the water pressure on the reed valve chamber 564 side of the reed valve 614 will be greater than the water pressure from the water inlet port 550 and thus the reed valve 614 will stay in the closed position during the compression stroke.

Accordingly, the pressure of the water may be increased in the high pressure state as compared with the low pressure state. By varying the flow paths for the water, the water flosser 102 may provide varying outlet water pressures using a single speed motor 412. A single mechanical switch 388 controls both an electrical switch to actuate the motor 412 and a mechanical valve linkage to selectively produce two different outlet pressures.

CONCLUSION

The foregoing description has broad application. For example, while examples disclosed herein may focus on showerhead water supplies, it should be appreciated that the concepts disclosed herein may equally apply to substantially any other type of fixed water supply, such as sinks and faucets. Similarly, although the irrigating unit may be discussed with respect to a single speed motor, the devices and techniques disclosed herein are equally applicable to other types of drive mechanisms. Accordingly, the discussion of any embodiment is meant only to be exemplary and is not intended to suggest that the scope of the disclosure, including the claims, is limited to these examples.

The coupling member, the showerhead bracket, and other elements of the various examples of the showerhead assembly may be integrally formed or may be made of two or more separate components that are joined together by mechanical fasteners, sonic or heat welds, adhesives, chemical bonds, any other suitable method, or any combination thereof. All directional references (e.g., upper, lower, upward, downward, left, right, leftward, rightward, top, bottom, above, below, vertical, horizontal, clockwise, and counterclockwise) are only used for identification purposes to aid the reader's understanding of the examples of the invention, and do not create limitations, particularly as to the position, orientation, or use of the invention unless specifically set forth in the claims. Joinder references (e.g., attached, coupled, connected, joined and the like) are to be construed broadly and may include intermediate members between the connection of elements and relative movement between elements. As such, joinder references do not necessarily infer that two elements are directly connected and in fixed relation to each other.

What is claimed is:

1. An interdental cleaner for operably connecting to an external water supply comprising
  a mounting bracket having a bracket inlet fluidly connected to the external water supply;
  a pressure regulation assembly operably connected to the mounting bracket, the pressure regulation assembly having a regulation outlet fluidly connected to the bracket inlet, wherein the pressure regulation assembly is housed within the mounting bracket and comprises
    a sealing member positioned within a flow path between the external water supply and the regulation outlet;
    a diaphragm operably connected to the sealing member; wherein the diaphragm moves the sealing member between a first open position and a second sealed position; and
    a biasing member operably connected to the diaphragm, wherein the biasing member moves the sealing member to the first open position from the second sealed position;
    a regulator body receiving the sealing member and the diaphragm, the regulator body having a length and defining a flow cavity that extends through the length, and a sidewall, wherein the regulation outlet is defined through the sidewall;
      in the first open position a portion of the regulator body is in fluid communication with the bracket inlet; and
      in the second sealed position, the portion of the regulator body is not in fluid communication with the bracket inlet such that water within the flow cavity flows out through the regulation outlet, reducing a water pressure between the diaphragm and the sealing member; and
  a water flosser operably connected to the mounting bracket and fluidly connected to the regulation outlet; wherein
  the regulator body provides a water flow having a substantially constant pressure; and
  a water pressure of water at the regulation outlet is lower than a water pressure of water at the bracket inlet.

2. The interdental cleaner of claim 1, wherein the mounting bracket further comprises
  a showerhead outlet for connecting to a showerhead; wherein
  the showerhead outlet is in fluid communication with the bracket inlet and a water pressure at the showerhead outlet is substantially the same as the water pressure at the bracket inlet.

3. The interdental cleaner of claim 1, wherein
  the sealing member includes a body having a first portion with a first width and a second portion with a second width; and
  the pressure regulation assembly further comprises a poppet seal having a sealing wall defining a poppet aperture; wherein
  the sealing member is at least partially received in the poppet seal;
  in the first open position the first portion is received in the poppet seal; and in the second sealed position the second portion is received in the poppet seal and abuts against the sealing wall.

4. The interdental cleaner of claim 1, wherein as the water pressure between the diaphragm and the sealing member reduces, a biasing force exerted by the biasing member returns the diaphragm to the first open position, preventing water from flowing out of the regulation outlet.

5. The interdental cleaner of claim 1, wherein the biasing member is a coil spring.

6. The interdental cleaner of claim 1, wherein the pressure regulation assembly further comprises a piston operably connected to the biasing member, the diaphragm, and the sealing member.

7. The interdental cleaner of claim 1, further comprising a pump positioned within the water flosser, wherein the pump pumps water received from the regulation outlet to a flosser outlet in the water flosser.

\* \* \* \* \*